United States Patent [19]

Rainer

[11] 4,093,812
[45] June 6, 1978

[54] (NITROFURYL)PYRAZOLES, THEIR SYNTHESIS AND USE, AND COMPOSITIONS CONTAINING THEM

[75] Inventor: Georg Rainer, Constance, Germany

[73] Assignee: Byk Gulden Lomberg Chemische Fabrik GmbH, Constance, Germany

[21] Appl. No.: 669,611

[22] Filed: Mar. 23, 1976

[30] Foreign Application Priority Data

Mar. 25, 1975 Luxembourg .................. 72129
Feb. 20, 1976 Luxembourg .................. 74400

[51] Int. Cl.$^2$ ............... C07D 231/12; A61K 31/415
[52] U.S. Cl. ............... 548/374; 424/273 P; 426/2
[58] Field of Search ............... 548/374; 424/273 P

[56] References Cited

U.S. PATENT DOCUMENTS

| 3,716,555 | 2/1973 | Howarth et al. ............... 548/374 |
| 3,755,324 | 8/1973 | Hoyle et al. ............... 548/374 |

FOREIGN PATENT DOCUMENTS

48-39,935   11/1973   Japan.

OTHER PUBLICATIONS

Chemical Abstracts: vol. 64: p12683c; vol. 69: 86901d & vol. 70: 68242f.

*Primary Examiner*—Donald B. Moyer

*Attorney, Agent, or Firm*—Berman, Aisenberg & Platt

[57] ABSTRACT

3-(5-Nitro-2-furyl)pyrazoles unsubstituted in the 5-position and 5-(5-nitro-2-furyl)pyrazoles unsubstituted in the 3-position are antimicrobials and disinfectants. The compounds are structurally represented by one of the formulae:

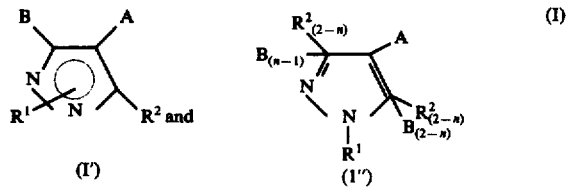

wherein
  A is —CHO, —CN, —COOH, a protected or derived aldehyde group or a protected or derived carboxylic acid group;
  B is 5-nitro-2-furyl;
  $R^1$ is —H, substituted or unsubstituted hydrocarbyl (saturated or unsaturated; acyclic, alicyclic or aromatic; or araliphatic); substituted or unsubstituted (cycloaliphatic or aromatic) heterocyclic or acyl (carboxylic or carbonic acid);
  $R^2$ is —H; and
  $n$ is a positive whole number of at most 2.

85 Claims, No Drawings

(NITROFURYL)PYRAZOLES, THEIR SYNTHESIS AND USE, AND COMPOSITIONS CONTAINING THEM

SUMMARY OF THE INVENTION

The present invention is directed to 1-R$^1$-[3- or 5-(5-nitro-2-furyl)]-4-pyrazole[carbaldehydes, (protected)-carbaldehydes, (derived)carbaldehydes, carbonitriles, carboxylic acids, (protected)carboxylic acids, and (derived)carboxylic acids]wherein R$^1$ is —H, substituted or unsubstituted (straight- or branch-chain, saturated or unsaturated) aliphatic hydrocarbyl, substituted or unsubstituted (saturated or unsaturated) cycloaliphatic, substituted or unsubstituted (mono- to tri-cyclic, carbocyclic and/or heterocyclic) aromatic, nuclearly-substituted or unsubstituted ar(mono- to tri-cyclic, carbocyclic and/or heterocyclic)alkyl, ar(mono- to tri-cyclic, carbocyclic and/or heterocyclic)alkenyl, or organic acyl of a carboxylic or carbonic acid.

Compounds (I) are medicaments, disinfectants and preserving agents which are administered or applied in suitable compositions in which they are present in a concentration effective for the designed purpose.

Definitions

Throughout the disclosure and claims all terms (unless otherwise defined) are accorded their ordinary and accepted meanings. A number of terms are hereinafter defined and are used throughout the text with the following definitions in the absence of a clear indication to the contrary.

acyclic — aliphatic.

acyl — an acid radical such as that formed by removing the —OH of a carboxylic acid [R-CO-OH] or of a carbonic acid [RO-CO-OH], wherein R is an organic residue; includes radicals of mono- and poly-basic carboxylic acids generally used for acylating nitrogen bases and of carbonic acid monoalkyl esters in which the alkyl is substituted or unsubstituted lower alkyl.

acyloxy — acyl-O-, e.g. acetoxy.

aldehyde — organic compound containing the —CHO radical; it oxidizes to a corresponding acid and reduces to a corresponding alcohol; alternatively referred to as a free aldehyde; it is represented as R-CHO wherein R is an organic residue.

alicyclic — cycloaliphatic; pertaining to a closed chain or ring of (substituted or unsubstituted, saturated or unsaturated) carbon atoms, one or more (but less than all) of which are optionally replaced by a hetero atom (preferably —O—, —S— and/or =N—); the closed chain or ring has, e.g., from 3 to 7 (preferably 5 or 6) ring members, but is not so restricted, and any unsaturation is of aliphatic, rather than aromatic, character; alicyclic or cycloaliphatic hydrocarbon radicals include, e.g., cyclopropyl, cyclobutyl, cyclopentyl, cyclohexyl, cycloheptyl and their unsaturated analogues, such as 2-cyclopentenyl, 3-cyclohexenyl and 2,4-cyclohexadien-1-yl; other alicyclics include, e.g., 2-piperazinyl, 3-pyrazolin-2-yl, 3-morpholinyl, 2-piperidyl and 2-thiomorpholinyl.

aliphatic — an organic compound or radical that has an open chain of carbon atoms, whether normal or forked, saturated or unsaturated; it includes substituted or unsubstituted alkyl, alkenyl and alkynyl, preferably those regarded as "lower"; unsaturation is either mono (as in allyl) or multiple (as in butadienyl), and multiple unsaturation can (but need not) be conjugated.

alkanoyl — acyl of an alkanoic acid; substituted or unsubstituted aliphatic (preferably lower) hydrocarbylcarbonyl wherein the hydrocarbyl is ordinarily alkyl, but unsaturated analogues, e.g. alkenyl and alkynyl, are also included; illustrative embodiments include acetyl, propionyl, butyryl, crotonoyl and 2-penten-4-ynylcarbonyl.

alkenyl — an aliphatic hydrocarbon radical with one or more olefinic double bonds and no triple bonds when more than one double bond is present, they are either conjugated or non-conjugated; exemplary radicals include those with from 1 to 7 carbon atoms, e.g. vinyl, allyl, 1-propenyl, isopropenyl, 2-butenyl, 1,3-butadienyl and 2-pentenyl.

alkoxy — alkyl-O-, e.g. ethoxy and isopropoxy.

alkyl — saturated aliphatic hydrocarbyl, either straight chain (normal) or forked (branched); exemplary embodiments include normal radicals with from 1 to 7 carbon atoms, e.g. methyl, ethyl, propyl, butyl, pentyl, hexyl and heptyl, of which those with from 1 to 4 (and, more particularly, 1 or 2) carbon atoms are preferred, and their branched counterparts with from 3 to 7 carbon atoms, e.g. isopropyl, sec.-butyl, tert.-butyl, 3-methylbutyl, 2,2-dimethylpropyl, 2-methylpentyl, 3,3-dimethylbutyl and 2-ethyl-3-methylbutyl, of which those with from 3 to 5 (and, more particularly, 3 or 4) carbon atoms are preferred.

alkylene — a saturated aliphatic hydrocarbon from which 2 hydrogen atoms have been removed; although alkylene is unlimited with regard to number of carbon atoms, those contemplated herein have from 2 to 5 (preferably 2 or 3) carbon atoms between available bonds and are optionally substituted by alkyl having from 1 to 5 (preferably 1 or 2) carbon atoms; suitable embodiments include ethylene, propylene, butylene and pentylene.

alkynyl — an aliphatic hydrocarbon radical with at least one triple bond, preferably those having from 2 to 7 carbon atoms, e.g. ethynyl, 2-propynyl, 3-heptynyl and 2-pentyn-4-yl.

aralkenyl — aryl-substituted olefinically-unsaturated hydrocarbyl, e.g. styryl.

aralkyl — aryl-substituted saturated aliphatic hydrocarbyl, e.g. benzyl, β-naphthylmethyl and thenyl.

aromatic — a substituted or unsubstituted radical a) having a benzene ring or a condensed ring system (at least one ring of which is a benzene ring) from which a benzene-ring hydrogen atom has been removed or b) having an unsaturated heterocyclic (containing at least one ring carbon atom and one or more ring =N-, —O— and/or —S— atoms) ring (or a ring system) possessing aromatic unsaturation characteristics (thermal stability, addition and oxidation resistance, undergoing electrophilic substitution, possessing considerable resonance energy) of benzene and from which unsaturated heterocyclic ring a ring hydrogen atom has been removed; a compound having in its molecular structure one or more of the previously-defined radicals; preferred aromatic groups have up to three rings (nuclei), each with 5 or 6 ring members, and up to 12 ring carbon atoms; homocyclic aromatic groups include, e.g., phenyl, indanyl and naphthyl, of which phenyl is preferred; heterocyclic aromatic groups include, e.g., pyrrolyl, imidazolyl, oxazolyl, thiazolyl, pyridyl, pyrazinyl, pyrimidinyl, pyridazinyl, thiadiazolyl, triazolyl, benzimidazolyl, benzthiazolyl, benzoxazolyl, quinolyl, phthalazinyl and isoquinolyl, preferably 2-, 3-and 4-pyridyl.

aroyl — aromatic with an -H (bound to an aromatic-ring carbon atom) replaced by —CO—.

aryl — a homocyclic, i.e. carbocyclic, or heterocyclic aromatic radical, e.g. phenyl, naphthyl and pyridyl.

branched — branch-chained or forked; having a side chain of one or more carbon atoms, e.g. 3,3-dimethylbutyl and 2-ethyl-3-methylbutyl.

carbocyclic — having a homocyclic ring of saturated and/or unsaturated carbon atoms, e.g. cyclohexane and benzene.

carbonic acid — an acid of the formula RO—CO—OH; for organic carbonic acids (ordinarily in ester form R—O—CO—O—R or $R_2CO_3$) R is an organic radical, a carbon atom of which is directly bound to the —O—CO—OH; the acyl of such an acid is R—O—CO—, e.g. benzyloxy-carbonyl.

carboxylic acid — an organic acid of the formula R—CO—OH (in free form), wherein R is an organic radical, a carbon atom of which is directly bound to the —CO—OH, e.g. propionic acid.

cycloaliphatic — saturated or unsaturated carbocyclic (homocyclic) or heterocyclic with aliphatic (rather than aromatic) properties, e.g. cyclohexyl and pyrrolinyl.

derived aldehyde — aldehyde derivative wherein the aldehyde [—CHO] oxygen atom is replaced by a sulfur atom [=S], imino [=NH or $=NR^3$, wherein $R^3$ has one of the meanings of $R^1$], oximino [=N—O—$R^4$, wherein $R^4$ is —H or an acyl group, e.g. alkanoyl with from 1 to 7 (preferably from 1 to 4) carbon atoms or homocyclic (preferably benzoyl) or heterocyclic (such as isonicotinoyl) aroyl], hydrazono or semicarbazono [$=N^1-N^2(R^5)R^6$, wherein $R^5$ is —H or optionally-substituted alkyl; $R^6$ is one of the meanings of $R^7$ or -$C^3(N^4R^7R^8)=Z$; each of $R^7$ and $R^8$ is, independently, —H, optionally substituted alkyl, organic acyl or optionally substituted (homocyclic or heterocyclic) aryl; Z is =NH or, preferably, =O or =S; and $R^5$ and $R^6$ (together with —$N^2$—) are, alternatively, an optionally substituted heterocyclic radical].

derived carboxylic acid — carboxylic acid derivative wherein the carboxyl group [-CO-OH] is modified by replacing the =O of the -CO- and/or preferably replacing the —OH; the —OH is eplaced, e.g., by a halogen atom [chiefly a chlorine or bromine atom], acyloxy [resulting in a symmetrical or mixed acid anhydride], mercapto, azido, —$N(R^{12})R^{13}$ [wherein each of $R^{12}$ and $R^{13}$ is, independently, —H or alkyl-(optionally substituted by —OH) having from 1 to 7 (chiefly from 1 to 4) carbon atoms, or, alternatively, $R^{12}$ and $R^{13}$ (together with the nitrogen atom to which both are bound) are a heterocyclic radical, such as pyrrolidino, piperidino or morpholino], substituted or (preferably) unsubstituted hydroxylamino, or substituted or (preferably) unsubstituted hydrazino [—NH—$N(R^{14})R^{15}$, wherein each of $R^{14}$ and $R^{15}$, independently, has one of the meanings of $R^7$ and $R^8$, respectively]; the =O of the —CO— is replaced, e.g., by =S, =NH, $=NR^3$, =N—O—$R^4$ or $=N-N(R^7)_2$.

heterocyclic — having a closed chain or ring with at least one ring carbon atom and at least one ring atom [=N-, —O— and/or —S—] which is other than a carbon atom; individual ring atoms are saturated or unsaturated, and the ring has either aliphatic or aromatic properties.

homocyclic — having a closed cycloaliphatic or aromatic chain or ring of carbon atoms, e.g. cyclohexene and naphthalene.

hydrocarbyl — a radical which consists of a hydrocarbon from which one hydrogen atom has been removed; a radical consisting solely of carbon and hydrogen atoms, e.g. ethyl, vinyl, cyclohexyl and naphthyl.

lower — as applied to aliphatic groups, one which has from 1 to 7 carbon atoms, monocyclic to tricyclic — having a cyclic ring structure with one ring [e.g. cyclohexyl, phenyl and 2-imidazolin-4-yl] or with two [e.g. α-naphthyl, 7-chromanyl, 2-quinuclidinyl, 1-isoindolinyl and 2-quinolyl] or three [e.g. 2-anthryl, 2-carbolinyl and 2-perhydroanthryl] rings, any one or more of the rings being homocyclic or heterocyclic, cycloaliphatic or aromatic.

nitrile — an organic compound having —CN (the nitrile group) as a substituent in its molecular structure, e.g. cyclohexanecarbonitrile and 2-thiazolecarbonitrile.

organic — relating to a chemical compound containing combined carbon [excluding CO, $CO_2$, $CO_3$ and their compounds with inorganic substances] or a radical thereof.

protected aldehyde — an aldehyde [-CHO] wherein the aldehyde =O is replaced, e.g., by an open-chain acetal, e.g. [-O-(lower)alkyl]$_2$, an open-chain mercaptal, e.g. [—S—(lower)alkyl]$_2$, a ring acetal, e.g. —O—Y—O— [wherein Y is lower alkylene with, e.g., from 2 to 5 (preferably 2 or 3) carbon atoms and optionally substituted by alkyl (of the type preferred for the open-chain acetal and mercaptal) with from 1 to 5 (preferably 1 or 2) carbon atoms] or a ring mercaptal, e.g. —S—Y—S— [wherein Y has its previously-noted meaning].

protected carbocylic acid — a carboxylic acid in the molecular structure of which the carboxyl group [-CO-OH] is modified by replacing the OH by alkoxy with from 1 to 11 (preferably with from 1 to 4) carbon atoms or by an aryloxy with up to 12 carbon atoms (chiefly phenoxy) or by an aralkoxy with up to 14 carbon atoms (chiefly benzyloxy or 1-or 2-phenethoxy, respectively).

radical — a group of elements having an unsatisfied valence and acting as a single element, e.g. —CN, —CHO and —CO—OH.

residue — radical; what is left of the structure of a compound after a specified functional group is removed; the organic residue of a carboxylic acid R—CO—OH is R; the acyl residue of the same acid is R—CO—; the residue of an aldehyde R—CHO is also R.

room temperature — 20° C.

saturated — having no double or triple bonds, e.g. alkanes (methane, ethane) and cycloalkanes (cyclohexane).

straight-chain — open chain; a chain with no branching; a chain with no alkyl substitution, e.g. n-hexyl.

substituted — pertaining to a hydrogen atom of a compound or radical replaced by another element or radical; for aliphatic radicals, such as alkyl, or alkenyl, "substituted" infers single or multiple substitution by one or more of such substitutents as halo, e.g. fluoro, chloro or bromo, the hydroxy group (—OH), lower alkoxy (preferably with from 1 to 4 carbon atoms), acyloxy, e.g. lower alkanoyloxy (preferably with from 1 to 4 carbon atoms) and aryloxy; illustrative substituted aliphatic radicals include, e.g., 3-chloro-2-hydroxypropyl, hydroxymethyl, β-hydroxyethyl, β-hydroxyethyl, β-hydroxypropyl, β-methoxyethyl, β-propoxyethyl, β-acetoxyethyl, β-butyroxyethyl and β-phenoxyethyl; for aromatic radicals, such as phenyl, β-naphthyl and 2-pyridyl, "substituted" infers substitution in any available ring position, preferably with 1 or 2 substituents (which are the same or different) at those positions which are energetically favored, by such substituents as halo (e.g. fluoro, bromo and, preferably, chloro) lower alkyl (preferably with from 1 to 4 carbon atoms), lower alkoxy (preferably with from 1 to 4 carbon atoms), lower alkylmercapto (preferably with from 1 to 4 carbon atoms), trifluoromethyl, nitro, cyclohexyl and phenyl; for heterocyclic aromatic radicals, substituents) include fluoro, chloro, bromo, $C_{1-4}$ alkyl (e.g. methyl) and $C_{1-4}$ alkoxy (e.g. methoxy); illustrative substituted aromatic radicals are o-chlorophenyl, m-chlorophenyl, p-chlorophenyl, m-bromophenyl, p-bromophenyl, p-fluorophenyl, m-tolyl, p-tolyl, 3,4-dichlorophenyl, 3-chloro-p-tolyl, α,α,α-trifluoro-m-tolyl, p-nitrophenyl, m-nitrophenyl, p-methoxyphenyl, p-ethoxyphenyl, 3,4-dimethoxyphenyl, cumenyl, p-butylmercaptophenyl, p-cyclohexylphenyl, p-biphenylyl, 3,4-(methylendioxy)phenyl, 5-indanyl, 4-chloro-1-naphthyl and picolyl, p-substituted-phenyl, such as p-halophenyl, p-tolyl and p-methoxyphenyl, particularly p-chlorophenyl and p-fluorophenyl, are preferred; for aralkyl and aralkenyl radicals, such as benzyl, benzhydryl, cinnamyl, phenethyl, thenyl and styryl, "substituted" infers nuclear substitution in any available ring position similar to that described for aromatic radicals and/or chain (alkylene or alkenylene) substitution similar to that described for aliphatic radicals; illustrative substituted aralkyl and aralkenyl radicals include p-chlorobenzyl, m-chlorobenzyl, p-bromo- benzyl, o-fluorobenzyl, p-fluorobenzyl, p-methoxybenzyl and p-chloro-α-methylstyryl; for alkanoic acid acyl (including unsaturated analogues thereof), such as acetyl, butyryl and crotonoyl, and aliphatic lower hydrocarbyl carbonic acid acyl (preferably with from 1 to 4 and, more especially, with 1 or 2 carbon atoms), such as ethoxycarbonyl, isopropoxycarbonyl and allyloxycarbonyl "substituted" infers single or multiple substitution by one or more of such substituents as hydroxyl (—OH), lower alkoxy (preferably with from 1 to 4 carbon atoms), mono (lower)alkylamino, dialkylamino with up to 7 carbon atoms, aryl (e.g. mono- or disubstituted or preferably, unsubstituted phenyl and α- or β-naphthyl), morpholino, pyrrolidino and piperazino (optionally substituted in the 4-position by alkyl with from 1 to 3 carbon atoms; illustrative of such substituted acyls are β-hydroxypropionyl, 3,4-dimethoxyphenylacetyl, γ-methylaminobutyryl, βdiethylaminopropionyl, cinnamoyl, p-chlorobenzyloxycarbonyl, benziloyl, morpholinoacetyl, β-pyrrolidinopropionyl, β-piperazinobutyryl, γ-(4-methylpiperazino)butyryl and 4-methylpiperazinomethoxycarbonyl; for aromatic carboxylic acid acyl (aroyl), such as benzoyl, naphthoyl and nicotinoyl, and for aromatic carbonic acid acyl (aryloxycarbonyl), such as phenoxycarbonyl, "substituted" infers nuclear substitution in any available ring position, preferably with 1 or 2 substituents (which are the same or different) at those positions which are energetically favored, in the same manner and as previously described with regard to substitution of aromatic radicals; preferred substituents are halo (e.g. fluoro, bromo and chloro), hydroxy (—OH), lower alkyl (preferably with from 1 to 4 carbon atoms), lower alkoxy (preferably with from 1 to 4 carbon atoms) and nitro; illustrative corresponding substituted acyls include 2,4-difluorophenoxycarbonyl, p-hydroxybenzoyl, o-toluoyl, 2-(4-methoxy)naphthoyl, 3-(5-nitro)-pyridylcarbonyl, 3-(4-ethyl)furoyl, 2-(3-propyl)-thenoyl, 4-(3,5-dinitro)pyridyloxycarbonyl; for cycloaliphatic (whether saturated or partially unsaturated; whether as a substituent or e.g., a primary group in an acyl, such as in 3-cyclohexenylcarbonyl or in cyclohexyloxycarbonyl), "substituted" infers mono- or poly-(lower)alkyl substitution, preferably by 1 or 2 alkyl groups (which are the same or different) with from 1 to 4 carbon atoms in each, e.g. 2,4-dimethylcyclohexyl.

unsaturated — having one or more double and/or triple bonds, e.g. styrene, butadiene and acetylene.

Details

The compounds of this invention are of one of the formulae

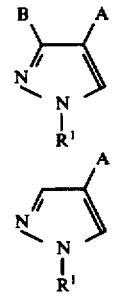

wherein
- A is a free, protected or derived aldehyde group, the nitrile group, or a free, protected or derived carboxylic acid group;
- B is 5-nitro-2-furyl;
- $R^1$ is a hydrogen atom (-H); substituted or unsubstituted, straight- or branched-chain, saturated or unsaturated, aliphatic or alicyclic, such as alkyl, alkenyl, cycloalkyl and 3-morpholinyl; substituted or unsubstituted, homocyclic or heterocyclic, monocyclic to tricyclic aryl; nuclearly-substituted or unsubstituted aralkyl; nuclearly-substituted or unsubstituted aralkenyl; or organic (carboxylic or carbonic) acid acyl;

and thus fall into one of the following categories:
A is a free aldehyde group
  1 (57) $R^1$ is -H 2 (58) R¹ is substituted or unsubstituted (preferably hydrocarbyl) aliphatic
3 (59) R¹ is substituted or unsubstituted alicyclic
4 (60) R¹ is substituted or unsubstituted carbocyclic aryl
5 (61) R¹ is substituted or unsubstituted heterocyclic aryl
6 (62) R¹ is nuclearly-substituted or unsubstituted (heterocyclic or carbocyclic) aralkyl
7 (63) R¹ is nuclearly-substituted or unsubstituted (heterocyclic or carbocyclic) aralkenyl
8 (64) R¹ is organic (carboxylic or carbonic) acid acyl A is a protected aldehyde group
9 (65) R¹ is -H
10 (66) R¹ is substituted or unsubstituted (preferably hydrocarbyl) aliphatic
11 (67) R¹ is substituted or unsubstituted alicyclic
12 (68) R¹ is substituted or unsubstituted carbocyclic aryl
13 (69) R¹ is substituted or unsubstituted heterocyclic aryl
14 (70) R¹ is nuclearly-substituted or unsubstituted (heterocyclic or carbocyclic) aralkyl
15 (71) R¹ is nuclearly-substituted or unsubstituted (heterocyclic or carbocyclic) aralkenyl
16 (72) is organic (carboxylic or carbonic) acid acyl A is a derived aldehyde group
17 (73) R¹ is —H
18 (74) R¹ is substituted or unsubstituted (preferably hydrocarbyl) aliphatic
19 (75) R¹ is substituted or unsubstituted alicyclic
20 (76) R¹ is substituted or unsubstituted carbocyclic aryl
21 (77) R¹ is substituted or unsubstituted heterocyclic aryl
22 (78) R¹ is nuclearly-substituted or unsubstituted (heterocyclic or carbocyclic) aralkyl
23 (79) R¹ is nuclearly-substituted or unsubstituted (heterocyclic or carbocyclic) aralkenyl
24 (80) R¹ is organic (carboxylic or carbonic) acid acyl A is the nitrile group
25 (81) R¹ is -H
26 (82) R¹ is substituted or unsubstituted (preferably hydrocarbyl) aliphatic
27 (83) R¹ is substituted or unsubstituted alicyclic
28 (84) R¹ is substituted or unsubstituted carbocyclic aryl
29 (85) R¹ is substituted or unsubstituted heterocyclic aryl
30 (86) R¹ is nuclearly-substituted or unsubstituted (heterocyclic or carbocyclic) aralkyl
31 (87) R¹ is nuclearly-substituted or unsubstituted (heterocyclic or carbocyclic) aralkenyl
32 (88) R¹ is organic (carboxylic or carbonic) acid acyl A is a free carboxylic acid group
33 (89) R¹ is —H
34 (90) R¹ is substituted or unsubstituted (preferably hydrocarbyl) aliphatic
35 (91) R¹ is substituted or unsubstituted alicyclic
36 (92) R¹ is substituted or unsubstituted carbocyclic aryl
37 (93) R¹ is substituted or unsubstituted heterocyclic aryl
38 (94) R¹ is nuclearly-substituted or unsubstituted (heterocyclic or carbocyclic) aralkyl
39 (95) R¹ is nuclearly-substituted or unsubstituted (heterocyclic or carbocyclic) aralkenyl
40 (96) R¹ is organic (carboxylic or carbonic) acid acyl A is a protected carboxylic acid group
41 (97) R¹ is —H
42 (98) R¹ is substituted or unsubstituted (preferably hydrocarbyl) aliphatic
43 (99) R¹ is substituted or unsubstituted alicyclic
44 (100) R¹ is substituted or unsubstituted carbocyclic aryl
45 (101) R¹ is substituted or unsubstituted heterocyclic aryl
46 (102) R¹ is nuclearly-substituted or unsubstituted (heterocyclic or carbocyclic) aralkyl
47 (103) R¹ is nuclearly-substituted or unsubstituted (heterocyclic or carbocyclic) aralkenyl
48 (104) R¹ is organic (carboxylic or carbonic) acid acyl A is a derived carboxylic acid group
49 (105) R¹ is —H
50 (106) R¹ is substituted or unsubstituted (preferably hydrocarbyl) aliphatic
51 (107) R¹ is substituted or unsubstituted alicyclic
52 (108) R¹ is substituted or unsubstituted carbocyclic aryl
53 (109) R¹ is substituted or unsubstituted heterocyclic aryl
54 (110) R¹ is nuclearly-substituted or unsubstituted (heterocyclic or carbocyclic) aralkyl
55 (111) R¹ is nuclearly-substituted or unsubstituted (heterocyclic or carbocyclic) aralkenyl
56 (112) R¹ is organic (carboxylic or carbonic) acid acyl wherein the first number designates the category for the corresponding compounds of Formula (Ia) and the adjacent number (in parentheses) designates the category for the corresponding compounds of Formula (Ib).

One aspect of the invention is reflected by compounds of formula I (Ia or Ib) in which A denotes a free, protected or derived aldehyde group. These compounds correspond to nitrofurylpyrazole derivatives of formula II

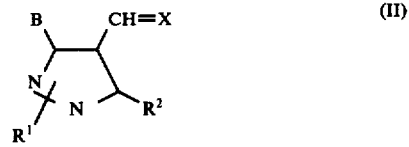

in which R¹ and R² have their previously-ascribed meanings, and X denotes a free, protected or derived oxo group, i.e. —CH=X denotes a free, protected or derived aldehyde group.

A more pecise representation of the aspect of the invention directed to nitrofurylpyrazole derivatives of formula II is reflected by formulas IIa and IIb

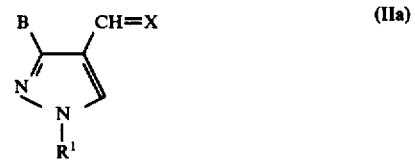

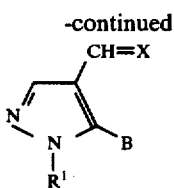

in which $R^1$, B and X have their previously-ascribed meanings.

As a free oxo group X represents an oxygen atom; —CH═X, an aldehyde group. Open-chained or ring acetals or mercaptals, i.e. compounds (II) wherein X is (—O-alkyl)$_2$, (—S-alkyl)$_2$, —O—Y—O— or —S—Y—S— [in which the alkyl radicals comprise 1 to 5 (preferably 1 or 2) carbon atoms and Y denotes an alkylene bridge with 2 to 5 (preferably 2 and 3) carbon atoms] are illustrative of protected aldehyde groups. Each alkyl is, e.g., methyl, ethyl, propyl, butyl, or pentyl; each alkylene Y is, e.g., ethylene, propylene, butylene or pentylene. The alkylene bridge is optionally substituted by one or two of the previously mentioned alkyls.

Derived aldehyde groups include sulfur- or nitrogen-containing derivatives, i.e. those wherein A is -CH═X and X is a sulfur atom, imino, oximino, hydrazono or semicarbazono. For derived aldehydes X is, e.g.:

═N—H;

═N—$R^3$, in which $R^3$ represents one of the meanings of $R^1$;

═N—O—$R^4$, in which $R^4$ denotes a hydrogen atom or acyl, for example alkanoyl with from 1 to 7 (preferably 1 to 4) carbon atoms, aroyl (preferably benzoyl) or a heteroaryl (for example isonicotinoyl);

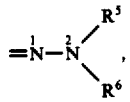

in which $R^5$ denotes a hydrogen atom or optionally-substituted lower alkyl, and $R^6$ denotes a hydrogen atom, optionally-substituted lower alkyl, optionally-substituted aryl (homocyclic or heterocyclic), acyl,

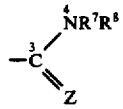

in which $R^7$ and $R^8$ are the same or different and each represents, optionally-substituted aryl (homocyclic or heterocyclic), preferably a hydrogen atom or optionally-substituted lower alkyl, and Z denotes ═NH or, preferably, an oxygen atom or a sulfur atom; or $R^5$ and $R^6$ together with —N$^2$═ is an optionally-substituted heterocycle.

Preferred lower alkyl groups $R^5$ and $R^6$ include straight-chained and branch-chained alkyl radicals with 1 to 3 carbon atoms and which are optionally substituted (preferably in the 2-position) by one or more of the following substituents: a hydroxy group, alkoxy with 1 to 4 carbon atoms and alkanoyloxy with 1 to 4 carbon atoms.

Alkyl groups $R^6$ are those contemplated for alkyl groups $R^5$; aryl group $R^6$ are those contemplated for aryl groups $R^1$.

Heteroaryl groups $R^6$ are chiefly those with from one to three nuclei, are optionally-substituted and are ring-(oxygen-, sulfur- and/or nitrogen-containing) heterocyclic with five or six-membered rings, e.g. furyl, thienyl, pyrrolyl, 2-imidazolyl, 2-oxazolyl, 2-thiazolyl, pyridyl, pyrazinyl, 2- and 4-pyrimidinyl, 3-pyridazinyl, 1,3,4-thiadiazol-2-yl, 1,2,4-triazol-3-yl, 2-benzimidazolyl, 2-benzthiazolyl, 2-benzoxazolyl, quinolyl, 1-phthalazinyl, 4-uracilyl, 1-isoquinolyl, benzo-1,2-thiazole-1,1-dioxide-3-yl, and, preferably, 2-, 3- or 4-pyridyl, pyrazinyl, 3-pyridazinyl, 2-benzimidazolyl, 2-benzthiazolyl, quinolyl, 2-thiazolyl and 2,3-dimethyl-4-uracilyl.

Acyl groups $R^6$ include those contemplated for $R^1$, particularly $R^9$—CO— and $R^{10}$—O—CO—, in which $R^9$ denotes straight-chained or branch-chained alkyl [with 1 to 4 (preferably 1 or 2) carbon atoms and which is optionally substituted by hydroxy, alkoxy with from 1 to 4 carbon atoms (preferably methoxy or ethoxy), dimethylamino, diethylamino, morpholino, pyrrolidino, piperazino or 4-methylpiperazino] or aryl [homocyclic or heterocyclic and optionally substituted (preferably) by one or more substituents, such as hydroxy, alkyl or alkoxy with from 1 to 4 carbon atoms, halo (preferably chloro or bromo) or nitro; such aryl being, for example, phenyl, naphthyl or pyridyl]; and $R^{10}$ denotes straight-chained or branched-chained alkyl [with from 1 to 7 (preferably 1 to 4) carbon atoms and which is optionally substituted, for example, by alkoxy with from 1 to 3 carbon atoms (preferably a methoxy group) or a p-methoxyphenyl radical].

Acyl, (homocyclic and heterocyclic) aryl and alkyl for each of $R^7$ and $R^8$ are of the same scope as the corresponding groups for $R^6$.

When $R^5$ and $R^6$ (together with —N$^2$═) represent a heterocyclic radical, the latter is preferably a five- to six-membered ring which, in addition to the nitrogen atom —N$^2$═, optionally comprises a ring-oxygen atom, a ring-sulfur atom or one or two ring-nitrogen atoms; the heterocyclic radical is optionally substituted by 1 or 2 oxo groups, a thioxo group, 1 or 2 alkyl groups [each with from 1 to 3 carbon atoms and optionally-substituted by hydroxy, alkoxy with from 1 to 3 carbon atoms (preferably methoxy), alkylthio with from 1 to 3 carbon atoms (preferably methylthio), mono- or dialkylamino with up to 7 carbon atoms, morpholino, pyrrolidino, piperazino (optionally substituted with a $C_1$-$C_3$-alkyl group and, preferably, 4-methylpiperazino)] or a condensed-on benzene ring. Such heterocyclic radicals include: pyrrolidino, piperidino, hexamethylenimino, morpholino, 1,4-thiazan-4-yl, piperazino, 1,2,4-triazol-4-yl, benztriazol-1-yl, imidazolidin-2-on-1-yl, oxazolidin-2-on-3-yl, imidazolidine-2,4-dion-1-yl, imidazolidine-2-thion-1-yl, 1,4-thiazane-1,1-dioxide-4-yl, oxindol-1-yl, 4-oxo-3,4-dihydrobenzo-1,2,3-triazin-3-yl, 2-methylpiperidino, 4-methylpiperidino, 2,6-dimethylpiperidino, 2,6-dimethylmorpholino, 4-methylpiperazino, 3-methyl-1,4-thiazane-1,1-dioxide-4-yl, 4-(2-hydroxyethyl)piperazino, 3-hydroxymethylimidazolidine-2,4-dione-1-yl, 3-(2-hydroxyethyl)imidazolidine-2-on-1-yl, 4-methylimidazolidin-2-on-1-yl, 3-(2-hydroxyethyl)imidazolidin 2-on-yl, 5-(methylthiomethyl)oxazolidin-2-on-3-yl, 5-(morpholinomethyl)oxazolidin-2-on-3-yl, 3-(morpholinomethyl)imidazolidine-2,4-dione-1-yl and 3-(dimethylaminoethyl)imidazolidine-2,4-dione-1-yl.

Another aspect of the invention is reflected by compounds of formulas I (Ia and Ib) in which A denotes a nitrile group. These compounds correspond to nitrofurylpyrazole derivatives of formula III

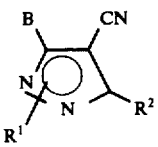 (III)

wherein $R^1$, $R^2$ and B have their previously-ascribed meanings. A more precise representation of this aspect of the invention is provided by formulas IIIa and IIIb

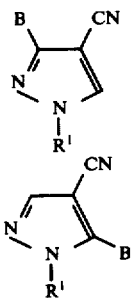

(IIIa)

(IIIb)

in which $R^1$ and B have their previously-noted meanings.

A further aspect of the invention is reflected by compounds of formulas I (Ia and Ib) in which A denotes a free, protected or derived carboxylic acid group. These compounds correspond inter alia, to nitrofurylpyrazole derivatives of formula IV

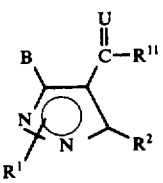 (IV)

in which $R^1$, and $R^2$ and B have their previously-ascribed meanings and

represents a free, protected or derived carboxylic acid group. A more precise representation of compounds of formula IV is provided by formulas IVa and IVb

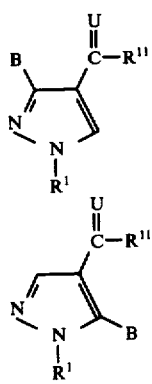

(IVa)

(IVb)

in which $R^1$ and

have their previously-ascribed meanings.

In a free carboxylic acid group

represents a -COOH group. In a protected carboxylic acid group, for example, U represents an oxygen atom and $R^{11}$ represents alkoxy with from 1 to 11 (more particularly, 1 to 4) carbon atoms, aryloxy with up to 12 carbon atoms (chiefly phenoxy) or aralkoxy with up to 14 carbon atoms (chiefly benzyloxy, 1-phenethoxy or 2-phenethoxy). In derived carboxylic acid groups $R^{11}$ denotes, inter alia, a halogen atom (chiefly a chlorine or bromine atom); acyloxy (resulting in a symmetrical or a mixed acid anhydride); mercapto; an azido group; an

group in which each of $R^{12}$ and $R^{13}$ is, independently, a hydrogen atom (—H), alkyl (obtionally substituted by —OH) with from 1 to 7 (particularly from 1 to 4) carbon atoms, or $R^{12}$ and $R^{13}$ (together with the nitrogen atom to which both are bound) denote a heterocyclic radical, e.g. pyrrolidino, piperidino or morpholino; substituted or (preferably) unsubstituted hydroxylamino; a substituted or (preferably) unsubstituted hydrazino group

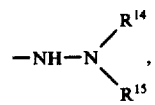

in which each of $R^{14}$ and $R^{15}$, independently, has one of the meanings given for $R^7$ and $R^8$. In a protected or derived carboxylic acid group U, in addition to the preferred meaning as an oxygen atom, is optionally a sulfur atom or one of the groups =NH, =N—$R^3$, =N—O—$R^4$ or =N—N$R^7{}_2$.

Preferred nitrofurylpyrazoles of formula II are compounds II* or isomers II*a and II*b, in which $R^1$ and B have their previously-ascribed meanings and X denotes oxo =O, oximino =N—O—$R^4$ or hydrazono

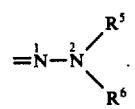

In the formulas II*, II*a and II*b $R^4$, $R^5$, $R^6$, $R^7$, $R^8$, $R^9$, $R^{10}$ and Z have the respective meanings provided for formula II; the following meanings are preferred: $R^4$ is preferably a hydrogen atom (—H) or alkanoyl with from 1 to 4 carbon atoms (more particulaly a hydrogen atom). $R^5$ is preferably a hydrogen atom or straight-chained or branch-chained alkyl with from 1 to 3 carbon atoms (more particularly methyl). $R^6$ is preferably alkyl with from 1 to 3 carbon atoms (more particularly methyl), optionally-substituted (once or twice) phenyl or, more particularly, a mono- or binuclear oxygen-, sulfur- and/or nitrogen-containing heteroaryl group with five- or six-membered rings (more particularly pyridyl, pyrazinyl, 3-pyridazinyl, 2-benzimidazolyl, 2-benzthiazolyl, quinolyl, 2-thiazolyl or 1,3-dimethyl-4-uracilyl), acyl $R^9$—CO— or $R^{10}$—O—CO— {in which $R^9$ is straight-chained or branched-chained alkyl [with from 1 to 4 (more particularly 1 to 2) carbon atoms and optionally substituted with methoxy, ethoxy, dimethylamino, morpholino, pyrrolidino, piperazino of 4-methylpiperazino], unsubstituted phenyl, phenyl which is substituted optionally by 1 to 2 methyl, methoxy, ethoxy, nitro, chloro or bromo substituents, or pyridyl, and $R^{10}$ denotes straight-chained or branch-chained alkyl [with from 1 to 4 carbon atoms and which is optionally substituted (preferably with methoxy or ethoxy)]}, or

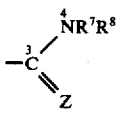

[in which each of $R^7$ and $R^8$ is, independently a hydrogen atom (—H) or methyl and Z denotes an oxygen atom or a sulfur atom]. A heterocyclic radical

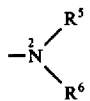

is preferably morpholino or imidazolidine-2,4-dion-1-yl.

Selected nitrofurylpyrazoles of formulas II and II* are compounds II and their isomers, IIa and II**b, in which $R^1$ and B have their previously-ascribed meaning and X represents an oxygen atom =0, hydroxyimino =N—O—$R^4$ or acylhydrazono, e.g. =N—N-H—C(=O)—CH$_3$ or, preferably =N—NH—C(=O)OR$^{10}$ [in which $R^{10}$ denotes a straight-chained or branch-chained alkyl with from 1 to 4 carbon atoms (preferably ethyl)].

Preferred nitrofurylpyrazoles of formula IV are compounds IV* and their isomers IV*a and IV*b, in which $R^1$ and B have their previously-ascribed meanings, U is =O and $R^{11}$ denotes a hydroxy group, or more particularly, an amide group

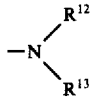

in which each of $R^{12}$ and $R^{13}$, independently, represents straight-chained alkyl (optionally substituted by —OH) with from 1 to 4 carbon atoms or, more particularly, a hydrogen atom.

Preferred nitrofurylpyrazoles of formulas I, II, II*, II**, III, IV and IV* in which A, B, X, U $R^{11}$ have their previously-ascribed meanings, are characterized by the following structural limitations: $R^1$ denotes a denotes a hydrogen atom (—H), straight-chained or branch-chained alkyl with from 1 to 4 (preferably with 1 or 2) carbon atoms [and optionally substituted (preferably) in the 2-position by hydroxy (—OH), methoxy, ethoxy, or acetoxy], unsubstituted or singly-substituted (e.g. by halo, preferably by chloro and, more especially, in the p-position benzyl, allyl, unsubstituted or singly- or doubly-substituted phenyl [preferably in the p-position with halo (for example fluoro, chloro and bromo), methyl, methoxy, trifluoromethyl or nitrol], pyridyl or picolyl (preferably pyridyl); or alkoxycarbonyl (preferably methoxycarbonyl or ethoxycarbonyl).

Especially preferred nitrofurylpyrazoles of formulas I, II, II*, II**, III, IV and IV*, in which A, B, X, U and $R^{11}$ have their previously-given meanings, are characterized by $R^1$ as a hydrogen atom, methyl, phenyl, p-fluorophenyl, p-chlorophenyl, pyridyl, methoxycarbonyl or ethoxycarbonyl.

A further selected group of nitrofurylpyrazoles of formulas I, II, II*, II**, III, Iv and IV*, in which A, B, X, U and $R^{11}$ have their previously-noted meanings, are characterized by $R^1$ as a hydrogen atom, alkyl (preferably with 1 or 2 carbon atoms, and, more particularly, methyl), methoxycarbonyl or ethoxycarbonyl.

Other selected nitrofurylpyrazoles of formulas I, II, II*, II**, III, IV and IV*, in which A, B, X, U and $R^{11}$ have their previously-stated meanings. are characterized by $R^1$ as aryl [preferably unsubstituted or singly- or doubly-substituted phenyl, any substitution preferably being in the p-position with halo, methyl or methoxy (more particularly, fluoro or chloro)] or as heteroaryl [preferably pyridyl or picolyl (more particularly, pyridyl)].

Of the preferred compounds the following are illustrative:

3-(5-nitro-2-furyl)-1H-pyrazole-4-carboxaldehyde,
1-methoxycarbonyl-3-(5-nitro-2-furyl)pyrazole-4-carboxaldehyde,
1-methoxycarbonyl-3-(5-nitro-2-furyl)pyrazole-4-carboxyaldehyde-ethyleneactal,
3-(5-2-furyl)-1H-pyrazole-4-carboxyaldehyde-ethyleneacetal,
1-ethoxycarbonyl-3-(5-nitro-2-furyl)pyrazole-4-carboxyaldehyde,
1-methyl-3-(5-nitro-2-furyl)pyrazole-4-carboxaldehyde,
1-methyl-5-(5-nitro-2-furyl)pyrazole-4-carboxaldehyde,
1-ethyl-3-(5-nitro-2-furyl)pyrazole-4-carboxaldehyde,
1-benzyl-3-(5-nitro-2-furyl)pyrazole-4-carboxaldehyde,
1-allyl-3-(5-nitro-2-furyl)pyrazole-4-carboxaldehyde,
1-isopropyl-3-(5-nitro-2-furyl)pyrazole-4carboxaldehyde,
3-(5-nitro-2-furyl)-1-phenylpyrazole-4-carboxaldehyde,
1-(p-chlorophenyl)-3-(5-nitro-2-furyl)pyrazole-4-carboxaldehyde,
1-(o-chlorophenyl)-3-(5-nitro-2-furyl)pyrazole-4-carboxaldehyde,
1-(m-chlorophenyl)-3-(5-nitro-2-furyl)pyrazole-4-carboxaldehyde,
1-(p-methoxyphenyl)-3-(5-nitro-2-furyl)pyrazole-4-carboxaldehyde,
3-(5-nitro-2-furyl)-1H-pyrazole-4-carboxaldehydeoxime,
1-methyl-3-(5-nitro-2-furyl)pyrazole-4-carboxaldehydeoxime,
1-ethyl-3-(5-nitro-2-furyl)pyrazole-4-carboxaldehydeoxime,
1-isopropyl-3-(5-nitro-2-furyl)pyrazole-4-carboxaldehydeoxime,
1-(o-chlorophenyl)-3-(5-nitro-2-furyl)pyrazole-4-carboxaldehydeoxime,
1-(m-chlorophenyl)-3-(5-nitro-2-furyl)pyrazole-4-carboxaldehydeoxime, 1-(p-chlorophenyl)-3-(5-nitro-2-furyl)pyrazole-4-carboxaldehydeoxime,
3-(5-nitro-2-furyl)-1-phenylpyrazole-4-carboxaldehydeoxime,
1-(p-methoxyphenyl)-3-(5-nitro-2-furyl)pyrazole-4-carboxaldehydeoxime,
1-methyl-3-(5-nitro-2-furyl)pyrazole-4-carboxaldehyde-(O-acetyloxime),
3-(5-nitro-2-furyl)-1H-pyrazole-4-carboxaldehyde-3-pyridylhydrazone,
3-(5-nitro-2-furyl)-1-phenylpyrazole-4-carboxaldehyde-(2-pyridyl)hydrazone,
3-(5-nitro-2-furyl)-1H-pyrazole-4-carboxaldehyde-(2-pyridyl)hydrazone,
1-methyl-3-(5-nitro-2-furyl)pyrazole-4-carboxaldehyde-(2-pyridyl)hydrazone,
1-methyl-5-(5-nitro-2-nitro-2-furyl)pyrazole-4-carboxaldehyde-(2-pyridyl)hydrazone, 3-(5-nitro-2-furyl)-1H-pyrazole 4-carboxaldehyde-methyl-(2-pyridyl)-hydrazone,
3-(5-nitro-2-furyl)-1H-pyrazole-4-carboxaldehyde-benzoylhydrazone,
3-(5-nitro-2-furyl)-1H-pyrazole-4-carboxaldehyde-methoxycarbonylhydrazone,
3-(5-nitro-2-furyl)-1H-pyrazole-4-carboxaldehyde-ethoxycarbonylhydrazone,
1-methyl-3-(5-nitro-2-furyl)pyrazole-4-carboxaldehyde-acetylhydrazone,
3-(5-nitro-2-furyl)-1-phenylpyrazole-4-carboxaldehyde-acetylhydrazone,
1-methyl-3-(5-nitro-2-furyl)pyrazole-4-carboxaldehyde-benzoylhydrazone,
1-methyl-3-(5-nitro-2-furyl)pyrazole-4-carboxaldehyde-isonicotinoylhydrazone,
1-methyl-3-(5-nitro-2-furyl)pyrazole-4-carboxaldehyde-methoxycarbonylhydrazone,
1-methyl-3-(5-nitro-2-furyl)pyrazole-4-carboxaldehyde-4-methylsemicarbazone,
3-(5-nitro-2-furyl)-1-phenylpyrazole-4-carboxaldehyde-isonicotinoylhydrazone,
1-ethyl-3-(5-nitro-2-furyl)pyrazole-4-carboxaldehyde-ethoxycarbonylhydrazone,
1-isopropyl-3-(5-nitro-2-furyl)pyrazole-4-carboxaldehyde-ethoxycarbonylhydrazone,
1-allyl-3-(5-nitro-2-furyl)pyrazole-4-carboxaldehyde-ethoxycarbonylhydrazone,
1-benzyl-3-(5-nitro-2-furyl)pyrazole-4-carboxaldehyde-ethoxycarbonylhydrazone,
1-(p-chlorophenyl)-3-(5-nitro-2-furyl)pyrazole-4-carboxaldehyde-ethoxycarbonylhydrazone,
1-(m-chlorophenyl)-3-(5-nitro-2-furyl)pyrazole-4-carboxaldehyde-ethoxylcarbonylhydrazone,
1-(o-chlorophenyl)-3-(5-nitro-2-furyl)pyrazole-4-carboxaldehyde-ethoxycarbonylhydrazone,
1-(p-methoxyphenyl)-3-(5-nitro-2-furyl)pyrazole-4-carboxaldehyde-ethoxycarbonylhydrazone,
1-[1-methyl-3-(5-nitro-2-furyl)pyrazole-4-ylmethyleneamino]hydantoin,
1-[3-(5-nitro-2-furyl)-1-phenylpyrazole-4-ylmethyleneamino]hydantoin,
3-(5-nitro-2-furyl)-1H-pyrazole-4-carbonitrile,
1-methyl-5-(5-nitro-2-furyl)pyrazole-4-carbonitrile,
1-ethyl-3-(5-nitro-2-furyl)pyrazole-4-carbonitrile,
1-isopropyl-3-(5-nitro-2-furyl)pyrazole-4-carbonitrile,
3-(5-nitro-2-furyl)-1-phenylpyrazole-4-carbonitrile,
1-(o-chlorophenyl)-3-(5-nitro-2-furyl)pyrazole-4-carbonitrile,
1-(m-chlorophenyl)-3-(5-nitro-2-furyl)pyrazole-4-carbonitrile,
1-(p-chlorophenyl)-3-(5nitro-2-furyl)pyrazole-4-carbonitrile,
1-(p-methoxyphenyl)-3-(5-nitro-2-furyl)pyrazole-4-carbonitrile,
1-methyl-3-(5-nitro-2-furyl)pyrazole-4-carboxamide,
1-ethyl-3-(5-nitro-2-furyl)pyrazole-4-carboxamide,
1-isopropyl-3-(5-nitro-2-furyl)pyrazole-4-carboxamide,
1-(o-chlorophenyl)-3-(5-nitro-2-furyl)pyrazole-4-carboxamide,
1-(m-chlorophenyl)-3-(5-nitro-2-furyl)pyrazole-4-carboxamide,
1-cyclohexyl-3-(5-nitro-2-furyl)pyrazole-4-carboxaldehyde,
1-(p-fluorophenyl)-3-(5-nitro-2-furyl)pyrazole-4-carboxaldehyde,
1-(p-bromophenyl)-3-(5-nitro-2-furyl)pyrazole-4-carboxaldehyde,
3-(5-nitro-2-furyl)-1-(p-nitrophenyl)pyrazole-4-carboxaldehyde,
3-(5-nitro-2-furyl)-1-(m-nitrophenyl)pyrazole-4-carboxaldehyde,
3-(5-nitro-2-furyl)-1-(p-tolyl)pyrazole-4-carboxaldehyde,
1-(3,4-dichlorophenyl-3-(5-nitro-2-furyl)pyrazole-4-carboxaldehyde,
1-(3-chloro-p-tolyl)-3-(5-nitro-2-furyl)pyrazole-4-carboxaldehyde,
1-(α,α,α-trifluoro-m-tolyl)-3-(5-nitro-2-furyl)pyrazole-4-carboxaldehyde,
3-(5-nitro-2-furyl)-1-(2-pyridyl)pyrazole-4-carboxaldehyde,
3-(5-nitro-2-furyl)-1-(3-pyridyl)pyrazole-4-carboxaldehyde,
1-allyl-3-(5-nitro-2-furyl)pyrazole-4-carboxaldehydeoxime,
1-benzyl-3-(5-nitro-2-furyl)pyrazole-4-carboxaldehydeoxime,
1-(p-fluorophenyl)-3-(5-nitro-2-furyl)pyrazole-4-carboxaldehydeoxime,
1-(p-bromophenyl)-3-(5-nitro-2-furyl)pyrazole-4-carboxaldehydeoxime,
3-(5-nitro-2-furyl)-1-)p-nitrophenyl)pryazole-4-carboxaldehydeoxime,
3-(5-nitro-2-furyl)-1-(m-nitrophenyl)pyrazole-4-carboxaldehydeoxime,
3-(5-nitro-2-furyl)-1-(p-tolyl)pyrazole-4-carboxaldehydeoxime,
1-(3,4-dichlorophenyl)3-(5-nitro-2-furyl)pyrazole-4-carboxaldehydeoxime,
1-(3-chloro-p-tolyl)-3-(5-nitro-2-furyl)pyrazole-4-carboxaldehydeoxime,
1-(α,α,α-trifluoro-m-tolyl)-3-(5-nitro-2-furyl)pyrazole-4-carboxaldehydeoxime,
3-(5-nitro-2-furyl)-1-(2-pyridyl)pyrazole-4-carboxaldehydeoxime,
3-(5-nitro-2-furyl)-1-(3pyridyl)pyrazole-4-carboxaldehydeoxime,
1-(p-fluorophenyl)-3-(5-nitro-2-furyl)pyrazole-4-carboxaldehyde-ethoxycarbonylhydrazone,
1-(p-bromophenyl)-3-(5-nitro-2-furyl)pyrazole-4-carboxaldehyde-ethoxycarbonylhydrazone,
3-(5-nitro-2-furyl)-1-(p-nitrophenyl)pyrazole-4-carboxaldehyde-ethoxycarbonylhydrazone,
3-(5-nitro-2-furyl)-1-(m-nitrophenyl)pyrazole-4-carboxaldehyde-ethoxycarbonylhydrazone, 1-(3,4-dichlorophenyl)-3-(5-nitro-2-furyl)pyrazole-4-carboxaldehyde-ethoxycarbonylhydrazone,
3-(5-nitro-2-furyl)-1-(p-tolyl)pyrazole-4-carboxaldehyde-ethoxycarbonylhydrazone,
1-(3-chloro-p-tolyl)-3-(5-nitro-2-furyl)pyrazole-4-carboxaldehyde-ethoxycarbonylhydrazone,
1-(α,α,α-trifluoro-m-tolyl)-3-(5-nitro-2-furyl)pyrazole-4-carboxaldehyde-ethoxycarbonylhydrazone,
3-(5-nitro-2-furyl)-1-(2-pyridyl)pyrazole-4-carboxaldehyde-ethoxycarbonylhydrazone,
3-(5-nitro-2-furyl)-1-(3-pyridyl)pyrazole-4-carboxaldehyde-ethoxycarbonylhydrazone,
1-allyl-3-(5-nitro-2-furyl)pyrazole-4-carbonitrile,
1-benzyl-3-(5-nitro-2-furyl)pyrazole-4-carbonitrile,
1-(p-fluorophenyl)-3-(5-nitro-2-furyl)pyrazole-4-carbonitrile,
1-(p-bromophenyl)-3-(5-nitro-2-furyl)pyrazole-4-carbonitrile,
3-(5-nitro-2-furyl)-1-(p-nitrophenyl)pyrazole-4-carbonitrile,
3-(5-nitro-2-furyl)-1-(m-nitrophenyl)pyrazole-4-carbonitrile,
3-(5-nitro-2-furyl)-1-(p-tolyl)pyrazole-4-carbonitrile,
1-(3,4-dichlorophenyl)-3-(5-nitro-2-furyl)pyrazole-4-carbonitrile,
1-(3-chloro-p-tolyl)-3-(5-nitro-2-furyl)pyrazole-4-carbonitrile,
1-(α,α,α-trifluoro-m-tolyl)-3-(5-nitro-2-furyl)pyrazole-4-carbonitrile,
3-(5-nitro-2-furyl)-1-(2-pyridyl)pyrazole-4-carbonitrile,
3-(5-nitro-2-furyl)-1-(3-pyridyl)pyrazole-4-carbonitrile,
1-allyl-3-(5-nitro-2-furyl)pyrazole-4-carboxamide,
1-)p-bromophenyl)-3-(5-nitro-2-furyl)pyrazole-4-carboxamide,
3-(5-nitro-2-furyl)-1-(p-nitrophenyl)pyrazole-4-carboxamide,
3-(5-nitro-2-furyl)-1-(m-nitrophenyl)pyrazole-4-carboxamide,
3-(5-nitro-2-furyl)-1-(p-tolyl)pyrazole-4-carboxamide,
1-(3,4-dichlorophenyl)-3-(5-nitro-2-furyl)pyrazole-4-carboxamide,
1-(3-chloro-p-toly)-3-(5-nitro-2-furyl)pyrazole-4-carboxamide,
1-(α,α,α-trifluoro-m-tolyl)-3-(5-nitro-2-furyl)pyrazole-4-carboxamide,
3-(5-nitro-2-furyl)-1-(3-pyridyl)pyrazole-4-carboxamide,
3-(5-nitro-2-furyl)-1-phenylpyrazole-4-carboxylic acid,
3-(5-nitro-2-furyl)-1-phenylpyrazole-4-carboxylic acid chloride,
phenyl-[3-(5-nitro-2-furyl)-1-phenylpyrazole]carboxylate,
N-methyl-3-(5-nitro-2-furyl)-1-phenylpyrazole-4-carboxamide,
N,N-dimethyl-3-(5-nitro-2-furyl)-1-phenylpyrazole-4-carboxamide,
N-n-butyl-3-(5-nitro-2-furyl)-1-phenylpyrazole-4-carboxamide,
N-(2-hydroxyethyl)-3-(5-nitro-2-furyl)-1-phenylpyrazole-4-carboxamide,
N,N-bis-(2-hydroxyethyl)-3-(5-nitro-2-furyl)-1-phenylpyrazole-4-carboxamide, .
3-(5-nitro-2-furyl)-1,N-diphenylpyrazole-4-carboxamide,
4-[3-(5-nitro-2-furyl)-1-phenyl-4-pyrazolcarbonyl]morpholine,
1-[3-(5-nitro-2-furyl)-1-phenyl-4-pyrazolylcarbonyl-piperidine,
1-[b3-(5-nitro-2-furyl)-1-phenyl-4-pyrazolylcabonyl]-pyrrolidine.

The following are of particular note:

1-methyl-3-(5-nitro-2-furyl)pyrazole-4-carboxaldehyde-ethoxycarbonylhydrazone,
3-(5-nitro-2-furyl)-1-phenylpyrazole-4-carboxaldehyde-ethoxycarbonylhydrazone,
1-methyl-3-(5-nitro-2-furyl)pyrazole-4-carbonitrile,
1-methyl-5-(5-nitro-2-furyl)pyrazole-4-carboxamide,
3-(5-nitro-2-furyl)-1-phenylpyrazole-4-carboxamide,
1-(p-chlorophenyl)-3-(5-nitro-2-furyl)pyrazole-4-carboxamide,
3-(5-nitro-2-furyl)-1-(2-pyridyl)pyrazole-4-carboxamide,
1-(p-fluorophenyl)-3-(5-nitro-2-furyl)-pyrazole-4-carboxamide.

The subject matter of the invention further comprises a method for producing the nitrofurylpyrazoles of formula I

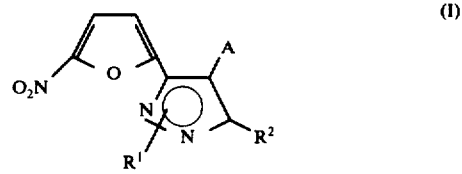

(I)

in which $R^1$, $R^2$ and A have their stated meanings.

The method is characterized as follows:

(a) a nitrofurylpyrazole methylammonium salt of formula V

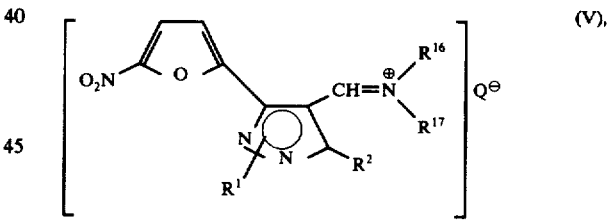

(V), in which $R^1$ and $R^2$ have their previously-noted meanings and in which each of $R^{16}$ and $R^{17}$ is, independently, a hydrogen atom, straight-chained or branch-chained alkyl with from 1 to 5 carbon atoms (preferably methyl), and $R^{17}$ is, optionally, also a cycloalkyl radical with from 3 to 6 carbon atoms, or unsubstituted phenyl or phenyl optionally substituted by alkyl with from 1 to 4 carbon atoms (preferably methyl); alternatively, $R^{16}$ and $R^{17}$ jointly are alkylene with from 4 to 6 (preferably 5) carbon atoms, e.g. pentamethylene, or in which a methylene group is optionally replaced by a heteroatom, such as oxygen or sulfur, or by $=N-R^{18}$, in which $R^{18}$ is alkyl (preferably with from 1 to 3 carbon atoms), i.e. with the formation of a 3-aza-, 3-thia- or, preferably, 3-oxapentamethylene, and $Q^-$ denotes an equivalent of an anion of an organic or inorganic acid, is lyolized or (b) a furylpyrazole of formula VI

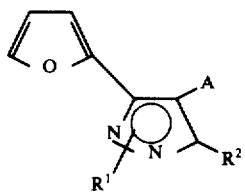
(VI), in which $R^1$, $R^2$ and A have their previously-ascribed meanings, in nitrated or (c) a substituted methyl-nitrofurylpyrazole of formula VII

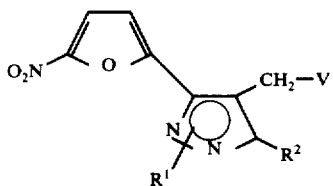
(VII)

in which $R^1$ and $R^2$ have their previously-noted meaning and V is halgon (preferably chloro or bromo), a hydroxy or an amino group, is oxidized or dehydrogenated.

According to the desired meaning of A, the compounds obtained from (a) to (c) are then optionally lyolized and/or alkylated or acylated and/or dehydrated and/or oxidized or, respectively, dehydrogenated.

The lyolysis in accordance with (a) is carried out with compounds WH in which W denotes respectively a substituted oxygen or sulfur atom with two bonds or a nitrogen atom with three bonds, that is with —OH, —SH or —NH compounds, generally according known methods. Water and alcohols are illustrative of —OH, while —SH compounds include, e.g., hydrogen sulfide and thiols, Exemplary —NH compounds are ammonia, primary and secondary amines, hydroxylamines and hydrazines.

The lyolysis of compounds V with water is generally effected at temperatures between —20° and 100° C without or with the addition of an organic solvent, for example an alcohol (such as ethanol), an amide (such as dimethylformamide), a carboxylic acid (such as acetic acid), a ketone (such as acetone), an ether (such as dioxane), a nitrile (such as acetonitrile), or a chlorinated hydrocarbon (such as methylene chloride) in weakly alkaline or, preferably, neutral to strongly acidic conditions; the reaction takes from 0.2 to 8 hours and leads to compounds of formula I in which A is a free aldehyde group; that is to compounds of formula II in which X is an oxygen atom. According to a preferred embodiment the reaction mixture, as obtained in the production of 4-pyrazolylmethyleneammonium compounds V, e.g., by a Vilsmeier or Duff reaction, is stirred into ice, adjusted (if necessary) in pH to from 2 to 7 and subjected to lyolysis which is completed by heating to 15° to 50° C to precipitate aldehydes of formula II.

The lyolysis of compounds of formula V with alcohols is generally brought about by reaction with corresponding alcohols, optionally while heating and/or with the addition of suitable alkali metal alcoholates and/or in the presence of inert solvents and leads to compounds of formula I in which A represents a protected aldehyde in the form of an open-chained or ring acetal.

The lyolysis of compounds of formula V with carbon disulfide or, respectively, thiols or their salts with inorganic or organic bases is, if appropriate, carried out in an organic solvent, such as pyridine, dimethylformamide or alcohol, and/or under pressure at temperatures of 0° C to 120° C and leads to compounds of the general formula I, in which A denotes a derived aldehyde group in the form of a thioaldehyde group; that is, compounds of formula Ii in which X denotes a sulfur atom, preferably in the form of their polymers and, respectively, compounds I in which A denotes a protected aldehyde group in the form of a mercaptal.

The lyolysis of compounds of formula V with amino compounds $H_2N$—$R^{19}$ (in which $R^{19}$ represents a hydrogen atom or one of —$R^3$, —O—$R^4$ or

in which $R^3$, $R^4$, $R^5$ and $R^6$ have their previously-designated meanings) leads to compounds of formula I (in which A represents a derived aldehyde group), that is compounds of formula II (in which X denotes =NH, =N—$R^3$, =N—O—$R^4$ or

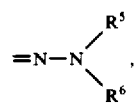

in which $R^3$, $R^4$,$R^5$ and $R^6$ have their previously-noted meanings). Lyolysis with ammonia or amines, $H_2N$—$R^3$, is carried out with equivalent or excess quantities of amino compound at temperatures between —40° C and 120° C, optionally in inert solvent and/or under pressure and/or with equivalent quantities of strong base, such as sodium amide, sodium hydride or potassium tert.-butylate. -butylate.

Lyolysis with a hydroxylamine, $H_2N$—O—$R^4$, or a hydrazine,

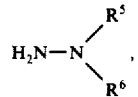

is performed with equivalent or, preferbly, 1- to 1.2-mole excess of amino compounds at from 0° to 120° C, and preferably from 15° to 90° C (preferably) in organic solvent, e.g. an amide (such as dimethylformamide or N-methylpyrrolidone), dimethylsulfoxide or alcohol (such as methanol, ethanol or 2-methoxyethanol), optionally also in admixture with water and/or a proton donor, preferably a lower alkanoic aicd, such as acetic acid, which optionally is released by the addition of a corresponding carboxylic acid salt. Lyolysis with a secondary amine, amino alcohol or diamine leads to a compound of formula I, in which A represents a protected aldehyde group, for example, in the form of an aminal, an oxazolidine or imidazolidine.

Nitration of method (b) is carried out according to known procedures. The nitration is advantageously effected under mild conditions, for example at a low temperature, such as for −30° to 40° C, and under substantially anhydrous conditions, such as with fuming nitric acid and in 95 to 100% sulfuric acid, or in an organic solvent, such as acetic acid, acetic anhydride, chloroform or admixutures thereof, the operation being carried out by stirring into ice. Method (b) is particularly suitable for preparing compounds of formula VI, in which A is a radical (preferably aldehyde, hydroxyimino, acylhydrazono, nitrile or carbamoyl)which cannot be nitrated and is resistant to the nitrating mixture, and $R^1$ represents a radical which is difficult to nitrate, for example a hydrogen atom, lower alkoxycarbonyl, lower alkyl or pyridyl (in other cases compouns of the formula I are chiefly produced with an additional nitro group in substituent $R^1$).

The reaction of method (c) is carried out with reagents or in a manner known to those skilled in the art. The oxidation of compounds of formula VII, in which V is a halogen atom, is effected, for example, by heating with 15 to 20% aqueous copper or lead nitrate solutions, by Sommelet's reaction (with hexamethylenetetramine and subsequent hydrolysis with acid, for example 50% acetic acid) or by heating with selenium dioxide, for example, in nitrobenzene, and leads to compounds of formula I in which A is a free aldehyde group. In another embodiment a halogen compound of formula VII (V = halogen) is reacted with an aromatic amine, for example aniline, and then oxidized in aqueous suspension or solution, for example, with dichromate/sulfuric acid or permanganate in aqueous-acetonic solution at temperatures of from 0° to 20° C. The halogen compounds of formula VII (V = halogen) are optionally first converted into corresponding hydroxy compounds of formula VII (V = OH) by saponification, for example with dilute potassium carbonate solution, and then, as explained below, oxidized.

The oxidation of compounds of formula VII, in which V is an amino group, is carried out, for example, by reaction with potassium permanganate in acetone at low temperatures or by dehydrogenation, for example with isatin or alloxan, with subsequent hydrolysis of the imine formed as an intermediate, and leads to compounds of formula I in whcih A is a free aldehyde group. In accord with a further embodiment an amino compound of the formula VII (V = $NH_2$) is reacted with an aromatic compounds, which has an easily exchanged halogen atom, for example 4-nitro-chlorobenzene-2-sulfonic acid or 2,4-dinitrochlorobenzene, the resulting secondary amines are dehydrogenated to form Schiff bases, for example with dichromate/sulfuric acid or permanganate, and the latter is then hydrolyzed with acid to a compound of formula I in which A is a free aldehyde. The dehydrogenation of compounds of formula VII, in which V is a hydroxy group, is carried out with the assistance of a conventional mild oxidizing agent, for example manganese dioxide in dilute sulfuric acid, activated manganese dioxide in organic solvent (such as petroleum ether, acetone or carbon tetrachloride, optionally also at an elevated temperature), dichromate/sulfuric acid or nitric acid at a low temperature or by catalytic removal of hydrogen, for example in the presence of a copper, silver or zinc compound. In a further embodiment of the invention dehydrogenation is carried out in contact with a hydrogen acceptor, for example chloranil, in toluene or dimethylformamide, or by oxidation with lead dioxide or lead tetraacetate, for example, in a benzene solution with pyridine or by oxidizing reduction in contact with an aldehyde or ketone, for example, in accordance with the method of Oppenauer, compounds of formula I in which A is a free aldehyde group being obtained. The further oxidation of such aldehyde, for example, with hydrogen peroxide and alkali at room temperature, with permanganate and pyridine or with silver oxide leads to compounds of formula I in which A is a free carboxylic acid. Another embodiment of the invention yields such compounds by direct oxidation of compounds of formula VII (in which V denotes a hydroxy group), for example by reaction with dichromate/sulfuric acid in water, optionally with a solution promoter, such as dimethylformamide, potassium permanganate and hydrochloric acid in acetone, or nitric acid, optionally at a raised temperature.

The steps (lyolysis and/or alkylation and/or acylation and/or dehydration and/or oxidation and/or dehydrogenation) which optionally (if necessary) follow the parts of methods (a) to (c) are carried out according to known and established procedures, for example those described in Houben-Weyl, "Methoden der organischen Chemie", 4th edition, Georg-Thieme-Verlag, Stuttgart; I.T. Harrison, S. Harrison, "compendium of Organic Synthetic Methods", Wiley-Interscience (1971); C. A. Buehler, D. E. Pearson, "Survey of Organic Synthesis", Wiley-Interscience (1970); S. R. Sandler, W. Karo, "Organic Functional Group Preparations", Vol. 1 (1968), 2 (1971) and 3 (1972), Academic Press, N.Y. and London.

Thus the lyolysis is carried out with suitable materials, for example WH compounds in which W has the previously-mentioned meaning or acid anhydrides, optionally with a catalyst and/or activator and/or inorganic solvent. Lyolysis of compounds II (in which CH=X represents a protected or derived aldehyde group) with water and inorganic or organic acid, for example hydrochloric acid, sulfuric acid, p-toluenesulfonic acid, at room temperature or at a raised temperature leads to compounds of formula II in which A denotes a free aldehyde group; the lyolysis of acetals, e.g., is carried out with dilute hydrochloric acid while that of oximes and hydrazines is carried out with 65% sulfuric acid. Lyolysis with water of compounds III in contact with a base, for example sodium hydroxide solution or, preferably, an acid, for example hydrochloric acid or sulfuric acid (or Lewis acid, for example boron trifluoride without organic solvent, for example in concentrated sulfuric acid), preferably at room temperature or with an organic solvent, for example an alcohol, methylene chloride or acetic acid, optionally with a copper catalyst and/or an activator, for example ammonium nitrate or sodium nitrate, or, in another embodiment, for example, in sodium hydroxide solution and hydrogen peroxide, leads to compounds of formula I in which A is carbamoyl and of formula IV in which —C(=U)$R^{11}$ is a —C(=O)$NH_2$ group. Under similar reaction conditions, for example at a raised temperature and/or in the case of a prolonged reaction time, lyolysis of nitriles of formula III (via their amides of formula IV) leads to compounds of formula I in which A represents a free carboxyl group When compounds IV (in which —C(=U)$R^{11}$ denotes a protected or derived carboxylic acid group) are subjected to lyolysis with water under alkaline, acidic or neutral conditions, compounds I (in which A represents a free carboxyl group) are obtained; when the lyolysis is incomplete, a stable intermediate stage of formula IV results. Thus, reactive derivatives of formula IV (in which —C(=U)$R^{11}$ denotes, for example, thioamide, imide acid ester or an amidine), are lyolized under mild conditions with water to form amides of formula IV in which —C(=U)R¹¹ represents a carbamoyl group. Lyolysis with water is favored by intermediate formation of reactive intermediate stages, for example, in the case of reacting an amide of formula IV (in which —C(=U)R¹¹ denotes a carbamoyl group) with nitrous acid in a medium containing acetic acid and/or sulfuric acid and with water. The lyolysis of compounds of the formula I (in which R¹ denotes an acyl group) with water, praticularly with a basic catalyst, such as ammonia, organic amines or alkali metal hydroxide, leads to compounds of formula I in which R¹ denotes a hydrogen atom. When compounds of formula I (in which A denotes a free aldehyde group) are subjected to lyolysis with alcohols, compounds of formula I, in which A is a protected aldehyde group in the form of an open-chained or ring acetal, are obtained. This lyolysis is, for example, carried out with alkanols or alkanediols, such as alcohols, e.g. methanol, ethanol, propanol, n-butanol, ehyleneglycol, propyleneglycol and 2,2-dimethyl-1,3-propanediol and acidic catalysts, such as p-toluene sulfonic acid, perchloric acid, hydrochloric acid or Lewis acids, and the water produced is removed, if necessary, by azeotropic distillation, for example, by means of chloroform or benzene. Lyolysis with alcohols is also carried out with corresponding orthoesters, for example orthoformic acid esters, with the help of acidic catalysts, such as mineral acids, ammonium chloride or pyridine hydrochloride. When lyolysis of compounds of formula III is carried out with alcohols, for example while cooling in the presence of hydrogen chloride, compounds of formula I in which A is a derived carboxylic acid group in the form of an alkyl carboximidate hydrochloride are obtained. Compounds of formula I, in which A represents a free or reactive derived carboxylic acid group, are lyolyzed with alcohols to compounds of the formula I in which A represents a protected carboxylic acid group. Examples of such lyolysis include: the azeotropic or extractive reaction of a free acid of formula I (A = COOH) with excess alcohol, R²⁰ —OH, in which R²⁰ represents alkyl with from 1 to 11 (chiefly 1 to 4) carbon atoms or aralkyl with up to 14 carbon atoms, primarily benzyl or phenethyl, in contact with a proton donor; reaction of the preceding components at room temperature in contact with dicyclohexylcarbodiimide; reaction of an acid halide or acid anhydride of formula I (A = —CO—R¹¹), in which R¹¹ denotes a halogen atom or an acyloxy group, respectively, with an alcohol, R²⁰—OH, in which R²⁰ has its previously-mentioned meaning or aryl with up to 12 carbon atoms, primarily phenyl, either with or without a basic condensing agent, such as pyridine, triethylamine or an alkali metal hydroxide. Lyolysis of a compound of formula II (in which X denotes an oxygen atom) with hydrogen sulfide in an organic solvent with an acidic catalyst, for example hydrogen chloride or zinc chloride, leads to derivatives of the formula II (in which X is a sulfur atom) in the form of their polymers, preferably trimers. Lyolysis of compounds of formula III with hydrogen sulfide or a thiol, such as an alkylmercaptan or thioacetic acid (if necessary with an inorganic or organic base, for example pyridine, and/or inert solvent and/or under pressure and/or at a raised temperature) leads to compunds of formula IV, in which —C(=U)R¹¹ represents a thioamide group or an iminothioether group. Lyolysis of compounds of formula I, in which A denotes a free aldehyde group, with a thiol, such as methylmercaptan, ethylmercaptan and ethane-1,2-dithiol, and optionally with an acidic catalyst, such as hydrogen chloride or zinc chloride, leads to protected aldehydes in the form of their open-chained or ring mercaptals. Lyolysis of compounds of formula IV, in which —C(=U)R¹¹ represents a halocarbonyl or an acyloxycarbonyl, with hydrogen sulfide, a thiol or a salt of either with an inorganic or organic base leads to compounds of formula IV in which —C(=U)R¹¹ represents a mercaptocarbonyl or thiocarbonic ester. Lyolysis of compounds of formula I, in which A represents a free aldehyde group or acetal, with a secondary amine or amino alcohol, for example ethanolamine or diamine, for example N,N'-dimethylethylenediamine, optionally with a proton donor, leads to compounds of formula I, in which A represents a protected aldehyde group, for example in the form of an animal, an oxazolidine or an imidazolidine; while lyolysis with ammonia or an amine, H₂N—R³, leads to compounds of formula I, in which A denotes the group —CH=NH or —CH=N—R³; in the latter case optional use is made of inert solvent, which also acts as an entraining agent for azeotropic removal of water, and/or raised temperatures. Lyolysis of compounds of formula I, in which A represents a free aldehyde group, a protected aldehyde group (for example in the form of an acetal, mercaptal, aminal, oxazolidine or similar derivatives) or a reactive derived aldehyde group (for example —CH=S, —CH=NH or —CH=•N—R³) with an amino compound, H₂N—O—R⁴ or

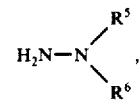

in which each of R³, R⁴, R⁵ and R⁶ has its previously-ascribed meaning, leads to derived alehydes of formula II in which X represents =N—O—R⁴ or

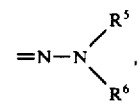

in which R⁴, R⁵ and R⁶ have their previously given meanings. The lyolysis is carried out with equivalent or excess (preferably 1 to 1.2 moles per mole of aldehyde) of amino compound at −10° to 120° C, preferably 15° to 90° C, preferably with organic solvent, for example an amide (such as dimethylformamide or N-methylpyrrolidone), dimethylsulfoxide, an alcohol (such as methanol, ethanol or 2-ethoxyethanol) and, optionally, also with water and/or, preferably, a proton donor, more especially a carboxylic acid, such as acetic acid. Lyolysis of compounds of formula IV [in which —C(=U)R¹¹ denotes a carboxylic acid group which is free (R¹¹ is in this case a hydroxy group), is (preferably) protected (R¹¹ is, for example, an alkyloxy or aryloxy group) or is reactive and derived (R¹¹, for example, has the meaning of a halogen atom, acyloxy, alkylmercapto or azido), with the previously-mentioned meaning for U] with an amino compound,

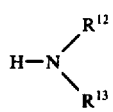

or $H_2NR^3$, $H_2N-O-R^4$,

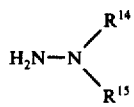

or $H_2N-NR^7_2$, leads to a corresponding compound of formula I in which A represents a derived carboxylic acid group $-C(=U)R^{11}$, in which U and $R^{11}$ have the meanings given for formula IV. Thus, for example, protected carboxylic acid derivatives, such as esters, of formula IV are reacted with the noted amino compounds with or without a solvent, optionally (if required) at a raised temperature, for example at 50° to 150° C, and/or at a raised pressure, to form amides, hydroxamic acids or hydrazides. Compounds of formula IV, in which $-C(=U)R^{11}$ represents a halocarbonyl or haloimidoyl group, are reacted in an aqueous or organic medium with two equivalents of amino compounds or with one equivalent of amino compound in the presence of an auxiliary base, for example an alkali metal hydroxide, pyridine or triethylamine, at from 0° to 30° C to form amides, hydroxamic acids, hydrazides, amidines, N-hydroxyamidines or hydrazidines, and further reacted with sodium azide to form azides, for example. Lyolysis of the free carboxylic acids of formula I with amino compounds and dicyclohexylcarbodiimide at room temperature in a suitable solvent also leads to corresponding carboxylic acid derivatives of formula IV.

The alkylation or acylation, which optionally follows, is carried out by methods known to those skilled in the art. Thus, for example, compounds of formula I in which $R^1$ is hydrogen atom are reacted with an alkylating or acylating reagent, $R^1Q$, in which $R^1$ denotes an aliphatic or alicyclic hydrocarbon radical, an aralkyl group or an acyl radical in accordance with the definitions for $R^1$, and Q denotes the radical or residue of an inorganic or organic acid, for example a halogen atom or an alkylsulfonyloxy or p-tolylsulfonyloxy group, at temperatures between −30° C to 100° C and preferably between −20° C to 60° C, and (if necessary) in a solvent, for example an aromatic hydrocarbon, an alcohol or an aprotic dipolar solvent, such as dimethylformamide, N-methylpyrrolidone or dimethylsulfoxide, and preferably with a basic condensing agent, for example an alkali metal or alkaline earth metal hydroxide, hydride, amide or carbonate, or with an organic nitrogen base, for example pyridine or triethylamine, in which case the alkylating agent is in a molar quantity equal to from 1 to 1.2 times the molar quantity of the substrate. In a similar manner reacting compounds of formula II in which X denotes $=N-OH$ with compounds, $R^4Q$, in which Q has the previously-noted meaning, and $R^4$ denotes an acyl group with the meaning given therefor in formula II, yields compounds of formula II in which X represents $=N-O-R^4$ (with the last-noted meaning of acyl for $R^4$).

The following optional dehydration, which is employed on compounds of formula I in which A denotes the group $-CH=N-OH$ or $-C(=O)NH_2$, is carried out in a conventional manner, for example by heating or by suitable dehydrating materials, optionally in the presence of inert solvent and/or at raised temperature, and leads to compounds of formula I in formula III form. Exemplary dehydrating agents include: glacial acetic acid, acetoanhydride/sodium acetate or formic acid/sodiumformate at a raised temperature; an acyl halide optionally with pyridine; thionyl chloride, phosphorus oxychloride, phosphorus pentachloride, optionally with dimethylformamide; phosgene, p-toluenesulfonic chloride, dicyclohexylcarbodiimide, optionally with organic base; phosphorus pentoxide; dichlorocarbene with a phase transfer catalyst; an isocyanate with a tertiary amine, 1,1'-carbonylbiimidazole; and trichloroacetonitrile. The reaction is optionally also carried out heterogeneously, for example with thionyl chloride in carbon tetrachloride as a solvent. Unstable intermediate stages are optionally isolated in some cases, for example in the case of the reaction of oximes with acid anhydride O-acyloximes or with methyl isocyanate O-methylcarbamoyloximes.

The optionally-ensuing oxidation ot dehydrogenation of compounds of formula 1, in which A denotes a free or derived aldehyde group, is carried out in accord with conventional methods, as in the case of method (c). Thus for example, reacting a free aldehyde of formula II with ammonia and manganese dioxide at a raised temperature yields, via aldimines formed as intermediates, the nitriles of formula III while a similar reaction with amines, $HNR^{12}R^{13}$, and manganese dioxide in the presence of a sodium cyanide yields compounds of formula IV in which $-C(=U)R^{11}$ denotes the group

in which each of $R^{12}$ and $R^{13}$ have its previously-stated meaning (with exception of hydroxyalkyl).

The production of 4-pyrazolylmethyleneammonium compounds V to be used in method (a), is carried out in various different ways. Thus, for example, in a conventional manner by reaction of 5-nitro-2-acetylfuran with the corresponding hydrazines, $H_2N-NH-R^1$, 5-nitro-2-acetylfuranhydrazones are obtained. Reacting these with a Vilsmeier reagent (which is produced from a dialkyl or alkylarylformamide and an acid halide before the reaction or preferably in situ during the reaction) yields 3- or 5-(5-nitro-2-furyl)pyrazole-4-ylmethyleneammonium compounds V. The compounds V are, however, also obtained by reaction of 3- or 5-(5-nitro-2-furyl)pyrazoles with a Vilsmeier reagent. A further method for producing compounds V resides, for example, in reacting 3- or 5-(5-nitro-2-furyl)pyrazoles with hexamethylenetetramine and trifluoroacetic acid in inert solvent, using the method of Duff.

It is surprising that compounds V are also obtained in a single vessel method by reacting 5-nitro-2-acetylfuran with corresponding hydrazines, $H_2N-NH-R^1$, in a medium containing a lower alkanoic acid, for example formic acid, propionic acid, butyric acid and (preferably) acetic acid, and thereafter adding a Vilsmeier reagent. In this method it is preferred to react 5-nitro-2-acetylfuran with approximately one mole equivalent of a hydrazine in a dialkyl or alkylarylformamide containing, for example, glacial acetic acid and following this with an acid halide. Exemplary dialkylformamides include diethylformamide, diisopropylformamide, N-formylpiperidine, N-formylpiperazine, or N-formylmorpholine, but preferably dimethylformamide. Suitable alkylarylformamides comprise, for example, N-methyl-N-phenylformamide and N-ethyl-N-tolylformamide. Illustrative acid halides are phosphorus oxybromide, phosgen, thionyl chloride, but preferably phosphorus oxychloride. This method leads to excellent yields providing the reaction is appropriately carried out. The reaction temperatures generally lie between 10° to 50° C, and the reaction times lie between 30 minutes and 24 hours.

The production of furylpyrazole compounds VI to be used in method (b) is in accord with conventional pyrazole syntheses. Thus, for example, furylpyrazoles VI are obtained from corresponding β-diketones or their functional derivatives and hydrazines, as is described, inter alia, in the German Offenlegungsschrift No. 1,809,387 or are obtained by reaction of 2-acetylfuran-hydrazones with Vilsmeier reagents.

The production of (5-nitro-2-furyl)pyrazole compounds VII for method (c) is also in accord with conventional methods. Thus, for example, 4-halomethylpyrazoles VII are obtained by halomethylation of corresponding pyrazoles which are not substituted in the 4-position. The 4-halomethylpyrazoles VII are converted with water into the corresponding 4-hydroxymethylpyrazoles VII which, with amines, are converted into the corresponding 4-aminomethylpyrazoles VII.
*) 4-Hydroxymethyl-pyrazoles VII are obtained from the corresponding pyrazole-carboxylic acids by reduction with complexed aluminium hydrides, and 4-halogenmethyl pyrazoles are obtained by reaction of 4-hydroxymethyl pyrazoles with acid halides, such as thionylchloride or phosphorus oxychloride.

In accordance with a preferred optional measure compounds of formula II, in which X denotes an oxygen atom, are reacted in a single vessel method, that is to say in a single stage method, to form compounds of formula III. In this case aldehydes II are first reacted with hydroxylamine, which preferably has been released from its acid addition salts with salts of carboxylic acids, for example alkali-metal acetates, in suitable solvent, for example dialkylformamide or arylalkylformamide, preferably dimethylformamide, in medium containing a proton donor, preferably alkanoic acid, such as acetic acid, and then reacted with a dehydrating agent, for example an acid halide, preferable phosphorus oxychloride. The reaction temperatures generally lie between 10° and 50° C while the reaction times lie between 30 minutes and 24 hours, preferably 2 to 8 hours.

The compounds of this invention are thus prepared as hereinbefore presented from available starting materials or from reactants which are obtained by conventional processes from known starting materials.

The new compounds of formula I, II, III and IV have valuable properties which make them commercially significant. On the one hand the compounds of formula I have strong anti-microbial properties, more particularly in the form of an anti-bacterial, anti-protozoal, anti-helminthic or anti-mycotic efficacy; on the other hand they can be converted into other compounds of formula I and therefore constitute valuable intermediates for the production of anti-microbially effective compounds of formulas I, II, III and IV.

The anti-bacterial efficacy of the compounds in accordance with the invention covers both Gram-positive and Gram-negative bacteria. Examples of such bacteria include: Micrococcaceae, for example *Staphilococcus aureus; Streptococcaceae,* for example *Streptococcus pyogenes, S. faecalis* (Enterococcus); Enterobacteriaceae, for example Escherichiae, *E. coli,* Klebsiellae, as *K. pneumoniae,* Proteus, as *P. morgagnii, P. mirabilis, P. Rettgeri,* Salmonellae, as *S. typhimutium, S. enteritidis,* Shigella; Pseudomonaceae, as *Pseudomonas aeruginosa;* Corynebacteriaceae, as *Corynebacterium pyogenes;* Bacillaceae, as *Bacillus subtilis;* Clostridiae; *Mycobacterium tuberculosis.* As protozoa the following are exemplary: Trichomonads, more particularly *Trichomonas vaginalis* and *T. foetus;* Amoebae, such as *Entamoeba histolytica;* Coccidia, such as Eimeria; Plasmodiae; Trypanosomes, like *T. brucei, T. rhodesiense, T. gambiense, T. cruzi;* Leishmaniae. The following mycetes are also merely illustrative: Yeasts, moulds, dermatophytes and dimorphic fungi. Helminths, such as Trematodes, Cestodes and Nematodes, are also subject to the anti-microbial efficacy of the subject compounds, which retard or preclude the growth of proliferation of these organisms.

The excellent and broad spectrum anti-microbial efficacy of the nitrofurylpyrazoles of formula I makes them useful both in human and in veterinary medicine. They are useful both for prophylaxis against infections and also for treatment of infections which already affect an organism.

As indications for use in human medicine there are both internal and external infections, such as general infections, infections of the urogenital system or of the intestinal tract, infections of the mouth and pharynx, bacterially caused dermatoses, for example pyodermias, abcesses, wound infections, infections of the mucous membranes or for disinfection of healty skin and also for the disinfection of wounds.

As indications for use in veterinary medicine there are also external and internal infections, such as infections of the mucous membranes, pyodermias, abcesses, septic wounds, mastidides, infections of the urogenital system and of the intestinal tract, which are subject to treatment with these compounds. As a matter of principle the new compounds are useful for the treatment of all higher members of the animal kingdom and, more particularly, young or adult domestic and farm animals, for example poultry (such as chicks), cats, dogs, rabbits, sheep, pigs, horses and cattle.

The new compounds are also useful as superficial disinfectants. They are likewise useful for the protection of high-molecular weight, hydrophobic or other organic materials or medicinal preparations in order to prevent microbial decomposition; they are thus useful as preserving agents by mixture, bringing into contact, impregnation of an organic material with the compounds, or in some other fashion. The new compounds are also useful as growth-promoting additives for animal feedstuffs. For the several noted uses the compounds are applied in the same manner of previously-known counterparts having similar utility.

The compounds of formula I, in accordance with the type of substitution, involve an anti-microbial spectrum of action with different centers of gravity whereby one of the cited effects, more particularly the anti-bacterial effect (particularly, for example, against the courses of general, urogenital or intestinal infections or external infections) or the anti-protozoal (especially against trichomonad infections) effect or a combination of these effects is emphasized. In accordance with the desired therapeutic effect or one of the mentioned uses one of the compounds of formula I of the desired type of effect is used.

The superior anti-microbial efficacy of compounds of formula I is confirmed by tests in vitro and in vivo, using standard methods, whereby the efficacy of known active substances, for example that of nitrofurantoin, nifuroxazide, nifuratel or metronidazol, was clearly exceeded.

The invention also relates to an anti-microbially effective agent for combatting the courses of human and animal diseases, chacterized by its containing one or more of the new active substances of formulas I, II, III or IV.

The anti-microbially effective agents are produced in accordance with known methods. As medicaments, the new compounds are used as such or, optionally, in combination with suitable pharmaceutical vehicles. If the novel pharmaceutical preparations contain pharmaceutical vehicles in addition to the active substances, the content of active substance of such mixtures comprises 0.1 to 99.5, preferably 0.5 to 95, percent by weight of the overall mixture.

In accordance with the invention the active substances are used in any desired form in human and veterinary fields, for example systematically or topically under the proviso that the formation or maintenance of sufficient antimicrobial blood, secretion or tissue levels or local concentrations of nitrofuryl compounds is ensured. This is achieved either by oral, rectal or parenteral administration in suitable doses. The new medicaments are, however, also administerable intravaginally or locally on the body surface. Advantageously, a pharmaceutical preparation of active substance is provided in the form of uniform doses, which are made up in accordance with the desired administration. A uniform or unit dose is, for example, a tablet, coated pill, a capsule, a suppository, a vaginal ball, a vaginal tablet or a vaginal rod or a measured volumetric quantity of a powder, a granulate, a solution, an emulsion, a suspension, a sol, a gel, an ointment or a cream.

The term "unit dosis" within the meaning of the present invention is understood to mean a physically determined unit, which comprises an individual quantity of the active component in combination with a pharmaceutical vehicle, the content of active substance in the dose being a fraction or a multiple of a therapeutic individual dose. An individual dose preferably comprises the quantity of active substance which is administered in one application and generally amounts to a whole daily dose or to half, a third or a quarter of a daily dose. If, for an individual therapeutic administration, only a fraction, such as a half or a quarter, of the uniform dose is required, the uniform dose is advantageously arranged to be capable of being split, for example in the form of a tablet with a notch for breaking it.

The pharmaceutical preparations in accordance with the invention comprise, when they are provided in the form of uniform doses and for applications, for example on human patients, approximately from 2 to 6000 mg, advantageously from 10 to 2500 mg and, more particularly from 20 to 1200 mg of active substance.

In general it has been found advantageous both in human and also in veterinary medicine to administer the active substance or substances in the case of oral administration in a daily dose of approximately 0.1 to approximately 50, preferably 0.5 to 20 and more particularly 1 to 10, mg/kg of body weight and, if necessary, in the form of several, preferably 1 to 3, individual doses for obtaining the desired results. An individual dose comprises the active substance or substances in quantities between approximately 0.05 and approximately 25, preferably 0.25 to 15 and more particularly 0.5 to 10, mg/kg of body weight per day.

In the case of a parenteral treatment, for example intraperitoneal, similar doses are employed. In the case of mastitis therapy of cows approximately 5 to approximately 500 mg of active substance are applied for each quarter of the udder.

For a local application it is possible to use preparations which comprise approximately 0.01 to approximately 10, preferably 0.05 to 5 and more particularly 0.1 to 1, percent by weight of active substance.

The therapeutic administration of the pharmaceutical preparation is carried out 1 to 4 times daily at fixed times or variable times, for example after the respective meals and/or in the evening. It can, however, be necessary to depart from the above-mentioned doses in accordance with the type, the body weight and the age of the patient being treated, the type and severity of the disease, the type of the preparation and the application of the medicament and the period of time or interval, within which the administration occurs. Thus in some cases it may be sufficient to make use of a quantity of active substance less than that specified, while in other cases the quantities of active substance must be exceeded. The determination of the optimum dosing necessary in each particular case and the type of application of active substances is readily effected by anyone skilled in the art on the basis of his expert knowledge.

The pharmaceutical preparations consist, as a rule, of the active substances (a compound of formula I) in accordance with the invention and nontoxic, pharmaceutically-compatible medicament vehicles, which are used as an admixture or diluent in a solid, semisolid or liquid form or as a casing material, for example in the form of a capsule, a tablet coating, a sachet or another container, for the therapeutically-active component. A vehicle serves, for example, as a means for promoting introduction of the medicament into the body, as an adjuvant for making up a particular prescription, as a sweetening agent, as a substance for changing the flavor, as a dye or as a preserving agent.

Suitable forms for oral administration include tablets, coated pills, hard and soft capsules, for example gelatine, dispersible powders, granulates, aqueous and oily suspensions, emulsions, solutions or syrups.

Tablets comprise inert diluents, for example calcium carbonate, calcium phosphate, sodium phosphate or lactose; granulating and distributing agents, for example maize starch or alginate; binding agents, for example starch, gelatine or gum acacia; and lubricants, such as aluminum or magnesium stearate, talcum or silicone oil. They are optionally additionally provided with a coating made up, e.g., so that it brings about delayed dissolving and resorption of the medicament in the gastrointestinal tract and thus achieves, for example, improved compatibility, protraction or retardation. Gelatin capsules comprise the medicament, e.g., mixed with a solid diluent, for example calcium carbonate or kaolin, or with an oily diluent, for example olive or ground nut oil or liquid paraffin.

Aqueous suspensions comprise, e.g., suspending agents, such as sodium carboxymethylcellulose, methylcellulose, hydroxypropylcellulose, sodium alginate, polyvinylpyrrolidone, gum tragacanth or gum acacia; dispersing and wetting agents, such as polyoxyethylene stearate, heptadecaethyleneoxycetanol, polyoxyethylenesorbitol monooleate, polyoxyethylenesorbitane monooleate or lecithin; preserving agents, such as methyl or propylhydroxybenzoates; flavoring agents; and sweetening agents, such as saccharose, lactose, sodium cyclamate, dextrose, invert sugar syrup.

Oily suspensions comprise, for example, ground nut oil, olive oil, sesame oil, cocoanut oil and liquid paraffin, and thickening agents, for example beeswax, paraffin wax or cetyl alcohol; and, optionally, sweetening agents, flavoring agents and antioxidants.

Powders and granulates, which are dispersible in water, comprise the medicaments, e.g., mixed with dispersing, wetting and suspending agents, such as those hereinbefore mentioned, and sweetening agents, flavoring agents and dyes.

Emulsions comprise, for example, olive oil, ground nut oil or liquid paraffin in addition to emulsifying agents, such as gum acacia, gum tragacanth, phosphatides, sorbitan monooleate and polyoxyethylenesorbitan monooleate as well as sweetening and flavoring materials.

For rectal administration suppositories of the medicaments are useful. These are produced with the help of binding agents, for example cocoa butter and polyethyleneglycols, which fuse at the rectal temperature.

For parenteral administration of the medicaments it is possible to use sterile aqueous suspensions adapted for injection, isotonic salt solutions or other solutions, which can comprise dispersing or wetting agents and/or pharmacologically-compatible diluents, for example propylene or butyleneglycol.

Ointments, pastes, creams, gels, sols, vaginal tablets or rods, e.g., suitable for local treatment, comprise, in addition to the active substance or substances, the conventional vehicles, for example animal and plant fats, waxes, liquid paraffin and paraffin wax, starch, gum tragacanth, cellulose derivatives, polyethyleneglycols, silicones, bentonites, silicic acid, talcum and zinc oxide or mixtures of these materials.

Powders and sprays comprise, in addition to a microbially-effective concentration of one or more active substances of formula I, e.g., the conventional vehicles, for example lactose, talcum, silicic acid, aluminum hydroxide, calcium silicate and polyamide powder or mixtures of these substances. Sprays optionally additionally comprise conventional propellants, for example chlorofluorohydrocarbons. They are applied directly to microorganisms, to areas to be disinfected or to areas to be kept free from microbial contamination.

For infections of the mouth and pharynx alcoholic solutions with from 1 to 5% by weight of active substance (a compound of formula I), and other vehicles, or tablets (which dissolve in the mouth) with from 0.2 to 20% by weight of active substance of formula I, sugar and further vehicles are useful.

The active substance or substances are optionally also furnished in a micro-capsule form with one or more of the noted vehicles.

In addition to the novel nitrofurylpyrazole compounds the pharmaceutical preparations optionally comprise one or more pharmacologically-active components from other groups of medicinal substances, for example steroids, such as oestrogens, e.g. oestradiol benzoate or valerianate, or corticoids, e.g. hydrocortisone; sulfonamides, e.g. sulfanilamide or 6-sulfanilamide-2,4-dimethylpyrimidine; antibiotics, such as penicillins, e.g. penicillin G or ampicillin; cephalosporins, e.g. cephalosporin C; or saccaride antibiotics, e.g. streptomycins, kanamycins or neomycins; or polyene antibiotics, for example nystatin, pimaricin or amphotericin B; or tetracyclines, e.g. Aureomycin ® or Terramycin ®; peptide antibiotics, e.g. bacitracin, chloramphenicol or rifamycins; nitroheterocycles, e.g. nitrothiazoles (niridazole); nitrofurans (nitrofurantoin); or nitropyrimidines (2-amino-5-nitropyrimidine); antimycotics, for example phenolcarboxylic acids (o-hydroxybenzoic acid or p-hydroxybenzoic acid alkyl ester); 8-hydroxyquinolines, e.g. 5-chloro-8-hydroxy-7-iodoquinoline or 5,7-dichloro-2-methyl-8-hydroxyquinoline; 3,4',5-tribromosalicylanilide or other halogenated salicylanilides, halogenated carbanilides, halogenated benzoxazoles or benzoxazolones, polychlorohydroxydiphenylmethanes, halodihydroxydiphenylsulfides, 4,4'-dichloro-2-hydroxydiphenylethers, 2',4,4'-trichloro-2-hydroxydiphenylethers or other polyhalohydroxydiphenylethers or bactericidal quarternary compounds.

The compounds of formula I are optionally used as feedstuff additives for promoting growth and for improving foodstuff utilization in animal breeding, especially in breeding of young animals, such as calves, piglets, chickens and turkeys, and in fattening cattle, such as oxes and cows, pigs, ets.

In this case the administration of the active substance or substances is conveniently via foodstuff and/or drinking water. The active substances are, however, alternatively administered in feedstuffs in the form of concentrates and in preparations comprising vitamins and/or mineral salts.

The new compounds are administered in feedstuff or in drinking water in a concentration between approximately 0.1 and approximately 1000, preferably between 1 and 200 and, more particularly between 20 and 100 ppm by weight.

The mixture with feedstuff optionally in the form of a premix (for example active substance of formula I and wheat flour) or feedstuff concentrate and the remaining feedstuff preparation is carried out according to conventional methods.

A further part of the invention is comprised by a method for the chemotherapy of vertebrates, for example mammals or birds, which is characterized by administering to an infected animal an anti-microbially-effective and pharmacologically-compatible quantity of one or more compounds of formulas I, II, III or IV.

The intermediate products of formulas I, II, III or IV are converted in accordance with the previously-described methods into anti-microbial compounds of formula I, as further illustrated in the following examples. Thus, from the free aldehydes of formula II the aldehyde derivatives of formula II, in which A denotes a protected or derived aldehyde, for example the acetals, the imines, the oximes or the hydrazones, are obtained; in just the same manner the protected and derived aldehydes are converted into free aldehydes. The protected aldehyde derivatives are furthermore employed for the production of the derived aldehydes. The free aldehydes of formula II also serve as starting products for the production of compounds of formula III or formula IV. Nitriles III are employed for producing compounds of formula IV. Compounds of formula I, in which A represents a protected or derived carboxylic acid group, are convertible into corresponding compounds in which A denotes a free carboxylic acid group; in just the same manner compounds IV with a protected carboxylic acid group are convertible into compounds of formula IV in which A denotes a derived carboxylic acid group. Furthermore, compounds of formula IV in which A represents a free carboxylic acid group are useful for the production of compounds IV in which A denotes a protected or derived carboxylic acid group. Oximes of formula II and amides of formula IV are useful for producing corresponding compounds of formula III. Compounds of formula I (in which $R^1$ denotes a hydrogen atom) are useful for producing compounds of formula I in which $R^1$ denotes an aliphatic or alicyclic hydrocarbon radical, aralkyl or acyl. Compounds of formula I (in which $R^1$ denotes an acyl radical) are useful for producing compounds of formula I in which $R^1$ denotes a hydrogen atom.

The following examples explain the invention in more detail without restricting it. The abreviations m.p. and b.p. denote the fusing point and, respectively, boiling point.

EXAMPLE 1

3-(5-nitro-2-furyl)-1H-pyrazole-4-carboxaldehyde

Add 27 g of phosphorus oxychloride dropwise to 100 ml of dimethylformamide at 10° to 20° C and then stir for 30 minutes at this temperature. To the obtained Vilsmeier complex add in portions (at 40° C) 17.7 g of 5-nitro-2-acetylfuransemicarbazone. Stir for 30 minutes at this temperature and then heat the mixture for 6 hours at 50° C, observing the formation of gas. Pour the batch (comprising the 4-pyrazolylmethylenedimethylammonium salt) onto 100 g of ice and adjust its pH-value to 6 to 7 by the dropwise addition of 6N caustic soda. Dilute with water and stir for a further 4 hours. Separate the precipitate by vacuum filtration and dry over calcium chloride so as to obtain 7 g of yellow crystals. Shake the mother liquor with three 200-ml portions of chloroform, and then evaporate in vacuo. Heat the residue with 500 ml of water to obtain 3 g of yellow crystals. Mix the combined precipitate with 200 ml of water and 54 ml of sodium hydroxide. Clarify with active charcoal and then precipitate by acidifying with acetic acid to obtain 3-(5-nitro-2-furyl)-1H-pyrazole-4-carboxaldehyde [m.p. 187° to 187.5° C (from o-dichlorobenzene)] with a yield of 21%.

To obtain the semicarbazone used as the starting product stir together 15.5 g of 5-nitro-2-acetylfuran, 12.6 g of semicarbazide hydrochloride and 9 g of anhydrous sodiumacetate for 5 hours at room temperature in ethanol, drawing off and washing with ethanol and water.

Prepare 5-nitro-2-acetylfuran, for example, in accordance with U.S. patent specification 2,976,300 (Norwich), C.A. 55, P 16567b.

EXAMPLE 2

1-methoxycarbonyl-3-(5-nitro-2-furyl)pyrazole-4-carboxaldehyde

Add 444 ml of phosphorus oxychloride dropwise to 603 ml of dimethylformamide at 10° to 20° C to obtain a Vilsmeier complex and, at 15° C add 275 g of 5-nitro-2-acetylfuranmethoxycarbonylhydrazone thereto. Raise the temperature over 5 hours to from 28° to 30° C, and stir at this temperature for 3 to 4 hours. Hydrolyze the thus-produced [1-methoxycarbonyl-3-)5-nitro-2-furyl)-4-pyrazolyl]methylenedimethylammonium salt by pouring it into 2.9 kg of ice and 1.5 l of water while holding the temperature (approximately 1.5 hours) below 25° C by adding ice thereto. Draw off the crystalline precipitate, wash it with water until it is neutral and dry it to obtain 1-methoxycarbonyl-3-(5-nitro-2-furyl)-pyrazole-4-carboxaldehyde [m.p. 187° to 189° C with decomposition (from dimethylformamide/water)] with a yield of 80%.

Prepare 5-nitro-2-acetylfuranmethoxycarbonylhydrazone in the following manner:

Stir 119.5 of 5-nitro-2-acetylfuran and 76.4 g. of carbazinic acid methyl ester in 400 ml. of methanol and 3 ml of glacial acetic acid for 5 hours at 40° C. Cool down the misture to 0° C and then wash it with cold methanol to obtain 169 g. of 5-nitro-2-acetylfuranmethoxycarbonylhydrazone [m.p. 179° to 180° C].

EXAMPLE 3

1-methoxycarbonyl-3-(5-nitro-2-furyl)pyrazole-4-carvoxaldehyde-ethyleneacetal

Heat 464 g of 1-methoxycarbonyl-3-(5-nitro-2-furyl)-pyrazole-4-carboxyaldehyde together with 170 g of ethyleneglycol and 0.6 g of p-toluene sulfonic acid in 3000 ml of chloroform under reflux with a water-removing attachment until no further water is produced (4 to 5 hours). Clarify with acitve charcoal, reduce the bulk in vacuum to dryness and recrystallize from dimethylformamide and water to obtain 1 -methyoxycarbonyl-3-(5-nitro-2-furyl)pyrazole-4-carboxaldehyde-ethyleneacetal [m.p. 178.5° to 179.5° C (dioxan/water)] with a yild of 83%.

In a similar manner prepare from ($a^1$) 1-methyl-3-(5-nitro-2-furyl)pyrazole-4-carboxaldehyde, ($a^2$) 1-ethyl-3-(5-nitro-2-furyl)pyrazole-4carboxaldehyde, ($a^3$) 1-benzyl-3-(5-nitro-2-furyl)pyrazole-4-carboxaldehyde, ($a^4$) 1-(p-chlorophenyl)-3-(5-nitro-2-furyl)pyrazole-4-carboxaldehyde, and ($a^5$) 3-(5-nitro-2-furyl)-1-phenylpyrazole-4-carboxaldehyde and ($b^1$) ethyleneglycol or $b^2$) 2,2-dimethyl-1,3-propanediol each of the following:

($a^1b^1$) 1-methyl-3-(5-nitro-2-furyl)pyrazole-4-carboxaldehyde-ethyleneacetal, ($a^2b^1$) 1-ethyl-3-(5-nitro-2-furyl)pyrazole-4-carboxaldehyde-ethyleneacetal, ($a^3b^1$) 1-benzyl-3-(5-nitro-2-furyl)pyrazole-4carboxaldehyde-ethyleneacetal, ($a^4b^1$) 1-(p-chlorophenyl)-3-(5-nitro-2-furyl)pyrazole-4-carboxaldehyde-ethyleneacdtal, and ($a^5b^1$) 3-(5-nitro-2-furyl)-1-phenylpyrazole-4-carboxaldehyde-ethyleneacetal, respectively, or ($a^1b^2$) 1-methyl-3-(5-nitro-2-furyl)pyrazole-4-carboxaldehyde-2', 2'-dimethylpropyleneacetal, ($a^2b^2$) 1-ethyl-3-(5-nitro-2-furyl)pyrazole-4-carboxaldehyde-2',2'-dimethylpropyleneacetal, ($a^3b^2$) 1-benzyl-3-(5-nitro-2-furyl)pyrazole-4-carboxaledehyde-2',2'-dimethylpropyleneacetal, ($a^4b^2$) 1-(p-chlorophenyl)-3-(5-nitro-2-furyl)pyrazole-4-carboxaldehyde-2',2'-dimethylpropyleneacetal, and ($a^5b^2$) 3-(5-nitro-2-furyl)-1-phenylpyrazole-4-carboxaldehyed-2',2'-dimethylpropyleneacetal, respectively.

EXAMPLE 4

3-(5-nitro-2-furyl)-1H-pyrazole-4-carboxaldehyde-ethyleneaceal

Add 29 ml of concentrated ammonia solution (in 200 ml. of dimethylformamide and 50 ml of water) dropwise at room temperature to a suspension of 51 g of 1-methoxycarbonyl-3-(5-nitro-2-furyl)pyrazole-4-carboxaldehyde-ethyleneacetal. Stir for 20 minutes until dissolution takes place. Acidify with 2N hydrochloric acid to a pH of from 5 to 6 to throw down a precipitate. Add 50 ml of water dropwise, stir for a further 15 minutes at room temperture, draw off the precipitate and wash with water to obtain 3-(5-nitro-2-furyl)-1H-pyrazole-4-carboxaldehyde-ethyleneacetal [m.p. 166° to 167° C]with a yield of 79%.

EXAMPLE 5

3-(5-nitro-2-furyl)-1H-pyrazole-4-carboxaldehyde

Add dropwise 292 ml of a 25% ammonia solution to a suspension of 513 g of 1-methoxycarbonyl-3-(5-nitro-2-furyl)pyrazole-4-carboxaldehyde-ethyleneacetal in 2000 ml of dimethylformamide and 250 ml water at 20° to 25° C within a period of approximately 20 minutes, whereupon the precipitate is dissolved. Then stir for a further 30 minutes. While cooling to a moderate extent, add approximately 1000 ml of 2N hydrochloric acid; a strongly acidic reaction is obtained. Stir for 2 hours at 30° C and add 1.7 kg of ice. Draw off the thrown-down precipitate under cold conditions and wash with water until neutral to obtain 3-(5-nitro-2-furyl)-1H-pyrazole-4-carboxaldehyde [m.p. 187° to 187.5° C]with a yield of 96%.

EXAMPLE 6

3-(5-nitro-2-furyl)-1H-pyrazole-4-carboxaldehyde (a) Add 54 ml of concentrated ammonia solution dropwise to a suspension of 95.5 g of 1-methoxycarbonyl-3-(5-nitro-2-furyl)pyrazole-4-carboxaldehyde-ethyleneacetal in 750 ml of dioxan. Stir the resulting admixture for 12 minutes. Then add thereto 160 ml of 2N hydrochloric acid to adjust its pH to 1. Stir the thus-acidified product for 30 minutes before diluting it with 2000 ml of water. Allow the resulting precipitate to stand overnight in a cooling cupboard to obtain a quantitative yield of 3-(5-nitro-2-furyl)-1H-pyrazole-4-carboxaldehyde with a melting point of 184° to 186° C.

(b) React 3.1 g of 1-methoxycarbonyl-3-(5-nitro-2-furyl)pyrazole-4-carboxaldehyde-ethyleneacetal in 50 ml of dioxan and 25 ml of water with 1.73 g of piperidine for 20 minutes at room temperature (20° C) and then proceed according to the method of part (a) above to obtain 3-(5-nitro-2-furyl)-1H-pyrazole-4-carboxaldehyde with a melting point of 185° to 187° C.

EXAMPLE 7

3-(5-nitro-2-furyl)-1H-pyrazole-4-carboxaldehyde

To a suspension of 9.1 g of 1-methoxycarbonyl-3-(5-nitro-2-furyl)pyrazole-4 -carboxaldehyde in 80 ml of dioxan add dropwise at 5° to 8° C 33.4 ml of concentrated ammonia solution. Stirr the resulting admixture for 15 minutes before acidifying it with 2N hydrochloric acid to a pH value of 2. Distill off the greater part of the dioxan in vacuo. Mix the residue with 100 ml of water. Draw off the precipitate and wash it with water to obtain 3-(5-nitro-2-furyl)-1H-pyrazole-4-carboxaldehyde [melting point: 179° to 185° C] with a yield of 78%.

EXAMPLE 8

1-ethoxycarbonyl-3-(5-nitro-2-furyl)pyrazole-4-carboxaldehyde

Produce a Vilsmeier complex at room temperature from 10 ml of dimethylformamide and 4.7 ml of phosphorusoxychloride. Add 3 g of 5-nitro-2-acetylfuranethoxycarbonylhydrazone thereto at 15° to 17° C and stir the resulting admixture for one day at room temperature. Pour the obtained solution containing 4-pyrazolyl-methylenedimethylammonium salt onto ice and water. Filter off the first precipitate (0.6 g) and allow the filtrate to stand and subsequently yield a precipitate of 49% of 1-ethoxycarbonyl-3-(5-nitro-2-furyl)pyrazole-4-carboxaldehyde [m.p. 139.5° to 141° C (from acetone)].

EXAMPLE 9

3-(5-nitro-2-furyl)-1H-pyrazole-4-carboxaldehyde

Hydrolyze 0.96 g of 1-ethoxycarbonyl-3-(5-nitro-2-furyl)pyrazole-4-carboxaldehyde in 8 ml of dioxan first with 3.3 ml of concentrated ammonia solution and then with hydrochloric acid in a manner similar to that of Example 7 to obtain 3-(5-nitro-2-furyl)-1H-pyrazole-4-carboxaldehyde [m.p. 181° to 186° C] with a yield of 75%.

EXAMPLE 10

1-methyl-3-(5-nitro-2-furyl)pyrazole-4-carboxaldehyde

Add 100 g of 3-(5-nitro-2-furyl)-1H-pyrazole-4-carboxaldehyde at from −15° C to −5° C in the dark and in the absence of air to a suspension of 16.0 g of 80% sodium hydride in 670 ml of dimethylformamide. Stir the resulting admixture for a further 30 minutes before adding thereto (at the same temperature a solution of 75.4 g of methyl iodide in 100 ml of dimethylformamide to produce a precipitate. Stir for a further hour. Add 6 g of glacial acetic acid thereto and then pour the resulting solution onto 1600 g of ice and water. Stir the thus-cooled material for one hour before filtering and wash the obtained precipitate [100.7 g (94.5% of the theoretical value) of a mixture of 1-methyl-3-(5-nitro-2-furyl)-pyrazole-4-carboxaldehyde and 1-methyl-5-(5-nitro-2-furyl)pyrazole-4-carboxaldehyde] with water. Dissolve the precipitate in 300 ml of hot dimethylformamide. Reprecipitate with 150 ml of water, and, then repeat this operation two further times with suitably-reduced quantities of solvent to obtain 1 -methyl-3-(5-nitro-2-furyl)pyrazole-4-carboxaldehyde [m.p. 183° to 184° C] with a yield of 59%.

EXAMPLE 11

1-methyl-5-(5-nitro-2-furyl)pyrazole-4-carboxaldehyde

Reduce in volume under vacuum the combined filtrates from the precipitations in Example 10. Wash the resulting residue thoroughly with water and subject it to column chromatography on silica gel with chloroform/ethanol (9:1) for a yield of 6 g of 1 -methyl-5-(5-nitro-2-furyl)pyrazole-4-carboxaldehyde [m.p. 129.5° to 130° C (from methanol/water)].

EXAMPLE 12

1-methyl-3-(5-nitro-2-furyl)pyrazole-4-carboxaldehyde and
1-methyl-5-(5-nitro-2-furyl)pyrazole-4-carboxaldehyde Produce a Vilsmeier complex from 9 ml of dimethylformamide and 10 g of phosphorus oxychloride at 15° to 20° C, and add thereto 3.0 g of 5-nitro-2-acetylfuran-methylhydrazone at from 10° to 15° C. Stir the resultant for one day at room temperature before adding ice to the thus-produced 4-pyrazolylmethylenedimethylammonium-salt-containing solution. Adjust the pH-value thereof to 2 with caustic soda solution. Then heat for 30 minutes to from 40° to 50° C. Allow to cool, filter and wash the filtrate with water to obtain a 2.4 g of a mixture of the methylated pyrazoles. Chromatograph the mixture on a silica gel column with chloroform/ethanol (19:1) to obtain 1-methyl-3-(5-nitro-2-furyl)pyrazole-4-carboxaldehyde [m.p. 183° to 184° C] and 1-methyl-5-(5-nitro-2-furyl)pyrazole-4-carboxaldehyde [m.p. 129.5° to 130.5° C].

EXAMPLE 13

1-methyl-3-(5-nitro-2-furyl)pyrazole-4-carboxaldehyde

Heat 1.0 g of 1-methyl-3-(5-nitro-2-furyl)pyrazole together with 0.73 g of hexamethylenetetramine and 11.6 g of trifluoroacetic acid for 4.5 hours at boiling point. Add the resulting 4-pyrazolylmethyleneammonium-salt-containing solution to 31 ml of ice water. Stir the thus-obtained admixture for 15 minutes, and make it alkaline with concentrated sodium carbonate solution. Filter off the precipitate and wash it with water until it is neutral to obtain 1-methyl-3-(5-nitro-2-furyl)pyrazole-4-carboxaldehyde [melting point: 181° to 182° C] with a yield of 79%.

Obtain the following in a similar manner from 1-ethyl-3-(5-nitro-2-furyl)pyrazole and, respectively, 1-isopropyl-3-(5-nitro-2-furyl)pyrazole and hexamethylenetetramine and trifluoroacetic acid:

1-ethyl-3-(5-nitro-2-furyl)pyrazole-4-carboxaldehyde [m.p. 144° to 146° C] and, respectively.

1-isopropyl-3-(5-nitro-2-furyl)pyrazole-4-carboxaldehyde [m.p. 167.5° to 169.5° C].

Prepare the starting materials as follows:

Add (dropwise in a darkened vessel under nitrogen at 45° C) a solution of 42 g of triethylamine in 170 ml of vinyl acetate to a suspension of 67 g of 5-nitro-2-furaldehyde-α-bromo-N-methylhydrazone in 335 ml of vinyl acetate. Stir the resulting admixture for a further 2 hours at 60° C and then evaporate it to dryness in vacuo. Stir the residue for 1.5 hours with 150 ml of water and filter to obtain an 83% yield of 1-methyl-3-(5-nitro-2-furyl)pyrazole [m.p. 163° to 164° C (from dimethylformamide/water)]. Similarly from 5-nitro-2-furaldehyde-α-bromo-N-ethylhydrazone and 5-nitro-2-furaldehyde-α-bromo-N-isopropylhydrazone, 1-ethyl-3-(5-nitro-2-furyl)pyrazole and 1-isopropyl-3-(5-nitro-2-furyl)pyrazole, respectively, are obtained.

EXAMPLE 14

1-methyl-3-(5-nitro-2-furyl)pyrazole-4-carboxaldehyde

Produce a Vilsmeier complex from 38 ml of dimethylformamide and 39 g of phosphorus oxychloride, add 10 g of 1-methyl-3-(5-nitro-2-furyl)pyrazole thereto and then heat for 11 hours at 80° to 85° C. Pour the resulting solution containing the 4-pyrazolylmethylenedimethylammonium salt onto ice and stir for 2 hours. Add caustic soda thereto to produce a pH of 3. Vacuum filter while cold to produce 7.4 g of product. Chromatograph the product on a silica gel column with chloroform/ethanol (9:1) and recrystallize from dimethylformamide/water to obtain 1-methyl-3-(5-nitro-2-furyl)pyrazole-4-carboxaldehyde [m.p. 183° to 184.5° C].

EXAMPLE 15

1-ethyl-3-(5-nitro-2-furyl)pyrazole-4-carboxaldehyde
1-ethyl-5-(5-nitro-2-furyl)pyrazole-4-carboxaldehyde Add 10 g of 3-(5-nitro-2-furyl)-1H-pyrazole-4-carboxaldehyde to a suspension of 80% sodium hydride in 50 ml of dimethylformamide at −10° to −12° C. Stir the resulting admixture for 30 minutes and then add a solution of 8.3 g of ethyl iodide in 20 ml of dimethylformamide dropwise thereto at from −5° to −12° C. Stir the thus-prepared reaction mixture for a further 2 to 5 hours at a temperature between −5° C and 0° C before adding 0.5 g of glacial acetic acid thereto. Pour the obtained solution onto 200 g of ice and water, and filter off the produced precipitate under vacuum while cold to obtain 9.3 g of product which also comprises some isomeric 1-ethyl-5-(5-nitro-2-furyl)pyrazole-4-carboxaldehyde. Recrystallize the product three times from dimethylformamide and water to obtain 1-ethyl-3-(5-nitro-2-furyl)pyrazole-4-carboxaldehyde [m.p. 145° to 146° C]. Evaporate the mother liquor and chromatograph the residue on a silica gel column with chloroform/ethanol (9:1) to obtain 1-ethyl-5-(5-nitro-2-furyl)pyrazole-4-carboxaldehyde.

In place of ethyl iodide react 3-(5-nitro-2-furyl)-1H-pyrazole-4-carboxaldehyde in a corresponding manner with each of isoamyl bromide, n-hexyl bromide, benzyl bromide, p-chlorobenzyl chloride, and allyl bromide to obtain 1-isoamyl-3-(5-nitro-2-furyl)pyrazole-4-carboxaldehyde, 1-n-hexyl-3-(5-nitro-2-furyl)pyrazole-4-carboxaldehyde, 1-benzyl-3-(5-nitro-2-furyl)pyrazole-4-carboxaldehyde [m.p. 155° to 157° C], 1-(p-chlorobenzyl)-3-(5-nitro-2-furyl)pyrazole-4-carboxaldehyde, and 1-allyl-3-(5-nitro-2-furyl)pyrazole-4-carboxaldehyde [m.p. 110° to 112° C], respectively, and the corresponding 1-substituted 5-(5-nitro-2-furyl)pyrazole-4-carboxaldehydes.

EXAMPLE 16

1-isopropyl-3-(5-nitro-2-furyl)pyrazole-4-carboxaldehyde

Add 10 g of 3-(5-nitro-2-furyl)-1H-pyrazole-4-carboxaldehyde to a suspension of 1.6 g of 80% sodium hydride in 100 ml of dimethylformamide under nitrogen at 10° to 20° C. Add 7.1 g of isopropyl bromide to the resulting admixture and then stir it for 4 hours at 40° C and 7 hours at 50° C. Mix 0.8 ml of glacial acetic acid therein to obtain (after addition to 190 g of ice and water) 8.9 g of product. Recrystallize three times from dimethylformamide and water to obtain 1-isopropyl-3-(5-nitro-2-furyl)pyrazole-4-carboxaldehyde [m.p. 168.5° to 170.5° C]. Evaporate the mother liquor and chromatograph the residue to obtain 1-isopropyl-5-(5-nitro-2-furyl)pyrazole-4-carboxaldehyde.

Carry out the reaction in a corresponding manner with 5.3 g of 2-chloroethyl-methyl ether (instead of 7.1 g of isopropyl bromide) to obtain 1-(2-methoxyethyl)-3-(5-nitro-2-furyl)pyrazole-4-carboxaldehyde [m.p. 137° to 138° C].

Carry out the reaction in a corresponding manner with 9.4 g of cyclohexyl bromide (instead of 7.1 g of isopropyl bromide) to obtain 1-cyclohexyl-3-(5-nitro-2-furyl)pyrazole-4-carboxaldehyde [m.p. 150.5° to 151° C].

EXAMPLE 17

3-(5-nitro-2-furyl)-1-phenylpyrazole-4-carboxaldehyde

At 10° to 20° C add 77 g of phosphorus oxychloride dropwise to 183 g of dimethylformamide. Stir for 30 minutes at room temperature and, at a temperature not exceeding 40° C, add thereto 55.7 g of 5-nitro-2-acetylfuran-phenylhydrazone. Stir under nitrogen for 1 hour at this temperature and then for 2.5 hours at 50° C. Pour the resulting solution (containing 4-pyrazolylmethylenedimethylammonium salt) onto 2.5 kg of ice and water. Heat for 2 hours at 40° C before vacuum filtering at 20° to 30° C. Wash the residue well with water to obtain a 98% yield of 3-(5-nitro-2-furyl)-1-phenylpyrazole-4-carboxaldehyde [m.p. 208° to 209° C (from dimethylformamide/water)].

Prepare the 5-nitro-2-acetylfuran-phenylhydrazone (m.p. 174° to 175° C with decomposition) starting material by (a) reacting 5-nitro-2-acetylfuran with 1.1 moles of phenylhydrazine and 0.1 mole of glacial acetic acid in ethanol at room temperature or (b) boiling 5-nitro-2-acetylfuran-methoxycarbonylhydrazone with 1.5 moles of phenylhydrazine and 0.1 mole of glacial acetic acid in ethanol for 3 hours under reflux.

EXAMPLE 18

3-(5-nitro-2-furyl)-1-phenylpyrazole-4-carboxaldehyde

Add 0.1 g of glacial acetic acid and 4.0 g of phenylhydrazine to a solution of 5.0 g of 5-nitro-2-acetylfuran in 27 ml of dimethylformamide, the temperature rising slightly. Stir the resulting admixture for 1 hour without heating before clarifying with degased active charcoal and then adding 16.3 g of phosphorus oxychloride to the thus-prepared solution of 5-nitro-2-acetylfuran-phenylhydrazone while cooling with ice at from 10° to 15° C. Stir for a further hour at this temperature and then for 24 hours at room temperature. Pour the solution (containing 4-pyrazolylmethylenedimethylammonium salt) onto ice and water and then heat for 1.5 hours at 40° C before cooling in ice to obtain an 85% yield of 3-(5-nitro-2-furyl)-1-phenylpyrazole-4-carboxaldehyde [m.p. 208° to 209° C (dimethylformamide/water)].

Repeat the reaction in a similar manner while replacing phenylhydrazine with each of:

p-fluorophenylhydrazine,
p-bromophenylhydrazine,
3-chloro-p-tolylhydrazine,
α, α, α-trifluoro-m-tolylhydrazine,
3,4-dichlorophenylhydrazine,
2-naphthylhydrazine,
p-biphenylylhydrazine, and
5-indanylhydrazine to obtain
1-(p-fluorophenyl)-3-(5-nitro-2-furyl)pyrazole-4-carboxaldehyde [m.p. 185° to 186.5° C],
1-(p-bromophenyl)-3-(5-nitro-2-furyl)pyrazole)-4-carboxaldehyde [m.p. 211° to 212° C],
1-(3-chloro-p-tolyl)-3-(5-nitro-2-furyl)pyrazole-4-carboxaldehyde [m.p. 169° to 170° C],
3-(5-nitro-2-furyl)-1-(α,α,α-trifluoro-m-tolyl)pyrazole-4-carboxaldehyde [m.p. 148° to 150° C],
1-(3,4-dichlorophenyl)-3-(5-nitro-2-furyl)pyrazole-4-carboxaldehyde [m.p. 222° to 223° C (with decomposition)],
1-(2-naphthyl)-3-(5-nitro-2-furyl)pyrazole-4-carboxaldehyde,
1-(p-biphenylyl)-3-(5-nitro-2-furyl)pyrazole-4-carboxaldehyde, and
1-(5-indanyl)-3-(5-nitro-2-furyl)pyrazole-4-carboxaldehyde, respectively.

EXAMPLE 19

1-(p-chlorophenyl)-3-(5-nitro-2-furyl)pyrazole-4-carboxaldehyde

Add 37 g of phosphorus oxychloride dropwise to 153 ml of dimethylformamide at from 10° to 20° C. Stir the thus-obtained admixture for 30 minutes at room temperature before adding 18.3 g of 5-nitro-2-acetylfuran-p-chlorophenylhydrazone in portions, thus causing the temperature to rise to 40° C. Stir for 4 additional hours at 40° C and then pour the solution containing the 4-pyrazolylmethylenedimethylammonium salt onto 1 kg of ice and water. Heat the so-cooled solution for 1 hour at 40° C, and then (vacuum) filter it at room temperature. Wash filter residue with water to obtain a 92% yield of 1-(p-chlorophenyl)-3-(5-nitro-2-furyl)pyrazole-4-carboxaldehyde [m.p. 192° to 193° C (from toluene)].

To obtain 5-nitro-2-acetylfuran-p-chlorophenylhydrazone, heat 10.8 g of 5-nitro-2-acetylfuran, 16 g of p-chlorophenylhydrazine sulfate and 6.9 g of sodium acetate in ethanol to boiling for 2 hours. Precipitate with 100 ml of water to produce an aqueous suspension of the precipitate [m.p. 138° to 140° C (with decomposition)].

EXAMPLE 20

Following the procedure of Example 17 and replacing 5-nitro-2-acetylfuran-phenylhydrazone by an equivalent of each of 5-nitro-2-acetylfuran-o-chlorophenylhydrazone [m.p. 124° to 126° C (with decomposition)],
5-nitro-2-acetylfuran-m-chlorophenylhydrazone [m.p. 139° to 141° C (with decompostion)],
5-nitro-2-acetylfuran-p-methoxyphenylhydrazone [m.p. 164.5° to 166° C (with decomposition)],
5-nitro-2-acetylfuran-p-tolylhydrazone [m.p. 150.5° to 152.5° C (with decomposition)],
5-nitro-2-acetylfuran-p-nitrophenylhydrazone [m.p. 228.5° to 230° C (with decomposition)],
5-nitro-2-acetylfuran-m-nitrophenylhydrazone [m.p. 204.5° to 205.5° C (with decomposition)], and
5-nitro-2-acetylfuran-3,4-dimethoxyphenylhydrazone, results in the corresponding preparation of:
1-(o-chlorophenyl)-3-(5-nitro-2-furyl)pyrazole-4-carboxaldehyde [m.p. 158° to 160° C],
1-(m-chlorophenyl)-3-(5-nitro-2-furyl)pyrazole-4-carboxaldehyde [m.p. 164° to 165° C],
1-(p-methoxyphenyl)-3-(5-nitro-2-furyl)pyrazole-4-carboxaldehyde [m.p. 218.5° to 220° C],
3-(5-nitro-2-furyl)-1-(p-tolyl)pyrazole-4-carboxaldehyde [m.p. 186.5° to 187.5° C],
3-(5-nitro-2-furyl)-1-(p-nitrophenyl)pyrazole-4-carboxaldehyde [m.p. 228.5° to 230° C (with decomposition)], 3-(5-nitro-2-furyl)-1-(m-nitrophenyl)pyrazole-4-carboxaldehyde [m.p. 192° to 193° C], and
1-(3,4-dimethoxyphenyl)-3-(5-nitro-2-furyl)pyrazole-4-carboxaldehyde, respectively.

EXAMPLE 21

3-(5-nitro-2-furyl)-1H-pyrazole-4-carboxaldehyde

Add 3 ml of 65% nitric acid dropwise to 11 ml of acetic anhydride at room temperature. Then add 1 drop of concentrated sulfuric acid thereto before stirring for 30 minutes and then incorporating therein 1.5 g of 3-(2-furyl)-1H-pyrazole-4-carboxaldehyde. Stir the resulting admixture for 45 minutes at room temperature before adding 4.8 g of sodium acetate. Heat for 1 hour at 30° C and then for 2 hours at 40° C. Pour the thus-produced solution on ice, neutralize it with concentrated ammonia solution and extract the neutralized solution several times with chloroform. Concentrate by evaporation in vacuum and then chromatograph over a silica gel column with chloroform/ethanol (9:1) to obtain 3-(5-nitro-2-furyl)-1H-pyrazole-4-carboxaldehyde [m.p. 187° to 187.5° C].

To obtain 3-(2-furyl)-1H-pyrazole-4-carboxaldehyde, add 60 g of phosphorus oxychloride dropwise to 50 ml of dimethylformamide at from 10° to 20° C and then, at room temperature, add 18.2 g of 2-acetylfuran-methoxycarbonylhydrazone [m.p. 138° to 139° C] to the resulting admixture. Stir overnight at room temperature and then pour the solution onto ice. Stir for a further 2 hours at room temperature and then separate the precipitate by vacuum filtration. Suspend the precipitate in 50 ml of dioxan, which is made alkaline at 5° C with concentrated ammonia solution. Acidify the resulting solution with hydrochloric acid to obtain the desired product [m.p. 120° to 130.5° C (from dioxan/water)].

EXAMPLE 22

3-(5-nitro-2-furyl)-1H-pyrazole-4-carboxaldehydeoxime

Stir together 18 g of 3-(5-nitro-2-furyl)-1H-pyrazole-4-carboxaldehyde, 6.95 of hydroxylamine hydrochloride and 8.2 g of sodium acetate in 70 ml of water for 1.5 hours at 70° C. Cool the resulting admixture slowly to 0° C. Separate the formed precipitate by vacuum filtration and wash the residue with several portions of ice-cold water to obtain a 97% yield of 3-(5-nitro-2-furyl)-1H-pyrazole-4-carboxaldehydeoxime [m.p. 233° to 235° C (with decomposition)].

Following the same procedure, react 2.5 g of 3-(5-nitro-2-furyl)-1H-pyrazole-4-carboxaldehye ethyleneacetal in a similar manner with 0.9 g of hydroxylamine hydrochloride and 0.8 g of sodium acetate to obtain a 94% yield of 3-(5-nitro-2-furyl)-1H-pyrazole-4-carboxaldehydeoxime.

EXAMPLE 23

Repeating the procedure of Example 22, react (separately) each of:

1-methyl-3-(5-nitro-2-furyl)pyrazole-4-carboxaldehyde,
1-ethyl-3-(5-nitro-2-furyl)pyrazole-4-carboxaldehyde,
1-isopropyl-3-(5-nitro-2-furyl)pyrazole-4-carboxaldehyde,
1-(2-methoxyethyl)-3-(5-furyl)pyrazole-4-carboxaldehyde,
1-(o-chlorophenyl)-3-(5-nitro-2-furyl)pyrazole-4-carboxaldehyde,
1-(m-chlorophenyl)-3-(5-nitro-2-furyl)pyrazole-4-carboxaldehyde, and
1-(p-chlorophenyl)-3-(5-nitro-2-furyl)pyrazole-4-carboxaldehyde with hydroxylamine hydrochloride and sodium acetate to obtain the following:

1-methyl-3-(5-nitro-2-furyl)pyrazole-4-carboxaldehydeoxime [m.p. 227° to 228° C (with decomposition)],
1-ethyl-3-(5-nitro-2-furyl)pyrazole-4-carboxaldehydeoxime [m.p. 189° to 190° C (with decomposition)],
1-isopropyl-3-(5-nitro-2-furyl)pyrazole-4-carboxaldehydeoxime [m.p. 154° to 156° C (with decomposition)],
1-(2-methoxyethyl)-3-(5-nitro-2-furyl)pyrazole-4-carboxaldehydeoxime,
1-(o-chlorophenyl)-3-(5-nitro-2-furyl)pyrazole-4-carboxaldehydeoxime [m.p. 189° to 191° C (with decomposition)],
1-(m-chlorophenyl)-3-(5-nitro-2-furyl)pyrazole-4-carboxaldehydeoxime [m.p. 200° to 201° C (with decomposition)], and
1-(p-chlorophenyl)-3-(5-nitro-2-furyl)pyrazole-4-carboxaldehydeoxime [m.p. 216° to 218° C (with decomposition)], respectively.

EXAMPLE 24

1-methyl-3-(5-nitro-2-furyl)pyrazole-4-carboxaldehydeoxime

Add 20 ml of approximately 2% ammonia solution dropwise to a mixture of 10.0 g of 1-methyl-3-(5-nitro)-pyrazole-4-carboxaldehyde and 3.6 g of hydroxylamine hydrochloride in 100 ml of water while stirring at 60° C so that a pH-value of from 4 to 5 is reached. Heat the resulting admixture for 2 hours at 60° C, and then cool it to room temperature. Vacuum filter and wash the residue with water to obtain a 96% yield of a mixture of the syn- and anti-forms of 1-methyl-3-(5-nitro-2-furyl)-pyrazole-4-carboxaldehydeoxime [m.p. 227° to 228° C (from ethanol)].

EXAMPLE 25

3-(5-nitro-2-furyl)-1-phenylpyrazole-4-carboxaldehydeoxime

Add (while stirring) 7.61 g of sodium acetate and 6.58 g of hydroxylamine hydrochloride to 25.0 g of 3-(5-nitro-2-furyl)-1-phenylpyrazole-4-carboxaldehyde in 75 ml of dimethylformamide, the temperature rising slightly. Stir for a further 45 minutes at from 30° to 35° C and for one hour at room temperature. Clafify with degased active charcoal and then pour the solution onto 1 kg of ice and water. Vacuum filter and wash with water to obtain 98% yield of 3-(5-nitro-2-furyl)-1-phenylpyrazole-4-carboxaldehydeoxime [m.p. 199° to 201° C with decomposition (from toluene)].

EXAMPLE 26

By reaction with hydroxylamine hydrochloride and sodium acetate in a manner similar to that of Example 25 the following:

1-methyl-3-(5-nitro-2-furyl)pyrazole-4-carboxaldehyde,
1-methyl-5-(5-nitro-2-furyl)pyrazole-4-carboxaldehyde, 1-isoamyl-3-(5-nitro-2-furyl)pyrazole-4-carboxaldehyde,
1-n-hexyl-3-(5-nitro-2-furyl)pyrazole-4-carboxaldehyde,
1-benzyl-3-(5-nitro-2-furyl)pyrazole-4-carboxaldehyde,
1(p-chlorobenzyl)-3-(5-nitro-2-furyl)pyrazole-4-carboxaldehyde,
1-allyl-3-(5-nitro-2-furyl)pyrazole-4-carboxaldehyde,
1-cyclohexyl-3-(5-nitro-2-furyl)pyrazole-4-carboxaldehyde,
1-(p-chlorophenyl)-3-(5-nitro-2-furyl)pyrazole-4-carboxaldehyde,
1(p-bromophenyl)-3-(5-nitro-2-furyl)pyrazole-4-carboxaldehyde,
1-(p-fluorophenyl)-3-(5-nitro-2-furyl)pyrazole-4-carboxaldehyde,
1-(p-methoxyphenyl)-3-(5-nitro-2-furyl)pyrazole-4-carboxaldehyde,
3-(5-nitro-2-furyl)-1-(p-tolyl)pyrazole-4-carboxaldehyde,
3-(5-nitro-2-furyl)-1-(p-nitrophenyl)pyrazole-4-carboxaldehyde,
3-(5-nitro-2-furyl)-1-(m-nitrophenyl)pyrazole-4-carboxaldehyde,
3-(5-nitro-2-furyl)-1-($\alpha,\alpha,\alpha$-trifluoro-m-tolyl)pyrazole-4-carboxaldehyde,
1-(3-chloro-p-tolyl)-3-(5-nitro-2-furyl)pyrazole-4-carboxaldehyde,
1-(3,4-dichlorophenyl)-3-(5-nitro-2-furyl)pyrazole-4-carboxaldehyde,
1-(3,4-dimethoxyphenyl)-3-(5-nitro-2-furyl)pyrazole-4-carboxaldehyde, 1-(2-naphthyl-3-(5-nitro-2-furyl)-pyrazole-4-carboxaldehyde,,
1 -(p-biphenylyl)-3-(5-nitro-2-furyl)pyrazole-4-carboxaldehyde, and
1-(5-indanyl)-3-(5-nitro-2-furyl)pyrazole-4-carboxaldehyde yield:
1-methyl-3-(5-nitro-2-furyl)pyrazole-4-carboxaldehydeoxime [m.p. 227° to 228° C (with decomposition)],
1-methyl-5-(5-nitro-2-furyl)pyrazole-4-carboxaldehydeoxime,
1-isoamyl-3-(5-nitro-2-furyl)pyrazole-4-carboxaldehydeoxime,
1-n-hexyl-3-(5-nitro-2-furyl)pyrazole-4-carboxaldehydeoxime.
1-benzyl-3-(5-nitro-2-furyl)pyrazole-4-carboxaldehydeoxime [m.p. 174.5° to 176° C]
1-(p-chlorobenzyl)-3-(5-nitro-2-furyl)pyrazole-4-carboxaldehydeoxime,
1-allyl-3-(5-nitro-2-furyl)pyrazole-4-carboxaldehydeoxime [m.p. 161° to 163° C],
1-cyclohexyl-3-(5-nitro-2-furyl)pyrazole-4-carboxaldehydeoxime,
1-(p-chlorophenyl)-3-(5-nitro-2-furyl)pyrazole-4-carboxaldehydeoxime [m.p. 216° to 218° C (with decomposition)],
1-(p-bromophenyl)-3-(5-nitro-2-furyl)pyrazole-4-carboxaldehydeoxime [m.p. 217° to 218° C (with decomposition)],
1-(p-fluorophenyl)-3-(5-nitro-2-furyl)pyrazole-4-carboxaldehydeoxime [m.p. 202° to 204° C (with decomposition)],
1-(p-methoxyphenyl)-3-(5-nitro-2-furyl)pyrazole-4-carboxaldehydeoxime [m.p. 209° to 210° C (with decomposition)],
3-(5-nitro-2-furyl)-1-(p-tolyl)pyrazole-4-carboxaldehydeoxime [m.p. 211° to 212.5° C],
3-(5-nitro-2-furyl)-1-(p-nitrophenyl)pyrazole-4-carboxaldehydeoxime [m.p. 220.5° to 228° C (with decomposition)],
3-(5-nitro-2-furyl)-1-(m-nitrophenyl)pyrazole-4-carboxaldehydeoxime [m.p. 218° to 219.5° C (with decomposition)],
3-(5-nitro-2-furyl)-1-($\alpha,\alpha,\alpha$-trifluoro-m-tolyl)pyrazole-4-carboxaldehydeoxime,
1-(3-chloro-p-tolyl)-3-(5-nitro-2-furyl)pyrazole-4-carboxaldehydeoxime [m.p. 209° to 209.5° C (with decomposition)],
1-(3,4-dichlorophenyl)-3-(5-nitro-2-furyl)pyrazole-4-carboxaldehydeoxime [m.p. 228° to 230° C (with decomposition)],
1-(3,4-dimethoxyphenyl)-3-(4-nitro-2-furyl)pyrazole-4-carboxaldehydeoxime,
1-(2-naphthyl)-3-(5-nitro-2-furyl)pyrazole-4-carboxaldehydeoxime,
1-(p-biphenylyl)-3-(5-nitro-2-furyl)pyrazole-4-carboxaldehydeoxime, and
1-(5-indanyl)-3-(5-nitro-2-furyl)pyrazole-4-carboxaldehydeoxime, respectively.

EXAMPLE 27

1-methyl-3-(5-nitro-2-furyl)pyrazole-4-carboxaldehyde-(O-acetyloxime)

Stir together 2.5 g of 1-methyl-3-(5-nitro-2-furyl)-pyrazole-4-carboxaldehydeoxime, 1.27 g of acetic anhydride and 10 ml of benzene for 2 hours at from 80° to 85° C. Cool the resulting solution and vacuum filter to obtain 1-methyl-3-(5-nitro-2-furyl)pyrazole-4-carboxaldehyde-(O-acetyloxime) [m.p. 192° to 197° C (with decomposition) from toluene] with a yield of 83%.

By replacing the acetic anhydride with an equivalent of propionic anhydride or butyric anhydride, 1-methyl-3-(5-nitro-2-furyl)pyrazole-4-carboxaldehyde-(O-propionyloxime) or 1-methyl-3-(5-nitro-2-furyl)pyrazole-4-carboxaldehyde-(O-butyryloxime), respectively, is obtained.

Following the same procedure and replacing 1-methyl-3-(5-nitro-2-furyl)pyrazole-4-carboxaldehydeoxime by an equivalent of 1-ethyl-3-(5-nitro-2-furyl)pyrazole-4-carboxaldehydeoxime, 1-isopropyl-3-(5-nitro-2-furyl)pyrazole-4-carboxaldehydeoxime and 3-(5-nitro-2-furyl)-1-phenylpyrazole-4-carboxaldehydeoxime, respectively, results in the corresponding preparation of: 1-ethyl-3-(5-nitro-2-furyl)pyrazole-4-carboxaldehyde-(O-acetyloxime), 1-isopropyl-3-(5-nitro-2-furyl)-pyrazole-4-carboxaldehyde-(O-acetyloxime), and 3-(5-nitro-2-furyl)-1-phenylpyrazole-4-carboxaldehyde-(O-acetyloxime), respectively.

EXAMPLE 28

1-methyl-3-(5-nitro-2-furyl)pyrazole-4-carboxaldehyde-dimethylhydrazone

Stir together 2 g of 1-methyl-3-(5-nitro-2-furyl)-pyrazole-4-carboxaldehyde, 0.65 g of N,N-dimethylhydrazine, 2 drops of glacial acetic acid and 30 ml of ethanol for 4 hours at room temperature. Add 30 ml of water dropwise thereto to obtain a 96% yield of 1-methyl-3-(5-nitro-2-furyl)pyrazole-4-carboxaldehyde-dimethylhydrazone [m.p. 164° to 165° C].

EXAMPLE 29

Following the procedure of Example 28 and replacing the carboxaldehyde with an equivalent of:

3-(5-nitro-2-furyl)-1H-pyrazole-4-carboxaldehyde,
3-(5-nitro-2-furyl)-1-phenylpyrazole-4-carboxaldehyde, and
1-(p-chlorophenyl)-3-(5-nitro-2-furyl)pyrazole-4-carboxaldehyde results in the corresponding preparation of:

3-(5-nitro-2-furyl)-1H-pyrazole-4-carboxaldehyde-dimethylhydrazone [m.p. 162° to 163° C],
3-(5-nitro-2-furyl)-1-phenylpyrazole-4-carboxaldehyde-dimethylhydrazone [m.p. 141° to 143° C (from dimethylformamide/water)], and
1(p-chlorophenyl)3-(5-nitro-2-furyl)pyrazole-4-carboxaldehyde-dimethylhydrazone, respectively.

EXAMPLE 30

Following the procedure of Example 28 and replacing the N,N-dimethylhydrazine with an equivalent of methylhydrazine, phenylhydrazine and p-chlorophenylhydrazine yields 1-methyl-3-(5-nitro-2-furyl)pyrazole-4-carboxaldehyde-methylhydrazone,
1-methyl-3-(5-nitro-2-furyl)pyrazole-4-carboxaldehyde-phenylhydrazone, and
1-methyl-3-(5-nitro-2-furyl)pyrazole-4-carboxaldehyde-(p-chlorophenyl)hydrazone, respectively.

EXAMPLE 31

Following the procedure of Example 28 and similarly reacting equivalent amounts of each of:

3-(5-nitro-2-furyl)-1H-pyrazole-4-carboxaldehyde,
1-methyl-3-(5-nitro-2-furyl)pyrazole-4-carboxaldehyde,
1-(2-methoxyethyl)-3-(5-nitro-2-furyl)pyrazole-4-carboxaldehyde,
3-(5-nitro-2-furyl)-1-phenylpyrazole-4-carboxaldehyde,
1-(p-chlorophenyl)-3-(5-nitro-2-furyl)pyrazole-4-carboxaldehyde,
1-(p-fluorophenyl)-3-(5-nitro-2-furyl)pyrazole-4-carboxaldehyde, and
3-(5-nitro-2-furyl)-1-(p-tolyl)pyrazole-4-carboxaldehyde with 3-hydrazinopyridine results in the corresponding preparation of:

3-(5-nitro-2-furyl)-1H-pyrazole-4-carboxaldehyde-3-pyridylhydrazone [m.p. 237° and higher (with decomposition)],
1-methyl-3-(5-nitro-2-furyl)pyrazole-4-carboxaldehyde-3-pyridylhydrazone,
1-(2-methoxyethyl)-3-(5-nitro-2-furyl)pyrazole-4-carboxaldehyde-3-pyridylhydrazone,
3-(5-nitro-2-furyl)-1-phenylpyrazole-4-carboxaldehyde-3-pyridylhydrazone,
1-(p-chlorophenyl)-3-(5-nitro-2-furyl)pyrazole-4-carboxaldehyde-3-pyridylhydrazone,
1-(p-fluorophenyl)-3-(5-nitro-2-furyl)pyrazole-4-carboxaldehyde-3-pyridylhydrazone, and
3-(5-nitro-2-furyl)-1-(p-tolyl)pyrazole-4-carboxaldehyde-3-pyridylhydrazone, respectively.

EXAMPLE 32

3-(5-nitro-2-furyl)-1-phenylpyrazole-4-carboxaldehyde-(2-pyridyl)hydrazone

Stir an admixture of 2 g of 3-(5-nitro-2-furyl)-1-phenylpyrazole-4-carboxaldehyde, 0.92 g of 2-hydrazinopyridine, 50 ml of ethanol and 2 drops of glacial acetic acid for 36 hours at room temperature. Cool the admixture and then form a precipitate with 50 ml of water to obtain a 95% yield of 3-(5-nitro-2-furyl)-1-phenylpyrazole-4-carboxaldehyde-(2-pyridyl)hydrazone [m.p. 228° to 231° C (with decomposition) from dimethylformamide/water].

Replacing the carboxaldehyde of this example with an equivalent of each of:

3-(5-nitro-2-furyl)-1H-pyrazole-4-carboxaldehyde,
1-methyl-3-(5-nitro-2-furyl)pyrazole-4-carboxaldehyde,
1-methyl-5-(5-nitro-2-furyl)pyrazole-4-carboxaldehyde,
1-ethyl-3-(5-nitro-2-furyl)pyrazole-4-carboxaldehyde,
1-(2-methoxyethyl)-3-(5-nitro-2-furyl)pyrazole-4-carboxaldehyde,
1-isopropyl-3-(5-nitro-2-furyl)pyrazole-4-carboxaldehyde,
1-benzyl-3-(5-nitro-2-furyl)pyrazole-4-carboxaldehyde,
1-(p-chlorophenyl)-3-(5-nitro-2-furyl)pyrazole-4-carboxaldehyde, and
1-(p-methoxyphenyl)-3-(5-nitro-2-furyl)pyrazole-4-carboxaldehyde, results in the corresponding preparation of:

3-(5-nitro-2-furyl)-1H-pyrazole-4-carboxaldehyde-(2-pyridyl)hydrazone [m.p. 230° C (with decomposition)],
1-methyl-3-(5-nitro-2-furyl)pyrazole-4-carboxaldehyde-(2-pyridyl)hydrazone [m.p. 235° to 237° C (with decomposition)],
1-methyl-5-(5-nitro-2-furyl)pyrazole-4-carboxaldehyde-(2-pyridyl)hydrazone [m.p. 198° C (with decomposition)],
1-ethyl-3-(5-nitro-2-furyl)pyrazole-4-carboxaldehyde-(2-pyridyl)hydrazone,
1-(2-methoxyethyl)-3-(5-nitro-2-furyl)pyrazole-4-carboxaldehyde-(2-pyridyl)hydrazone,
1-isopropyl-3-(5-nitro-2-furyl)pyrazole-4-carboxaldehyde-(2-pyridyl)hydrazone
1-benzyl-3-(5-nitro-2-furyl)pyrazole-4-carboxaldehyde-(2-pyridyl)hydrazone,
1-(p-chlorophenyl)-3-(5-nitro-2-furyl)pyrazole-4-carboxaldehyde-(2-pyridyl)-hydrazone, and
1-(p-methoxyphenyl)-3-(5-nitro-2-furyl)pyrazole-4-carboxaldehyde-(2-pyridyl)-hydrazone, respectively.

EXAMPLE 33

Following the procedure of Example 28 and similarly reacting an equivalent amount of each:

3-(5-nitro-2-furyl)-1H-pyrazole-4-carboxaldehyde,
1-methyl-3-(5-nitro-2-furyl)pyrazole-4-carboxaldehyde, and
3-(5-nitro-2-furyl)-1-phenylpyrazole-4-carboxaldehyde with N-methyl-N-(2-pyridyl)hydrazine results in the corresponding preparation of:

3-(5-nitro-2-furyl)-1H-pyrazole-4-carboxaldehydehydemethyl 2-pyridyl)hydrazone [m.p. 189° to 191° C], 1-methyl-3-(5-nitro-2-furyl)pyrazole-4-carboxaldehydemethyl-(2-pyridyl)hydrazone [m.p. 206° to 209°], 3-(5-nitro-2-furyl)-1-phenylpyrazole-4-carboxaldehydemethyl-(2-pyridyl)hydrazone [m.p. 182° to 186° C];

N-methyl-N-(2-pyridyl)hydrazine [b.p. 106.6° to 110.5° C/16 Torr.]

is obtained by boiling an admixture of 2-chloropyridine and methylhydrazine in 2-methoxyethanol under reflux.

EXAMPLE 34

4-[1-methoxycarbonyl-3-(5-nitro-2-furyl)pyrazol-4-ylmethyleneamino]-morpholine

Stir together 6.7 g of 1-methoxycarbonyl-3-(5-nitro-2-furyl)pyrazole-4-carboxaldehyde, 2.85 g of 4-aminomorpholine and 1.6 ml of glacial acetic acid in 125 ml of methanol for 3 hours at room temperature. Cool the resulting admixture on ice to produce a precipitate. Vacuum filter the precipitate and then suspend it once more in ethanol to obtain a 70% yield of 4-[1-methoxycarbonyl-3-(5-nitro-2-furyl)pyrazol-4-ylmethyleneamino]morpholine [m.p. 184° C (with decomposition)].

Replacing the carboxaldehyde with an equivalent of each of:

3-(5-nitro-2-furyl)-1H-pyrazole-4-carboxaldehyde,
1-methyl-3-(5-nitro-2-furyl)pyrazole-4-carboxaldehyde,
3-(5-nitro-2-furyl)-1-phenylpyrazole-4-carboxaldehyde,
1-(p-methoxyphenyl)-3-(5-nitro-2-furyl)pyrazole-4-carboxaldehyde, and
1-(p-chlorophenyl)-3-(5-nitro-2-furyl)pyrazole-4-carboxaldehyde similarly results in the preparation of:
4-[3-(5-nitro-2-furyl)-1H-pyrazol-4-ylmethyleneamino]-morpholine [m.p 191° to 192° C].
4-[1-methyl-3-(5-nitro-2-furyl)pyrazol-4-ylmethyleneamino]morpholine, 4-[3-(5-nitro-2-furyl)-1-phenylpyrazol-4-ylmethyleneamino]morpholine [m.p. 174.5° to 175.5° C],
4-[1-(p-methoxyphenyl)-3-(5-nitro-2-furyl)pyrazol-4-ylmethyleneamino]morpholine, and
4-[1-(p-chlorophenyl)-3-(5-nitro-2-furyl)pyrazol-4-ylmethyleneamino]morpholine, respectively.

EXAMPLE 35

3-methyl-4-[3-(5-nitro-2-furyl)-1-phenylpyrazol-4-ylmethyleneamino]-1,4-thiazane -1,1-dioxide Heat 2.83 g of 3-(5-nitro-2-furyl)-1-phenylpyrazole-4-carboxaldehyde together with 1.74 g of 4-amino-3-methyl-1,4-thiazane-1,1-dioxide, 0.5 ml of glacial acetic acid and 20 ml of ethanol for 4 hours at boiling point. Then cool the resulting reaction product to obtain a 99% yield of 3-methyl-4-[3-(5-nitro-2-furyl)-1-phenyl-pyrazol-4-ylmethyleneamino]-1,4-thiazane-1,1-dioxide [m.p. 201° to 202.5° C].

Replacing the carboxaldehyde with an equivalent of each of:

3-(5-nitro-2-furyl)-1H-pyrazole-4-carboxaldehyde and
1-methyl-3-(-nitro-2-furyl)pyrazole-4-carboxaldehyde results in the corresponding preparation of:

3-methyl-4-[3-(5-nitro-2-furyl)-1H-pyrazol-4-ylmethyleneamino]-1,4-thiazane-1,1-dioxide [m.p. 207° to 208° C] and
3-methyl-4-[1-methyl-3-(5-nitro-2-furyl)pyrazol-4-ylmethyleneamino]-1,4-thiazane-1,1-dioxide [m.p. 195.5° to 196.5° C].

EXAMPLE 36

Following the procedure of Example 32 and similarly reacting an equivalent of:

3-(5-nitro-2-furyl)-1H-pyrazole-4-carboxaldehyde with each of:

benzoylhydrazine,
acetylhydrazine,
p-hydroxybenzoylhydrazine,
o-toluoylhydrazine,
3,5-dinitro-o-toluoylhydrazine,
p-chlorobenzoylhydrazine,
0-bromobenzoylhydrazine,
anisoylhydrazine,
hexanoylhydrazine,
nicotinoylhydrazine,
isonicotinoylhydrazine,
methyl carbazate,
ethyl carbazate,
tert. -butyl carbazate,
p-methoxybenzyl carbazate,
semicarbazide and
1,3-dimethyl-4-hydrazinouracil, results in the corresponding preparation of:

3-(5-nitro-2-furyl)-1H-pyrazole-4-carboxaldehyde-benzoylhydrazone [m.p. 275° C (with decomposition)],
3-(5-nitro-2-furyl)-1H-pyrazole-4-carboxaldehyde-acetylhydrazone,
3-(5-nitro-2-furyl)-1H-pyrazole-4-carboxaldehyde-(p-hydroxybenzoyl)hydrazone, [m.p. 305° C and higher (with decomposition)],
3-(5-nitro-2-furyl)-1H-pyrazole-4-carboxaldehyde-(o-toluoyl)hydrazone [m.p. 235° to 237° C (with decomposition)],
3-(5-nitro-2-furyl)-1H-pyrazole-4-carboxaldehyde-(3,5-dinitro-o-toluoyl)hydrazone [m.p. 266° to 270° C (with decomposition)],
3-(5-nitro-2-furyl)-1H-pyrazole-4-carboxaldehyde-(p-chlorobenzoyl)hydrazone,
3-(5-nitro-2-furyl)-1H-pyrazole-4-carboxaldehyde-(o-bromobenzoyl)hydrazone,
3-(5-nitro-2-furyl)-1H-pyrazole-4-carboxaldehyde-anisoylhydrazone,
3-(5-nitro-2-furyl)-1H-pyrazole-4-carboxaldehyde-hexanoylhydrazone,
3-(5-nitro-2-furyl)-1H-pyrazole-4-carboxaldehyde-nicotinoylhydrazone,
3-(5-nitro-furyl)-1H-pyrazole-4-carboxaldehyde-isonicotinoylhydrazone [m.p. 273° C and higher (with decomposition)],
3-(5-nitro-2-furyl)-1H-pyrazole-4-carboxaldehyde-methoxycarbonylhydrazone [m.p. 254° to 255° C (with decomposition)], 3-(5-nitro-2-furyl)-1H-pyrazole-4-carboxaldehyde-ethoxycarbonylhydrazone [m.p. 257° C (with decomposition)], 3-(5-nitro-2-furyl)-1H-pyrazole-4-carboxaldehyde-tert.-butoxycarbonylhydrazone [m.p. 228° C (with decomposition)], 3-(5-nitro-2-furyl)-1H-pyrazole-4-carboxaldehyde-(p-methoxybenzyloxy)carbonylhydrazone [m.p. 216.5° C (with decomposition)], 3-(5-nitro-2-furyl)-1H-pyrazole-4-carboxaldehyde-semicarbazone [m.p. 238° C (with decomposition)], and 3-(5-nitro-2-furyl)-1H-pyrazole-4-carboxaldehyde-(1,3-dimethyl-4-uracilyl)hydrazone ]m.p. 267° C (with decomposition)], respectively.

EXAMPLE 37

Following the procedure of Example 32 and similarly reacting an equivalent of each of:

1-methyl-3-(5-nitro-2-furyl)pyrazole-4-carboxaldehyde,
1-ethyl-3-(5-nitro-2-furyl)pyrazole-4-carboxaldehde,
1-(2-methoxyethyl)-3-(5-nitro-2-furyl)pyrazole-4-carboxaldehyde,
1-isopropyl-3-(5-nitro-2-furyl)pyrazole-4-carboxaldehyde,
1-allyl-3-(5-nitro-2-furyl)pyrazole-4-carboxaldehyde,
1-(n-hexyl)-3-(5-nitro-2-furyl)pyrazole-4-carboxaldehyde,
1-cyclohexyl-3-(5-nitro-2-furyl)pyrazole-4-carboxaldehyde,
1-benzyl-3-(5-nitro-2-furyl) pyrazole-4-carboxaldehyde,
1-(p-chlorophenyl)-3-(5-nitro-2-furyl)pyrazole-4-carboxaldehyde,
1-(p-methoxyphenyl)-3-(5-nitro-2-furyl)pyrazole-4-carboxaldehyde,
1-(5-indanyl)-3-(5-nitro-2-furyl)pyrazole-4-carboxaldehyde, and
3-(5-nitro-2-furyl)-1H-pyrazole-4-carboxaldehyde,
3-(5-nitro-2-furyl)-1-phenylpyrazole-4-carboxaldehyde,
3-(5-nitro-2-furyl)-1-(p-tolyl)pyrazole-4-carboxaldehyde with acetylhydrazine results in the corresponding preparation of:

1-methyl-3-(5-nitro-2-furyl)pyrazole-4-carboxaldehyde-acetylhydrazone [m.p. 217° to 218° C (with decomposition)],
1-ethyl-3-(5-nitro-2-furyl)pyrazole-4-carboxaldehyde-acetylhydrazone,
1-(2-methoxyethyl)-3-(5-nitro-2-furyl)pyrazole-4-carboxaldehyde-acetylhydrazone,
1-isopropyl-3-(5-nitro-2-furyl)pyrazole-4-carboxaldehyde-acetylhydrazone,
1-allyl-3-(5-nitro-2-furyl)pyrazole-4-carboxaldehyde-acetylhydrazone,
1-(n-hexyl)-3-(5-nitro-2-furyl)pyrazole-4-carboxaldehyde-acetylhydrazone,
1-cyclohexyl-3-(5-nitro-2-furyl)pyrazole-4-carboxaldehyde-acetylhydrazone,
1-benzyl-3-(5-nitro-2-furyl)pyrazole-4-carboxaldehyde-acetylhydrazone,
1-(p-chlorophenyl)-3-(5-nitro-2-furyl)pyrazole-4-carboxaldehyde-acetylhydrazone,
1-(p-methoxyphenyl)-3-(5-nitro-2-furyl)pyrazole-4-carboxaldehyde-acetylhydrazone,
1-(5-indanyl)-3-(5-nitro-2-furyl)pyrazole-4-carboxaldehyde-acetylhydrazone,
3-(5-nitro-2-furyl)-1H-pyrazole-4-carboxaldehyde-acetylhydrazone,
3-(5-nitro-2-furyl)-1-phenylpyrazole-4-carboxaldehyde-acetylhydrazone [m.p. 228° to 231° C (with decomposition)], and
3-(5-nitro-2-furyl)-1-(p-tolyl)pyrazole-4-carboxaldehyde-acetylhydrazone, respectively.

EXAMPLE 38

Following the procedure of Example 32 and similarly reacting an equivalent of 1-methyl-3-(5-nitro-2-furyl)-pyrazole-4-carboxaldehyde with each of:

propionylhydrazine,
benzoylhydrazine,
0-toluoylhydrazine,
(3,5-dinitro-o-toluoyl)hydrazine,
p-chlorobenzoylhydrazine,
o-bromobenzoylhydrazine,
anisoylhydrazine,
nicotinoylhydrazine,
isonicotinoylhydrazine,
methyl carbazate,
ethyl carbazate,
4-methylsemicarbazide,
(2-methoxyethyl)carbazate, and
4,4-dimethylsemicarbazide results in the corresponding preparation of:

1-methyl-3-(5-nitro-2-furyl)pyrazole-4-carboxaldehyde-propionylhydrazone,
1-methyl-3-(5-nitro-2-furyl)pyrazole-4-carboxaldehyde-benzoylhydrazone [m.p. 225° to 227° C (with decomposition)],
1-methyl-3-(5-nitro-2-furyl)pyrazole-4-carboxaldehyde-o-toluoylhydrazone [m.p. 226° to 228° C (with decomposition)],
1-methyl-3-(5-nitro-2-furyl)pyrazole-4-carboxaldehyde-(3,5-dinitro-o-toluoyl)-hydrazone [m.p. 235° to 237° C (with decomposition],
1-methyl-3-(5-nitro-2-furyl)pyrazole-4-carboxaldehyde-p-chlorobenzoylhydrazone,
1-methyl-3-(5-nitro-2-furyl)pyrazole-4-carboxaldehyde-o-bromobenzoylhydrazone,
1-methyl-3-(5-nitro-2-furyl)pyrazole-4-carboxaldehyde-anisoylhydrazone,
1-methyl-3-(5-nitro-2-furyl)pyrazole-4-carboxaldehyde-nicotinoylhydrazone,
1-methyl-3-(5-nitro-2-furyl)pyrazole-4-carboxaldehyde-isonicotinoylhydrazone [m.p. 202° C or higher (with decomposition)],
1-methyl-3-(5-nitro-2-furyl)pyrazole-4-carboxaldehyde-methoxycarbonylhydrazone [m.p. 213° to 214° C (with decomposition)],
1-methyl-3-(5-nitro-2-furyl)pyrazole-4-carboxaldehyde-ethoxycarbonylhydrazone [m.p. 217.5° to 219° C (with decomposition)],
1-methyl-3-(5-nitro-2-furyl)pyrazole-4-carboxaldehyde-4-methylsemicarbazone [m.p. 223° to 225° C (with decomposition)],
1-methyl-3-(5-nitro-2-furyl)pyrazole-4-carboxaldehyde-(2-methoxyethoxy)carbonylhydrazone [m.p. 196° to 197° C (with decomposition)], and 1-methyl-3-(5-nitro-2-furyl)pyrazole-4-carboxaldehyde-4,4-dimethylsemicarbazone [m.p. 200° to 202° C (with decomposition)], respectively.

EXAMPLE 39

Following the procedure of Example 28 and similarly reacting an equivalent of 3-(5-nitro-2-furyl)-1-phenylpyrazole-4-carboxaldehyde with each of:

propionylhydrazine,
benzoylhydrazine,
p-chlorobenzoylhydrazine,
anisoylhydrazine,
o-toluoylhydrazine,
nicotinoylhydrazine, and
isonicotinoylhydrazine, results in the corresponding preparation of:

3-(5-nitro-2-furyl)-1-phenylpyrazole-4-carboxaldehyde-propionylhydrazone,
3-(5-nitro-2-furyl)-1-phenylpyrazole-4-carboxaldehyde-benzoylhydrazone [m.p. 220° to 222° C (with decomposition)],
3-(5-nitro-2-furyl)-1-phenylpyrazole-4-carboxaldehyde-p-chlorobenzoylhydrazone,
3-(5-nitro-2-furyl)-1-phenylpyrazole-4-carboxaldehyde-anisoylhydrazone,
3-(5-nitro-2-furyl)-1-phenylpyrazole-4-carboxaldehyde-o-toluoylhydrazone [m.p. 226° to 229° C (with decomposition], 3-(5-nitro-2-furyl)-1-phenylpyrazole-4-carboxaldehyde-nicotinoylhydrazone, and
3-(5-nitro-2-furyl)-1-phenylpyrazole-4-carboxaldehyde-isonicotinoylhydrazone [m.p. 242° to 245° C (with decomposition)], respectively.

EXAMPLE 40

1-methyl-3-(5-nitro-2-furyl)pyrazole-4-carboxaldehyde-ethoxycarbonylhydrazone

Add a solution of 19.5 g of ethyl carbazate in 250 ml of ethanol dropwise to 35 g of 1-methyl-3-(5-nitro-2-furyl)pyrazole-4-carboxaldehyde and 1 ml of glacial acetic acid in 400 ml of ethanol. Stir the resulting reaction mixture for 80 minutes at from 35° to 40° C, and add 650 ml of water dropwise to the thus-obtained suspension at room temperature. Cool in an ice bath and separate the produced precipitate by vacuum filtration. Wash the residue with ethanol/water (1:1) and with water to obtain a 97% yield of 1-methyl-3-(5-nitro-2-furyl)pyrazole-4-carboxaldehyde-ethoxycarbonylhydrazone [m.p. 217.5° to 219° C (with decomposition)].

In a similar manner by replacing the carboxaldehyde by an equivalent of each of:

1-ethyl-3-(5-nitro-2-furyl)pyrazole-4-carboxaldehyde,
1-isopropyl-3-(5-nitro-2-furyl)pyrazole-4-carboxaldehyde,
1-isoamyl-3-(5-nitro-2-furyl)pyrazole-4-carboxaldehyde,
1-(n-hexyl)-3-(5-nitro-2-furyl)pyrazole-4-carboxaldehyde,
1-cyclohexyl-3-(5-nitro-2-furyl)pyrazole-4-carboxaldehyde,
1-allyl-3-(5-nitro-2-furyl)pyrazole-4-carboxaldehyde,
1-(2-methoxyethyl)-3-(5-nitro-2-furyl)pyrazole-4-carboxaldehyde,
1-benzyl-3-(5-nitro-2-furyl)pyrazole-4-carboxaldehyde, and
1-(p-chlorobenzyl)-3-(5-nitro-2-furyl)pyrazole-4-carboxaldehyde, each of the following:

1-ethyl-3-(5-nitro-2-furyl)pyrazole-4-carboxaldehyde-ethoxycarbonylhydrazone [m.p. 214° to 216° C (with decomposition)],
1-isopropyl-3-(5-nitro-2-furyl)pyrazole-4-carboxaldehyde-ethoxycarbonylhydrazone [m.p. 197° to 198° C (with decomposition)],
1-isoamyl-3-(5-nitro-2-furyl)pyrazole-4-carboxaldehyde-ethoxycarbonylhydrazone,
1-(n-hexyl)-3-(5-nitro-2-furyl)pyrazole-4-carboxaldehyde-ethoxycarbonylhydrazone,
1-cyclohexyl-3-(5-nitro-2-furyl)pyrazole-4-carboxaldehyde-ethoxycarbonylhydrazone,
1-allyl-3-(5-nitro-2-furyl)pyrazole-4-carboxaldehyde-ethoxycarbonylhydrazone [m.p. 199° to 200° C (with decomposition)],
1-(2-methoxyethyl)-3-(5-nitro-2-furyl)pyrazole-4-carboxaldehyde-ethoxycarbonylhydrazone [m.p. 196.5° to 197.5° C (with decomposition)],
1-benzyl-3-(5-nitro-2-furyl)pyrazole-4-carboxaldehyde-ethoxycarbonylhydrazone [m.p. 208° to 210° C (with decomposition)], and
1-(p-chlorobenzyl)-3-(5-nitro-2-furyl)pyrazole-4-carboxaldehyde-ethoxycarbonylhydrazone, respectively, is obtained.

EXAMPLE 41

3-(5-nitro-2-furyl)-1-phenylpyrazole-4-carboxaldehyde-ethoxycarbonylhydrazone

Stir 48 g of 3-(5-nitro-2-furyl)-1-phenylpyrazole-4-carboxaldehyde together with 22 g of ethyl carbazate, 5 drops of glacial acetic acid and 500 ml of ethanol for 3 hours at 60° C. Add 500 ml of water dropwise to the resulting reaction mixture at room temperature. Vacuum filter and wash the obtained precipitate with ethanol/water and with water. Dry the precipitate and then admix it with toluene at 90° C to obtain a 94% yield of 3-(5-nitro-2-furyl)-1-phenylpyrazole-4-carboxaldehyde-ethoxycarbonylhydrazone [m.p. 200° to 201° C].

Replacing the carboxaldehyde with an equivalent of each of:

1-(p-chlorophenyl)-3-(5-nitro-2-furyl)pyrazole-4-carboxaldehyde,
1-(m-chlorophenyl)-3-(5-nitro-2-furyl)pyrazole-4-carboxaldehyde,
1-(o-chlorophenyl)-3-(5-nitro-2-furyl)pyrazole-4-carboxaldehyde,
1-(p-bromophenyl)-3-(5-nitro-2-furyl)pyrazole-4-carboxaldehyde,
1-(p-fluorophenyl)-3-(5-nitro-2-furyl)pyrazole-4-carboxaldehyde,
1-(p-methoxyphenyl)-3-(5-nitro-2-furyl)pyrazole-4-carboxaldehyde,
1-(3-chloro-p-tolyl)-3-(5-nitro-2-furyl)pyrazole-4-carboxaldehyde,
1-(3,4-dichlorophenyl)-3-(5-nitro-2-furyl)pyrazole-4-carboxaldehyde,
1-(3,4-dimethoxyphenyl)-3-(5-nitro-2-furyl)pyrazole-4-carboxaldehyde, 1-(2-naphthyl)-3-(5-nitro-2-furyl)pyrazole-4-carboxaldehyde, 1-(p-biphenylyl)-3-(5-nitro-2-furyl)pyrazole-4-carboxaldehyde, 1-(5-indanyl)-3-(5-nitro-2-furyl)pyrazole-4-carboxaldehyde, 3-(5-nitro-2-furyl)-1-(p-tolyl)pyrazole-4-carboxaldehyde, 3-(5-nitro-2-furyl)-1-(p-nitrophenyl)pyrazole-4-carboxaldehyde, 3-(5-nitro-2-furyl)-1-(m-nitrophenyl)pyrazole-4-carboxaldehyde, and 3-(5-nitro-2-furyl)-1-(α,α,α-trifluoro-m-tolyl)-4-carboxaldehyde results in the corresponding preparation of:

1-(p-chlorophenyl)-3-(5-nitro-2-furyl)pyrazole-4-carboxaldehyde-ethoxycarbonylhydrazone [m.p. 221° to 223° C (with decomposition)], 1-(m-chlorophenyl)-3-(5-nitro-2-furyl)pyrazole-4-carboxaldehyde-ethoxycarbonylhydrazone [m.p. 201° to 202° C].

1-(o-chlorophenyl)-3-(5-nitro-2-furyl)pyrazole-4-carboxaldehyde-ethoxycarbonylhydrazone [m.p. 190° to 191° C], 1-(p-bromophenyl)-3-(5-nitro-2-furyl)pyrazole-4-carboxaldehyde-ethoxycarbonylhydazone [m.p. 222.5° to 224° C (with decomposition)], 1-(p-fluorophenyl)-3-(5-nitro-2-furyl)pyrazole-4-carboxaldehyde-ethoxycarbonylhydrazone [m.p. 215° to 216° C (with decomposition)], 1-(p-methoxyphenyl)-3-(5-nitro-2-furyl)pyrazole-4-carboxaldehyde-ethoxycarbonylhydrazone [m.p. 198° to 199° C (with decomposition)], 1-(3-chloro-p-tolyl)-3-(5-nitro-2-furyl)pyrazole-4-carboxaldehyde-ethoxycarbonylhydrazone [m.p. 210° to 211° C (with decomposition)], 1-(3,4-dichlorophenyl)-3-(5-nitro-2-furyl)pyrazole-4-carboxaldehyde-ethoxycarbonylhydrazone [m.p. 215° to 216° C (with decomposition)], 1-(3,4-dimethoxyphenyl)-3-(5-nitro-2-furyl)pyrazole-4-carboxaldehyde-ethoxycarbonylhydrazone, 1-(2-naphthyl)-3-(5-nitro-2-furyl)pyrazole-4-carboxaldehyde-ethoxycarbonylhydrazone, 1-(p-biphenylyl)-3-(5-nitro-2-furyl)pyrazole-4-carboxaldehyde-ethoxycarbonylhydrazone, 1-(5-indanyl)-3-(5-nitro-2-furyl)pyrazole-4-carboxaldehyde-ethoxycarbonylhydrazone, 3-(5-nitro-2-furyl)-1-(p-tolyl)pyrazole-4-carboxaldehyde-ethoxycarbonylhydrazone [m.p. 210° to 211° C (with decomposition)], 3-(5-nitro-2-furyl)-1-(p-nitrophenyl)pyrazole-4-carboxaldehyde-ethoxycarbonylhydrazone [m.p. 248.5° to 250° C (with decomposition)], 3-(5-nitro-2-furyl)-1-(m-nitrophenyl)pyrazole-4-carboxaldehyde-ethoxycarbonylhydrazone [m.p. 236.5° to 238° C (with decomposition)], and 3-(5-nitro-2-furyl)-1-(α,α,α-trifluoro-m-tolyl)-4-carboxaldehyde-ethoxycarbonylhydrazone, respectively.

EXAMPLE 42

Following the procedure of Example 40 and similarly reacting an equivalent of each of:

1-methyl-3-(5-nitro-2-furyl)pyrazole-4-carboxaldehyde, 1-ethyl-3-(5-nitro-2-furyl)pyrazole-4-carboxaldehyde, 1-isopropyl-3-(5-nitro-2-furyl)pyrazole-4-carboxaldehyde, 1-allyl-3-(5-nitro-2-furyl)pyrazole-4-carboxaldehyde, 1-(2-methoxyethyl)-3-(5-nitro-2-furyl)pyrazole-4-carboxaldehyde, 1-benzyl-3-(5-nitro-2-furyl)pyrazole-4-carboxaldehyde, 1-(p-chlorophenyl)-3-(5-nitro-2-furyl)pyrazole-4-carboxaldehyde, 1-(p-fluorophenyl)-3-(5-nitro-2-furyl)pyrazole-4-carboxaldehyde, 1-(p-methoxyphenyl)-3-(5-nitro-2-furyl)pyrazole-4-carboxaldehyde, 3-(5-nitro-2-furyl)-1-phenylpyrazole-4-carboxaldehyde, and 3-(5-nitro-2-furyl)-1-(p-tolyl)pyrazole-4-carboxaldehyde with methyl carbazate, results in the corresponding preparation of:

1-methyl-3-(5-nitro-2-furyl)pyrazole-4-carboxaldehyde-methoxycarbonylhydrazone [m.p. 213° to 214° C (with decomposition)], 1-ethyl-3-(5-nitro-2-furyl)pyrazole-4-carboxaldehyde-methoxycarbonylhydrazone, 1-isopropyl-3-(5-nitro-2-furyl)pyrazole-4-carboxaldehyde-methoxycarbonylhydrazone, 1-allyl-3-(5-nitro-2-furyl)pyrazole-4-carboxaldehyde-methoxycarbonylhydrazone, 1-(2-methoxyethyl)-3-(5-nitro-2-furyl)pyrazole-4-carboxaldehyde-methoxycarbonylhydrazone, 1-benzyl-3-(5-nitro-2-furyl)pyrazole-4-carboxaldehyde-methoxycarbonylhydrazone, 1-(p-chlorophenyl)-3-(5-nitro-2-furyl)pyrazole-4-carboxaldehyde-methoxycarbonylhydrazone, 1-(p-fluorophenyl)-3-(5-nitro-2-furyl)pyrazole-4-carboxaldehyde-methoxycarbonylhydrazone, 1-(p-methoxyphenyl)-3-(5-nitro-2-furyl)pyrazole-4-carboxaldehyde-methoxycarbonylhydrazone, 3-(5-nitro-2-furyl)-1-phenylpyrazole-4-carboxaldehyde-methoxycarbonylhydrazone, and 3-(5-nitro-2-furyl)-1-(p-tolyl)pyrazole-4-carboxaldehyde-methoxycarbonylhydrazone, respectively.

EXAMPLE 43

3-(5-nitro-2-furyl)-1H-pyrazole-4-carboxaldehyde-thiosemicarbazone

Stir 4.14 g of 3-(5-nitro-2-furyl)-1H-pyrazole-4-carboxaldehyde together with 2.0 g. of thiosemicarbazide, 2 drops of glacial acetic acid and 40 ml of ethanol for 2 hours at 50° C and then for 4 days at room temperature. Dilute the resulting product with water to produce a 95% yield of 3-(5-nitro-2-furyl)-1H-pyrazole-4-carboxaldehyde-thiosemicarbazone [m.p. above 350° C (with decomposition)].

Following the same procedure, 1-methyl-3-(5-nitro-2-furyl)pyrazole-4-carboxaldehyde-thiosemicarbazone [m.p. above 350° C] is similarly prepared from equivalent amounts of corresponding reactants.

EXAMPLE 44

1-[1-methyl-3-(5-nitro-2-furyl)pyrazol-4-ylmethyleneamino]hydantoin

Add 5.2 g of methyl chloroacetate to a solution of 4 g of acetonesemicarbazone and 16 g of 30% methanolic sodium methylate solution in 28 ml of isopropanol. Boil the resulting reaction mixture for 1.5 hours before distilling in vacuo to remove solvent. Mix the residue with 24 ml of water and 4.4 ml of concentrated hydrochloric acid. Clarify with active charcoal. Add thereto 6.5 g of 1-methyl-3-(5-nitro-2-furyl)pyrazole-4-carboxaldehyde and then heat for 2 hours at boiling point. Separate the formed precipitate by vacuum filtration, recrystallize the residue from dimethylformamide/water to obtain a 90% yield of 1-[1-methyl-3-(5-nitro-2-furyl)pyrazol-4-ylmethyleneamino]hydantoin [m.p. 288° to 290° C (with decomposition)].

Following the same procedure 1-[3-(5-nitro-2-furyl)-1-phenylpyrazol-4-ylmethyleneamino]hydantoin [m.p. 320° to 325° C (with decomposition)] is similarly prepared from equivalent amounts of corresponding reactants.

EXAMPLE 45

3-(5-nitro-2-furyl)-1H-pyrazole-4-carbonitrile

Heat Then g. of 3-(5-nitro-2-furyl)-1H-pyrazole-4-carboxaldehydeoxime together with 3.4 g of phosphorus oxychloride in 20 ml of 1,2-dichloroethane for 1 hour under reflux. To the resulting product add ice together with 50 ml of water. The adjust the pH to from 3 to 4 with sodium hydrogen carbonate and remove the formed crystals by vacuum filtration. Wash the crystals with water to obtain a 96% yield of 3-(5-nitro-2-furyl)-1H-pyrazole-4-carbonitrile [m.p. 237.5° to 239° C (from ethanol)].

Replacing the carboxaldehydeoxime with an equivalent of each of:

1-methyl-3-(5-nitro-2-furyl)pyrazole-4-carboxaldehydeoxime and
3-(5-nitro-2-furyl)-1-phenylpyrazole-4-carboxaldehydeoxime results in the corresponding preparation of:

1-methyl-3-(5-nitro-2-furyl)pyrazole-4-carbonitrile [m.p. 176.5° to 177.5° C] and
3-(5-nitro-2-furyl)-1-phenylpyrazole-4-carbonitrile [m.p. 190° to 192° C], respectively.

EXAMPLE 46

(a) 1-methyl-3-(5-nitro-2-furyl)pyrazole-4-carbonitrile

Add 15.4 g of 3-(5-nitro-2-furyl)-1H-pyrazole-4-carbonitrile portionwise to a suspension of 2.5 g of sodium hydride (80% in liquid paraffin) in 90 ml of dimethylformamide while stirring and under nitrogen at from −2° C to −5° C. Stir the thus-obtained reaction mixture for 30 minutes and then add dropwise thereto a solution of 11.8 g of methyl iodide in 20 ml of dimethylformamide. After stirring for 30 minutes, admix therewith 0.6 g of glacial acetic acid and stir the resulting solution into 220 g of ice and water. Remove formed precipitate by vacuum filtration and recrystallize residue twice from dimethylformamide and water. Dry the residue in vacuo. Recrystallize the resulting 13.5 g of product three more times from dimethylformamide and water to obtain a 57% yield of 1-methyl-3-(5-nitro-2-furyl)pyrazole-4-carbonitrile [m.p. 176.5° to 177.5° C].

(b) 1-methyl-5-(5-nitro-2-furyl)pyrazole-4-carbonitrile

Evaporate the mother liquors of the preceding batch in vacuum to dryness, fractionally recrystallize the residue from toluene and clarify it with Tonsil ® to obtain 1-methyl-5-(5-nitro-2-furyl)pyrazole-4-carbonitrile [m.p. 149.5° to 151.5° C].

EXAMPLE 47

Replacing the methyl iodide of Example 46 with an equivalent of each of: ethyl iodide, isopropyl bromide, isoamyl bromide, n-hexyl bromide, benzyl bromide, p-chlorobenzyl chloride, allyl bromide, cyclohexyl bromide and 2-chloroethyl-methyl ether, results in the corresponding preparation of:

1-ethyl-3-(5-nitro-2-furyl)pyrazole-4-carbonitrile [m.p. 159° to 160° C],
1-isopropyl-3-(5-nitro-2-furyl)pyrazole-4-carbonitrile [m.p. 181° to 182° C],
1-isoamyl-3-(5-nitro-2-furyl)pyrazole-4-carbonitrile,
1-n-hexyl-3-(5-nitro-2-furyl)pyrazole-4-carbonitrile,
1-benzyl-3-(5-nitro-2-furyl)pyrazole-4-carbonitrile [m.p. 111.5° to 113° C],
1-(p-chlorobenzyl)-3-(5-nitro-2-furyl)pyrazole-4-carbonitrile,
1-allyl-3-(5-nitro-2-furyl)pyrazole-4-carbonitrile [m.p. 86.5° to 88° C],
1-cyclohexyl-3-(5-nitro-2-furyl)pyrazole-4-carbonitrile, and
1-(2-methoxyethyl)-3-(5-nitro-2-furyl)pyrazole-4-carbonitrile, respectively From the mother liquor the corresponding 5-(5-nitro-2-furyl)-isomers are obtained by chromatography on a silica gel column.

EXAMPLE 48

1-isopropyl-3-(5-nitro-2-furyl)pyrazole-4-carbonitrile

Stir an admixture of 3.4 g of finely pulverized 1-isopropyl-3-(5-nitro-2-furyl)pyrazole-4-carboxaldehydeoxime in 15 ml of 1,2-dichloroethane with 1.8 g of thionyl chloride for 80 minutes at 55° C. Evaporate the resulting solution to dryness in vacuo and then evaporate to dryness twice more after mixing with 1,2-dichloroethane to obtain a 99% yield of 1-isopropyl-3-(5-nitro-2-furyl)pyrazole-4-carbonitrile [m.p. 181° to 182° C (from ethanol)].

Replacing the carboxaldehydeoxime with an equivalent of each of:

3-(5-nitro-2-furyl)-1H-pyrazole-4-carboxaldehydeoxime,
1-methyl-3-(5-nitro-2-furyl)pyrazole-4-carboxaldehydeoxime,
1-methyl-5-(5-nitro-2-furyl)pyrazole-4-carboxaldehydeoxime,
1-ethyl-3-(5-nitro-2-furyl)pyrazole-4-carboxaldehydeoxime,
1-isoamyl-3-(5-nitro-2-furyl)pyrazole-4-carboxaldehydeoxime,
1-(n-hexyl)-3-(5-nitro-2-furyl)pyrazole-4-carboxaldehydeoxime,
1-benzyl-3-(5-nitro-2-furyl)pyrazole-4-carboxaldehydeoxime,
1-(p-chlorobenzyl)-3-(5-nitro-2-furyl)pyrazole-4-carboxaldehydeoxime,
1-allyl-3-(5-nitro-2-furyl)pyrazole-4-carboxaldehydeoxime,
1-cyclohexyl-3-(5-nitro-2-furyl)pyrazole-4-carboxaldehydeoxime, 1-(2-methoxyethyl)-3-(5-nitro-2-furyl)pyrazole-4-carboxaldehydeoxime,
3-(5-nitro-2-furyl)-1-phenylpyrazole-4-carboxaldehydeoxime,
1-(o-chlorophenyl)-3-(5-nitro-2-furyl)pyrazole-4-carboxaldehydeoxime,
1-(m-chlorophenyl)-3-(5-nitro-2-furyl)pyrazole-4-carboxaldehydeoxime,
1-(p-chlorophenyl)-3-(5-nitro-2-furyl)pyrazole-4-carboxaldehydeoxime,
3-(5-nitro-2-furyl)-1-(p-tolyl)pyrazole-4-carboxaldehydeoxime,
1-(p-bromophenyl)-3-(5-nitro-2-furyl)pyrazole-4-carboxaldehydeoxime,
1-(p-fluorophenyl)-3-(5-nitro-2-furyl)pyrazole-4-carboxaldehydeoxime,
1-(p-methoxyphenyl)-3-(5-nitro-2-furyl)pyrazole-4-carboxaldehydeoxime, and
3-(5-nitro-2-furyl)-1-(p-nitrophenyl)pyrazole-4-carboxaldehydeoxime results in the corresponding preparation of:

3-(5-nitro-2-furyl)-1H-pyrazole-4-carbonitrile [m.p. 237.5° to 239° C],
1-methyl-3-(5-nitro-2-furyl)pyrazole-4-carbonitrile [m.p. 176.5° to 177.5° C],
1-methyl-5-(5-nitro-2-furyl)pyrazole-4-carbonitrile [m.p. 149.5° to 151.5° C],
1-ethyl-3-(5-nitro-2-furyl)pyrazole-4-carbonitrile [m.p. 159° to 160° C],
1-isoamyl-3-(5-nitro-2-furyl)pyrazole-4-carbonitrile,
1-(n-hexyl)-3-(5-nitro-2-furyl)pyrazole-4-carbonitrile,
1-benzyl-3-(5-nitro-2-furyl)pyrazole-4-carbonitrile [m.p. 111.5° to 113° C],
1-(p-chlorophenyl)-3-(5-nitro-2-furyl)pyrazole-4-carbonitrile,
1-allyl-3-(5-nitro-2-furyl)pyrazole-4-carbonitrile [m.p. 86.5° to 88° C],
1-cyclohexyl-3-(5-nitro-2-furyl)pyrazole-4-carbonitrile,
1-(2-methoxyethyl)-3-(5-nitro-2-furyl)pyrazole-4-carbonitrile,
3-(5-nitro-2-furyl)-1-phenylpyrazole-4-carbonitrile [m.p. 190° to 192° C],
1-(o-chlorophenyl)-3-(5-nitro-2-furyl)pyrazole-4-carbonitrile [m.p. 174° to 176° C],
1-(m-chlorophenyl)-3-(5-nitro-2-furyl)pyrazole-4-carbonitrile [m.p. 200° to 201° C],
1-(p-chlorophenyl)-3-(5-nitro-2-furyl)pyrazole-4-carbonitrile [m.p. 188° to 190° C],
3-(5-nitro-2-furyl)-1-(p-tolyl)pyrazole-4-carbonitrile [185° to 186° C],
1-(p-bromophenyl)-3-(5-nitro-2-furyl)pyrazole-4-carbonitrile [m.p. 214.5° to 215.5° C (with decomposition)],
1-(p-fluorophenyl)-3-(5-nitro-2-furyl)pyrazole-4-carbonitrile [m.p. 169° to 170° C]
1-(p-methoxyphenyl)-3-(5-nitro-2-furyl)pyrazole-4-carbonitrile [m.p. 209° to 210° C (with decomposition)], and
3-(5-nitro-2-furyl)-1-(p-nitrophenyl)pyrazole-4-carbonitrile [m.p. 274.5° to 276° C (with decomposition)], respectively.

EXAMPLE 49

3-(5-nitro-2-furyl)-1-phenylpyrazole-4-carbonitrile

Add 9.4 ml of thionyl chloride to a suspension of 32.6 g of finely-ground 3-(5-nitro-2-furyl)-1-phenylpyrazole-4-carboxaldehydeoxime in 250 ml of carbon tetrachloride at 60° to 65° C. Stir the resulting admixture for 1.5 hours at this temperature and for 2 hours under reflux. Separate the formed precipitate by vacuum filtration at room temperature. Wash the filter residue (precipitate) with carbon tetrachloride and dry to obtain a 96% yield of 3-(5-nitro-2-furyl)-1-phenylpyrazole-4-carbonitrile [m.p. 190° to 192° C].

Replacing the carboxaldehydeoxime by an equivalent of each of:

1-(p-chlorophenyl)-3-(5-nitro-2-furyl)pyrazole-4-carboxaldehydeoxime,
1-(p-methoxyphenyl)-3-(5-nitro-2-furyl)pyrazole-4-carboxaldehydeoxime,
1-(3-chloro-p-tolyl)-3-(5-nitro-2-furyl)pyrazole-4-carboxaldehydeoxime,
1-(3,4-dichlorophenyl)-3-(5-nitro-2-furyl)pyrazole-4-carboxaldehydeoxime,
1-(3,4-dimethoxyphenyl)-3-(5-nitro-2-furyl)pyrazole-4-carboxaldehydeoxime,
1-(2-naphthyl)-3-(5-nitro-2-furyl)pyrazole-4-carboxaldehydeoxime,
1-(p-biphenylyl)-3-(5-nitro-2-furyl)pyrazole-4-carboxaldehydeoxime,
1-(5-indanyl)-3-(5-nitro-2-furyl)pyrazole-4-carboxaldehydeoxime,
3-(5-nitro-2-furyl)-1-(m-nitrophenyl)pyrazole-4-carboxaldehydeoxime,
3-(5-nitro-2-furyl)-1-(a,a,a-trifluoro-m-tolyl)pyrazole-4-carboxaldehydeoxime results in the corresponding preparation of:

1-(p-chlorophenyl)-3-(5-nitro-2-furyl)pyrazole-4-carbonitrile [m.p. 188° to 190° C],
1-(p-methoxyphenyl)-3-(5-nitro-2-furyl)pyrazole-4-carbonitrile [m.p. 209° to 210° C (with decomposition)],
1-(3-chloro-p-tolyl)-3-(5-nitro-2-furyl)pyrazole-4-carbonitrile [m.p. 188° to 189° C],
1-(3,4-dichlorophenyl)-3-(5-nitro-2-furyl)pyrazole-4-carbonitrile [m.p. 223° to 224° C],
1-(3,4-dimethoxyphenyl)-3-(5-nitro-2-furyl)pyrazole-4-carbonitrile,
1-(2-naphthyl)-3-(5-nitro-2-furyl)pyrazole-4-carbonitrile,
1-p-biphenylyl)-3-(5-nitro-2-furyl)pyrazole-4-carbonitrile,
1-(5-indanyl)-3-(5-nitro-2-furyl)pyrazole-4-carbonitrile,
3-(5-nitro-2-furyl)-1-(m-nitrophenyl)pyrazole-4-carbonitrile [m.p. 206.5° to 208° C], and
3-(5-nitro-2-furyl)-1-($\alpha,\alpha,\alpha$-trifluoro-m-tolyl)pyrazole-4-carbonitrile, respectively.

EXAMPLE 50

3-(5-nitro-2-furyl)-1-phenylpyrazole-4-carbonitrile

Stir 5 g of 3-(5-nitro-2-furyl)-1-phenylpyrazole-4-carboxaldehyde together with 1.29 of hydroxylamine hydrochloride and 1.52 g of anhydrous sodium acetate in 15 ml of dimethylformamide for 1.5 hours at room temperature. Then add 2.85 g of phosphorus oxychloride dropwise to the resulting reaction mixture, the temperature of which rises to 40° C. Stir for 1 hour and then confirm that the reaction is complete by a thin layer chromatograph. Allow the solution to stand overnight and then pour onto 90 ml of ice water. Stir for 30 minutes at room temperature and then for 30 minutes at 40° C. Draw off the formed precipitate by vacuum filtration, wash the precipitate well with water and dry to obtain a 98% yield of 3-(5-nitro-2-furyl)-1-phenylpyrazole-4-carbonitrile [m.p. 190° to 192° C].

Following the same procedure and similarly reacting an equivalent of each of:

3-(5-nitro-2-furyl)-1H-pyrazole-4-carboxaldehyde,
1-methyl-3-(5-nitro-2-furyl)pyrazole-4-carboxaldehyde,
1-n-hexyl-3-(5-nitro-2-furyl)pyrazole-4-carboxaldehyde,
1-benzyl-3-(5-nitro-2furyl)pyrazole-4-carboxaldehyde,
1-cyclohexyl-3-(5-nitro-2-furyl)pyrazole-4-carboxaldehyde,
1-allyl-3-(5-nitro-2-furyl)pyrazole-4-carboxaldehyde,
1-(2-methoxyphenyl)-3-(5-nitro-2-furyl)pyrazole-4-carboxaldehyde,
1-(p-chlorophenyl)-3-(5-nitro-2-furyl)pyrazole-4-carboxaldehyde,
1-(p-fluorophenyl)-3-(5-nitro-2-furyl)pyrazole-4-carboxaldehyde,
1-(p-methoxyphenyl)-3-(5-nitro-2-furyl)pyrazole-4-carboxaldehyde,
1-(3-chloro-p-tolyl)-3-(5-nitro-2-furyl)pyrazole-4-carboxaldehyde,
1-(5-indanyl)-3-(5-nitro-2-furyl)pyrazole-4-carboxaldehyde,
3-(5-nitro-2-furyl)-1-(p-tolyl)pyrazole-4-carboxaldehyde,
3-(5-nitro-2-furyl)-1-(p-nitrophenyl)pyrazole-4-carboxaldehyde, and
3-(5-nitro-2-furyl)-1-(α,α,α-m-tolyl)pyrazole-4-carboxaldehyde, with hydroxylamine, glacial acetic acid and phosphorus oxychloride in dimethylformamide, results in the corresponding preparation of:

3-(5-nitro-2-furyl)-1H-pyrazole-4-carbonitrile [m.p. 237.5° to 239° C],
1-methyl-3-(5-nitro-2-furyl)pyrazole-4-carbonitrile [m.p. 176.5° to 177.5° C],
1-n-hexyl-3-(5-nitro-2-furyl)pyrazole-4-carbonitrile,
1-benzyl-3-(5-nitro-2-furyl)pyrazole-4-carbonitrile [m.p. 111.5° to 113° C],
1-cyclohexyl-3-(5-nitro-2-furyl)pyrazole-4-carbonitrile,
1-allyl-3-(5-nitro-2-furyl)pyrazole-4-carbonitrile [m.p. 86.5° to 88° C],
1-(2-methoxyethyl)-3-(5-nitro-2-furyl)pyrazole-4carbonitrile,
1-(p-chlorophenyl)-3-(5-nitro-2-furyl)pyrazole-4-carbonitrile [m.p. 188° to 190° C],
1-(p-fluorophenyl)-3-(5-nitro-2-furyl)pyrazole-4-carbonitrile [m.p. 169° to 170° C],
1-(p-methoxyphenyl)-3-(5-nitro-2-furyl)pyrazole-4-carbonitrile [m.p. 209° to 210° C (with decomposition),
1-(3-chloro-p-tolyl)-3-(5-nitro-2-furyl)pyrazole-4-carbonitrile [m.p. 188° to 189° C],
1-(5-indanyl)-3-(5-nitro-2-furyl)pyrazole-4-carbonitrile,
3-(5-nitro-2-furyl)-1-(p-tolyl)pyrazole-4-carbonitrile [m.p. 185° to 186° C],
3-(5-nitro-2-furyl)-1-(p-nitrophenyl)pyrazole-4-carbonitrile [m.p. 274.5° to 276° C (with decomposition)], and
3-(5-nitro-2-furyl)-1-(α,α,α-trifluoro-m-tolyl)pyrazole-4-carbonitrile, respectively.

EXAMPLE 51

3-(5-nitro-2-furyl)-1-phenylpyrazole-4-carbonitrile

Boil (under reflux) 5 g of 3-(5-nitro-2-furyl)-1-phenylpyrazole-4-carboxaldehyde together with 7.6 g of activated manganese dioxide and 300 ml of toluene with the introduction of ammonia using a water-trap. Filter after 5 hours and then evaporate the filtrate to dryness in vacuo before recrystallizing three times from dimethylformamide and water to obtain 3-(5-nitro-2-furyl)-1-phenylpyrazole-4-carbonitrile [m.p. 190° to 192° C].

Replacing the carboxaldehyde with an equivalent of each of:

1-methyl-3-(5-nitro-2-furyl)pyrazole-4-carboxaldehyde,
1-isopropyl-3-(5-nitro-2-furyl)pyrazole-4-carboxaldehyde,
1-(n-hexyl)-3-(5-nitro-2-furyl)pyrazole-4-carboxaldehyde,
1-(p-chlorophenyl)-3-(5-nitro-2-furyl)pyrazole-4-carboxaldehyde,
1-(m-chlorophenyl)-3-(5-nitro-2-furyl)pyrazole-4-carboxaldehyde, and
1-(o-chlorophenyl)-3-(5-nitro-2-furyl)pyrazole-4-carboxaldehyde results in the corresponding preparation of:

1-methyl-3-(5-nitro-2-furyl)pyrazole-4-carbonitrile [m.p. 176.5° to 177.5° C],
1-isopropyl-3-(5-nitro-2-furyl)pyrazole-4-carbonitrile [m.p. 181° to 182° C],
1-(n-hexyl)-3-(5-nitro-2-furyl)pyrazole-4-carbonitrile,
1-(p-chlorophenyl)-3-(5-nitro-2-furyl)pyrazole-4-carbonitrile [m.p. 188° to 190° C],
1-(m-chlorophenyl)-3-(5-nitro-2-furyl)pyrazole-4-carbonitrile [m.p. 200° to 201° C], and
1-(o-chlorophenyl)-3-(5-nitro-2-furyl)pyrazole-4-carbonitrile [m.p. 174° to 176° C], respectively.

EXAMPLE 52

3-(5-nitro-2-furyl)-1-phenylpyrazole-4carbonitrile

Heat at its boiling point a mixture of 10 g of 3-(5-nitro-2-furyl)-1-phenylpyrazole-4-carboxamide and 16.5 g of phosphorus oxychloride in 100 ml of 1,2-dichloroethane for 1 hour. Pour the resulting solution onto ice, and adjust the pH-value to 4 with saturated caustic soda solution. Separate the organic phase. Wash it with water and then evaporate it to dryness to obtain a 95% yield of 3-(5-nitro-2-furyl)-1-phenylpyrazole-4-carbonitrile [m.p. 190° to 192° C].

Replacing the carboxamide with an equivalent of each of:

3-(5-nitro-2-furyl)-1H-pyrazole-4-carboxamide,
1-methyl-3-(5-nitro-2-furyl)pyrazole-4-carboxamide,
1-methyl-5-(5-nitro-2-furyl)pyrazole-4-carboxamide,
1-isopropyl-3-(5-nitro-2-furyl)pyrazole-4-carboxamide,
1-(n-hexyl)-3-(5-nitro-2-furyl)pyrazole-4-carboxamide,
1-benzyl-3-(5-nitro-2-furyl)pyrazole-4-carboxamide,
1-allyl-3-(5-nitro-2-furyl)pyrazole-4-carboxamide, 1-cyclohexyl-3-(5-nitro-2-furyl)pyrazole-4-carboxamide,
1-(2-methoxyethyl)-3-(5-nitro-2-furyl)pyrazole-4-carboxamide,
1-(p-chlorophenyl)-3-(5-nitro-2-furyl)pyrazole-4-carboxamide,
1-(p-flurophenyl)-3-(5-nitro-2-furyl)pyrazole--carboxamide,
1-(3-chloro-p-tolyl)-3-(5-nitro-2-furyl)pyrazole-4-carboxamide,
1-(p-biphenylyl)-3-(5-nitro-2-furyl)pyrazole-4-carboxamide, and
3-(5-nitro-2-furyl)-1-(p-nitrophenyl)pyrazole-4-carboxamide results in the corresponding preparation of each of:

3-(5-nitro-2-furyl)-1H-pyrazole-4-carbonitrile [m.p. 237.5° to 239° C],
1-methyl-5-nitro-2-furyl)pyrazole-4-carbonitrile [m.p. 176.5° to 177.5° C],
1-methyl-5-(5-nitro-2-furyl)pyrazole-4-carbonitrile [m.p. 149.5° to 151.5° C],
1-isopropyl-3-(5-nitro-2-furyl)pyrazole-4-carbonitrile [m.p. 181° to 182° C],
1-(n-hexyl)-3-(5-nitro-2-furyl)pyrazole-4-carbonitrile,
1-benzyl-3-(5-nitro-2-furyl)pyrazole-4-carbonitrile [m.p. 111.5° to 113° C],
1-allyl-3-(5-nitro-2-furyl)pyrazole-4-carbonitrile [m.p. 86.5° to 88° C],
1-cyclohexyl-3-(5-nitro-2-furyl)pyrazole-4-carbonitrile,
1-(2-methoxyethyl)-3-(5-nitro-2-furyl)pyrazole-4-carbonitrile,
1-(p-chlorophenyl)-3-(5-nitro-2-furyl)pyrazole-4-carbonitrile [m.p. 188° to 190° C],
1-(p-fluorophenyl)-3-(5-nitro-2-furyl)pyrazole-4-carbonitrile [m.p. 169° to 170° C],
1-(3-chloro-p-tolyl)-3-(5-nitro-2-furyl)pyrazole-4-carbonitrile [m.p. 188° to 189° C],
1-(p-biphenylyl)-3-(5-nitro-2-furyl)pyrazole-4-carbonitrile, and
3-(5-nitro-2-furyl)-1-(p-nitrophenyl)pyrazole-4carbonitrile [m.p. 274.5° to 276° C (with decomposition)], respectively.

EXAMPLE 53

1-methyl-3-(5-nitro-2-furyl)pyrazole-4-carboxamide

While cooling and stirring 80 ml of concentrated sulfuric acid at room temperature, add 40 g of 1-methyl-3-(5-nitro-2-furyl)pyrazole-4-carbonitrile thereto. Then stir the resulting mixture for 21 hours at room temperature. Pour thus-obtained solution onto ice for a 97% yield of 1-methyl-3-(5-nitro-2-furyl)pyrazole-4-carboxamide [m.p. 251° to 252.5° C].

Replacing the carbonitrile with an equivalent of each of:

1-ethyl-3-(5-nitro-2-furyl)pyrazole-4-carbonitrile,
1-isopropyl-3-(5-nitro-2-furyl)pyrazole-4-carbonitrile,
1-methyl-5-(5-nitro-2-furyl)pyrazole-4-carbonitrile,
3-(5-nitro-2-furyl)-1H-pyrazole-4-carbonitrile,
1-isoamyl-3-(5-nitro-2-furyl)pyrazole-4-carbonitrile,
1-(n-hexyl)-3-(5-nitro-2-furyl)pyrazole-4-carbonitrile,
1-cyclohexyl-3-(5-nitro-2-furyl)pyrazole-4-carbonitrile,
1-allyl-3-(5-nitro-2-furyl)pyrazole-4-carbonitrile,
1-(2-methoxyethyl)-3-(5-nitro-2-furyl)pyrazole-4-carbonitrile,
1-benzyl-3-(5-nitro-2-furyl)pyrazole-4-carbonitrile,
1-(p-chlorophenyl)-3-(5-nitro-2-furyl)pyrazole-4-carbonitrile,
1-(p-chlorobenzyl)-3-(5-nitro-2-furyl)pyrazole-4-carbonitrile, and
3-(5-nitro-2-furyl)-1-phenylpyrazole-4-carbonitrile, and results in the corresponding preparation of each of:

1-ethyl-3-(5-nitro-2-furyl)pyrazole-4-carboxamide [m.p. 229° to 230° C (with decomposition) from ethanol/water],
1-isopropyl-3-(5-nitro-2-furyl)pyrazole-4-carboxamide [m.p. 192° to 193° C (with decomposition) from ethanol],
1-methyl-5-(5-nitro-2-furyl)pyrazole-4-carboxamide [m.p. 174° to 175.5° C],
3-(5-nitro-2-furyl)-1H-pyrazole-4-carboxamide,
1-isoamyl-3-(5-nitro-2-furyl)pyrazole-4-carboxamide,
1-(n-hexyl)-3-(5-nitro-2-furyl)pyrazole-4-carboxamide,
1-cyclohexyl-3-(5-nitro-2-furyl)pyrazole-4-carboxamide,
1-allyl-3-(5-nitro-2-furyl)pyrazole-4-carboxamide [m.p. 176.5° to 178° C],
1-(2-methoxyethyl)-3-(5-nitro-2-furyl)pyrazole-4-carboxamide,
1-benzyl-3-(5-nitro-2-furyl)pyrazole-4-carboxamide [m.p. 170° to 175° C (with decomposition)],
1-(p-chlorophenyl)-3-(5-nitro-2-furyl)pyrazole-4-carboxamide [m.p. 270° to 271° C (with decomposition)],
1-(p-chlorobenzyl-3-(5-nitro-2-furyl)pyrazole-4-carboxamide, and
3-(5-nitro-2-furyl)-1-phenylpyrazole-4-carboxamide [m.p. 236° to 238° C], respectively.

EXAMPLE 54

3-(5-nitro-2-furyl)-1-phenylpyrazole-4-carboxamide

Add 29.4 g of 3-(5-nitro-2-furyl)-1-phenylpyrazole-4-carbonitrile to 59 ml of concentrated sulfuric acid while stirring and maintaining the temperature at 40° C for 5 hours. Pour the solution onto 500 g of ice and water. Seperate the formed precipitate by vacuum filtration and wash it with water until it is neutral to obtain a 98% yield of 3-(5-nitro-2-furyl)-1-phenylpyrazole-4-carboxamide [m.p. 236° to 238° C (from dimethylformamide/methanol)].

EXAMPLE 55

Replacing the carbonitrile of Example 54 with an equivalent of each of:

1-(o-chlorophenyl)-3-(5-nitro-2-furyl)pyrazole-4-carbonitrile,
1-(m-chlorophenyl)-3-(5-2-furyl)pyrazole-4-carbonitrile,
1-(p-chlorophenyl)-3-(5-nitro-2-furyl)pyrazole-4-carbonitrile,
1-(p-fluorophenyl)-3-(5-nitro-2-furyl)pyrazole-4-carbonitrile,
1-(p-bromophenyl)-3-(5-nitro-2-furyl)pyrazole-4-carbonitrile,
1-(p-methoxyphenyl)-3-(5-nitro-2-furyl)pryazole-4-carbonitrile,
3-(5-nitro-2-furyl)-1-(p-nitrophenyl)pyrazole-4-carbonitrile,
3-(5-nitro-2-furyl)-1-(m-nitrophenyl)pyrazole-4-carbonitrile, 3-(5-nitro-2-furyl)-1-(α,α,α,-trifluoro-m-tolyl)pyrazole-4-carbonitrile,
3-(5-nitro-2-furyl)-1-(p-tolyl)pyrazole-4-carbonitrile,
1-(3-chloro-p-tolyl)-3-(5-nitro-2-furyl)pyrazole-4-carbonitrile,
1-(3,4-dichlorophenyl)-3-(5-nitro-2-furyl)pyrazole-4-carbonitrile,
1-(3,4-dimethoxyphenyl)-3-(5-nitro-2-furyl)pyrazole-4-carbonitrile,
1-(2-naphthyl)-3-(5-nitro-2-furyl)pyrazole-4-carbonitrile,
1-(p-biphenylyl)-3-(5-nitro-2-furyl)pyrazole-4-carbonitrile,
1-(5-indanyl)-3-(5-nitro-2-furyl)pyrazole-4-carbonitrile results in the corresponding preparation of each of:

1-(o-chlorophenyl)-3-(5-nitro-2-furyl)pyrazole-4-carboxamide [m.p. 218° to 219° C],
1-(m-chlorophenyl)-3-(5-nitro-2-furyl)pyrazole-4-carboxamide [m.p. 212° to 213° C],
1-(p-chlorophenyl)-3-(5-nitro-2-furyl)pyrazole-4-carboxamide [m.p. 270° to 271° C (with decomposition)],
1-(p-fluorophenyl)-3-(5-nitro-2-furyl)pyrazole-4-carboxamide [m.p. 226.5° to 228° C],
1-(p-bromophenyl)-3-(5-nitro-2-furyl)pyrazole-4-carboxamide [m.p. 283.5° to 285° C (with decomposition)],
1-(p-methoxyphenyl)-3-(5-nitro-2-furyl)pyrazole-4-carboxamide [m.p. 257° 259° C (with decomposition)],
3-(5-nitro-2-furyl)-1-(p-nitrophenyl)pyrazole-4-carboxamide [m.p. 284° to 285° C (with decomposition)],
3-(5-nitro-2-furyl)-1-(m-nitrophenyl)pyrazole-4-carboxamide [m.p. 264.5° to 266° C (with decomposition)],
3-(5-nitro-2-furyl)-1-(α,α,α,-trifluoro-m-tolyl)pyrazole-4-carboxamide,
3-(5-nitro-2-furyl)-1-(p-tolyl)-3-(5-nitro-2-furyl)-pyrazole-4-carboxamide [m.p. 242° to 244° C],
1-(3-chloro-p-tolyl)-3(5-nitro-2-furyl)pyrazole-4-carboxamide [m.p. 219° to 220° C],
1-(3,4-dichlorophenyl)-3-(5-nitro-2-furyl)pyrazole-4-carboxamide [m.p. 252.5° to 254.5° C],
1-(3,4-dimethoxyphenyl)-3-(5-nitro-2-furyl)pyrazole-4-carboxamide,
1-(2-naphthyl)-3-(5-nitro-2-furyl)pyrazole-4-carboxamide,
1-(p-biphenylyl)-3-(5-nitro-2-furyl)pyrazole-4-carboxamide, and
1-(5-indanyl)-3-(5-nitro-2-furyl)pyrazole-4-carboxamide, respectively.

EXAMPLE 56

3-(5-nitro-2-furyl)-1-phenylpyrazole-4-carboxamide

Add 10 g of 3-(5-nitro-2-furyl)-1-phenylpyrazole-4-carbonitrile to a mixture of 20 ml of concentrated sulfuric acid and 20 ml of ethanol. Heat the resulting reaction mixture for 1.5 hours in a water bath at 90° to 100° C. Pour the solution onto ice and water to obtain a 93% yield of 3-(5-nitro-2-furyl)-1-phenylpyrazole-4-carboxamide [m.p. 236° to 238° C (from dimethylformamide/methanol)].

EXAMPLE 57

3-(5-nitro-2-furyl)-1-phenylpyrazole-4-carboxamide

Heat 1 g of 3-(5-nitro-2-furyl)-1-phenylpyrazole-4-carboxylic acid together with 0.56 g of phosphorus oxychloride and 10 ml of dichloroethane for 2 hours at 80° C. Add 10 ml of a 25% aqueous solution dropwise at 0° C to the thus-obtained solution of 3-(5-nitro-2-furyl)-1-phenylpyrazole-4-carboxylic chloride. Allow the resulting mixture to stand overnight and then vacuum distil it to remove the organic solvent therefrom. Vacuum filter to separate formed precipitate and recrystallize the filter residue from dimethylformamide/methanol to obtain 3-(5-nitro-2-furyl)-1-phenylpyrazole-4-carboxamide [m.p. 236° to 238° C].

EXAMPLE 58

3-(5-nitro-2-furyl)-1-phenylpyrazole-4-carboxylic acid

Add 2 g of 3-(5-nitro-2-furyl)-1-phenylpyrazole-4-carboxamide to 4.7 ml of concentrated sulfuric acid while cooling on ice and then add thereto a solution of 0.78 g of sodium nitrite in 2 ml of water slowly and dropwise at a temperature not exceeding 7° C. Allow the resulting mixture to stand overnight; dilute with from 4 to 5 ml of concentrated sulfuric acid and then mix it (while cooling with ice) with 0.39 g of sodium nitrite in 1 ml of water. Allow the thus-prepared solution to stand at a temperature of 0° to 5° C for 2 days in a refrigerator and then pour it onto ice. Vacuum filter to separate formed precipitate and chromatograph with chloroform/ethanol (9:1) on a silica gel column to obtain 3-(5-nitro-2-furyl)-1-phenylpyrazole-4-carboxylic acid [m.p. 250° to 252° C].

EXAMPLE 59

[3-(5-nitro-2-furyl)-1-phenylpyrazol-4-ylmethylene]-dimethylammonium perchlorate Prepare the Vilsmeier complex from 20.8 ml of dimethylformamide and 8.3 g of phosphorus oxychloride. Add thereto 6 g of 5-nitro-2-acetylfuran-phenylhydrazone at from 30° to 40° C. Stir the resulting reaction mixture for 2.5 hours at 50° C and then allow it to stand overnight. Add thereto 26 ml of methanol before precipitating the title compound by adding (at room temperature) a solution of 3.44 g of sodium perchlorate monohydrate in 22 ml of methanol. Cool the thus-prepared admixture in an ice bath. Vacuum filter to separate the formed precipitate, and wash the precipitate with methanol and water to obtain an 83% yield of [3-(5-nitro-2-furyl)-1-phenylpyrazol-4-ylmethylene]-dimethylammonium perchlorate [m.p. 242° to 244° C (with decomposition)].

Replacing the hydrazone by an equivalent of each of:

5-nitro-2-acetylfuran-methoxycarbonylhydrazone [m.p. 179° to 180° C],
5-nitro-2-acetylfuran-p-chlorophenylhydrazone [m.p. 138° to 140° C (with decomposition)],
5-nitro-2-acetylfuran-p-fluorophenylhydrazone [m.p. 174° to 176° C (with decomposition)],
5-nitro-2-acetylfuran-p-methoxyphenylhydrazone [m.p. 164.5° to 166° C (with decomposition)],
5-nitro-2-acetylfuran-p-tolylhydrazone [m.p. 150.5° to 152.5° (with decomposition)]

results in the corresponding preparation of

[1-methoxycarbonyl-3-(5-nitro-2-furyl)pyrazol-4-ylmethylene]dimethylammonium perchlorate,
[1-(p-chlorophenyl)-3-(5-nitro-2-furyl)pyrazol-4-ylmethylene]dimethylammonium perchlorate,
[1-(p-fluorophenyl)-3-(5-nitro-2-furyl)pyrazol-4-ylmethylene]dimethylammonium perchlorate,

[1-(p-methoxyphenyl)-3-(5-nitro-2-furyl)pyrazol-4-ylmethylene]dimethylammonium perchlorate, and
[3-(5-nitro-2-furyl)-1-(p-tolyl)pyrazol-4-ylmethylene]-dimethylammonium perchloroate, respectively.

EXAMPLE 60

3-(5-nitro-2-furyl)-1-phenylpyrazole-4-carboxaldehyeethoxycarbonylhydrazone

Add 2.0 g of [3-(5-nitro-2-furyl)-1-phenylpyrazol-4-ylmethylene]dimethylammonium perchlorate, 0.4 g. of anhydrous sodium acetate and 0.63 g of ethyl carbazate to 10.5 ml of dimethylformamide. Stir the resulting admixture for 30 minutes before adding 30 ml of water dropwise thereto to obtain a 95% yield of 3-(5-nitro-2-furyl)-1-phenylpyrazole-4-carboxaldehyde-ethoxycarbonylhydrazone [m.p. 200° to 201° C].

Repeating the same procedure with an equivalent of the corresponding 4-pyrazolymethylene-dimethylammonium perchlorate results in the similar preparation of each of:

1-(p-chlorophenyl)-3-(5-nitro-2-furyl)pyrazole-4-carboxaldehyde-ethoxycarbonylhydrazone [m.p. 221° to 223° C (with decomposition)],
1-(p-methoxyphenyl)-3-(5-nitro-2-furyl)pyrazole-4-carboxaldehyde-ethoxycarbonylhydrazone [m.p. 198° to 199° C (with decomposition)],
1-(p-fluorophenyl)-3-(5-nitro-2-furyl)pyrazole-4-carboxaldehyde-ethoxycarbonylhydrazone [m.p. 215° to 216° C (with decomposition)], and
3-(5-nitro-2-furyl)-1-(p-tolyl)pyrazole-4-carboxaldehyde-ethoxycarbonylhydrazone [m.p. 210° to 211° C (with decomposition)].

EXAMPLE 61

3-(5-nitro-2-furyl)-1-phenylpyrazole-4-carboxaldehydeoxime

Add 2.0 g of [3-(5-nitro-2-furyl)-1-phenylpyrazol-4-ylmethylene]dimethylammonium perchlorate, 0.42 g of anhydrous sodium acetate and 0.36 g of hydroxylamine hydrochloride to 11 ml of dimethylformamide. Stir the resulting admixture for 2 hours at room temperature before adding 30 ml of water dropwise thereto to precipitate the title compound for a 95% yield of 3-(5-nitro-2-furyl)-1-phenylpyrazole-4-carboxaldehydeoxime [m.p. 199° to 201° C (with decomposition)].

Repeating the same procedure with an equivalent of the corresponding 4-pyrazolylmethylene-dimethylammonium perchlorate results in the similar preparation of:

1-(p-chlorophenyl)-3-(5-nitro-2-furyl)pyrazole-4-carboxaldehydeoxime [m.p. 216° to 218° C (with decomposition)],
1-(p-methoxyphenyl)-3-(5-nitro-2-furyl)pyrazole-4-carboxaldehydeoxime [m.p. 209° to 210° C (with decomposition)],
1-(p-fluorophenyl)-3-(5-nitro-2-furyl)pyrazole-4-carboxaldehydeoxime [m.p. 202° to 204° (with decomposition)], and
3-(5-nitro-2-furyl)-1-(p-tolyl)pyrazole-4-carboxaldehydeoxime [m.p. 211° to 212.5° C].

EXAMPLE 62

3-(5-nitro-2-furyl)-1-phenylpyrazole-4-carboxaldehydeoxime

Add 6.9 g of phosphorus oxychloride dropwise to 17.3 ml of dimethylformamide at from 15° to 20° C. Stir the resulting admixture for 30 minutes before adding 5.2 g of 5-nitro-2-acetylfuran-phenylhydrazone thereto. Then stir for 2 hours at 50° C and allow the reaction mixture to stand overnight. Add 10 g of sodium acetate together with 3 g of hydroxylamine hydrochloride to the thus-obtained mixture and then stir it for 4 hours at 40° C before pouring it onto ice and water. Recrystallize the formed precipitate from dimethylformamide and water to obtain an 85% yeild of 3-(5-nitro-2-furyl)-1-phenylpyrazole-4-carboxaldehydeoxime [m.p. 199° to 201° C (with decomposition)].

Replacing the hydrazone with an equivalent of 5-nitro-2-acetylfuran-p-chlorophenylhydrazone or 5-nitro-2-acetylfuran-p-methoxyphenylhydrazone results in the corresponding preparation of 1-(p-chlorophenyl)-3-(5-nitro-2-furyl)pyrazole-4-carboxaldehydeoxime [m.p. 216° to 218° C (with decomposition)] or
1-(p-methoxyphenyl)-3-(5-nitro-2-furyl)pyrazole-4-carboxaldehydeoxime [m.p. 209° to 210° C (with decomposition)], respectively.

EXAMPLE 63

3-(5-nitro-2-furyl)-1H-pyrazole-4-carboxaldehyde-ethoxycarbonylhydrazone

Replacing the carboxaldehyde of Example 41 with an equivalent of 3-(5-nitro-2-furyl)-1H-pyrazole-4-carboxaldehyde-ethyleneacetal results in the corresponding preparation of 3-(5-nitro-2-furyl)-1H-pyrazole-4-carboxaldehyde, ethoxycarbonylhydrazone [m.p. 257° (with decomposition)].

EXAMPLE 64

1-methyl-3-(5-nitro-2-furyl)pyrazole-4-carboxaldehyde-3-quinolylhydrazone

Heat 2.0 g of 1-methyl-3-(5-nitro-2-furyl)pyrazole-4-carboxaldehyde together with 2.5 g of 3-hydrazinoquinoline dihydrochloride and 1.8 g of anhydrous sodium acetate in 40 ml of ethanol for 3 hours at boiling point and then allow the resulting admixture to stand overnight. Separate the formed precipitate by filtration and stir it up with a little water to obtain an 86% yield of 1-methyl-3-(5-nitro-2-furyl)pyrazole-4-carboxaldehyde-3-quinolylhydrazone [m.p. 236° to 238° C (with decomposition)].

Following the same procedure 3-(5-nitro-2-furyl)-1-phenylpyrazole-4-carboxaldehyde-3-quinolylhydrazone [m.p. 217° to 219° C (with decomposition)] is similarly prepared from equivalent amounts of corresponding reactants.

EXAMPLE 65

Following the procedure of Example 28 and similarly reacting an equivalent of
1-methyl-3-(5-nitro-2-furyl)pyrazole-4-carboxaldehyde or
3-(5-nitro-2-furyl)-1-phenylpyrazole-4-carboxaldehye with 2-hydrazinobenzthiazole results in the corresponding preparation of 1-methyl-3-(5-nitro-2-furyl)pyrazole-4-carboxaldehyde-2-benzthiazolylhydrazone [m.p. 228° to 230° C (with decomposition)] or
3-(5-nitro-2-furyl)-1-phenylpyrazole-4-carboxaldehyde-2-benzthiazolylhydrazone [m.p. 225° to 227° C (with decomposition)], respectively.

EXAMPLE 66

1-methyl-5-(5-nitro-2-furyl)pyrazole-4-carbonitrile

Following the procedure of Example 21, react 1.3 g of 5-(2-furyl)-1-methylpyrazole-4-carbonitrile [German Offenlegungsschrift (DOS) 1,809,386] with 11.5 ml of acetic anhydride and 3 ml of 65% nitric acid to obtain 1-methyl-5-(5-nitro-2-furyl)pyrazole-4-carbonitrile [m.p. 149.5° to 151.5° C].

EXAMPLE 67

1-methyl-3-(5-nitro-2furyl)pyrazole-4-carboxaldehyde

Stir 10 g of 1-methyl-3-(5-nitro-2-furyl)pyrazole-4-carboxaldehydeethoxycarbonylhydrazone into 120 g of 67% sulfuric acid and continue stirring for 4 hours at room temperature. Pour the obtained mixture onto 160 g of ice and water for a 93% yield of 1-methyl-3-(5-nitro-2-furyl)pyrazole-4-carboxaldehyde [m.p. 183° to 184.5° C].

This carboxaldehyde is similarly obtained by the corresponding hydrolysis of each of:

1-methyl-3-(5-nitro-2-furyl)pyrazole-4-carboxaldehyde-dimethylhydrazone,
1-methyl-3-(5-nitro-2-furyl)pyrazole-4-carboxaldehyde-isonicotinoylhydrazone,
1-methyl-3-(5-nitro-2-furyl)pyrazole-4-carboxaldehyde-2-pyridylhydrazone,
1-methyl-3-(5-nitro-2-furyl)pyrazole-4-carboxaldehydeoxime, and
1-methyl-3-(5-nitro-2-furyl)pyrazole-4-carboxaldehyde-(0-acetyl)oxime.

EXAMPLE 68

3-(5-nitro-2-furyl)-1-(2-pyridyl)pyrazole-4-carboxaldehyde

Add 9.4 g of phosphorus oxychloride dropwise to 16.4 g of anhydrous dimethylformamide at from 10° to 20° C and then stir the obtained reaction mixture for 30 minutes at room temperature before adding thereto (from 35° to 40° C) 5.0 g of 5-nitro-2-acetylfuran-(2-pyridyl)hydrazone. Stir the thus-prepared admixture for 28 hours under nitrogen at this temperature and then pour it and a solution comprising 4-pyrazolylmethylenedimethylammonium salt onto 250 g of ice and water. Heat the resulting reaction mixture for 2 hours at from 30° to 40° C, draw off the formed precipitate and wash the precipitate with water to obtain a 45% yield of 3-(5-nitro-2-furyl)-1-(2-pyridyl)pyrazole-4-carboxaldehyde [m.p. 191° to 191.5° C (from toluene)].

Heat 6.8 g of 5-nitro-2-acetylfuran together with 5 g of 2-hydrazinopyridine, 2.8 ml of glacial acetic acid and 16 ml of ethanol under nitrogen to prepare 5-nitro-2-acetylfuran-(2-pyridyl)hydrazone [m.p. 163° to 165° C (with decomposition)].

EXAMPLE 69

3-(5-nitro-2-furyl)-1-(3-pyridyl)pyrazole-4-carboxaldehyde

Add 14.2 g of phosphorus oxychloride dropwise to 44 g of anhydrous dimethylformamide and then stir the resulting reaction mixture for 15 minutes at room temperature and then add thereto 10.3 g of 5-nitro-2-acetylfuran-(3-pyridyl)hydrazone. Stir the thus-prepared admixture at from 60° to 70° C for 5 days and then pour the obtained solution onto 500 g of ice and water. Adjust its pH-value to 6.5 with concentrated caustic soda. Chromatograph the produced precipitate (yield 69% of the theory) on a silica gel column with chloroform/ethanol (20:1) and recrystallize from dimethylformamide/methanol to obtain 3-(5-nitro-2-furyl)-1-(3-pyridyl)pyrazole-4-carboxaldehyde [m.p. 237° to 238° C].

Following the procedure of Example 68, 5-nitro-2-acetylfuran-(3-pyridyl)hydrazone [m.p. 236° to 237° C (with decomposition)] is prepared from equivalent amounts of corresponding reactants.

EXAMPLE 70

3-(5-nitro-2-furyl)-1-(2-pyridyl)pyrazole-4-carbo. 'ehyde-ethoxycarbonylhydrazone Heat 0.6 g of 3-(5-nitro-2-furyl)-1-(2-pyridyl)-pyrazole-4-carboxaldehyde together with 0.27 g of ethylcarbazate and 2 drops of glacial acetic acid in 8 ml of ethanol for 1.5 hours at boiling point. Cool the resulting product for a 97% yield of 3-(5-nitro-2-furyl)-1-(2-pyridyl)pyrazole-4-carboxaldehyde-ethoxycarbonylhydrazone [m.p. 215° to 216° C (with decomposition) from toluene].

Replacing the carboxaldehyde with an equivalent of 3-(5-nitro-2-furyl)-1-(3-pyridyl)pyrazole-4-carboxaldehyde results in the corresponding preparation of 3-(5-nitro-2-furyl)-1-(3-pyridyl)pyrazole-4-carboxaldehyde-ethoxycarbonylhydrazone [m.p. 213° to 214° C (with decomposition) from dioxane/methanol].

Following the same procedure and similarly reacting an equivalent of 3-(5-nitro-2-furyl)-1-(2-pyridyl)-pyrazole-4-carboxaldehyde or of 3-(5-nitro-2-furyl)-1-(3-pyridyl)pyrazole-4-carboxaldehyde with methyl carbazate results in the corresponding preparation of 3-(5-nitro-2-furyl)-1-(2-pyridyl)pyrazole-4-carboxaldehyde-methoxycarbonylhydrazone or
3-(5-nitro-2-furyl)-1-(3-pyridyl)pyrazole-4-carboxaldehyde-methoxycarbonylhydrazone, respectively.

EXAMPLE 71

3-(5-nitro-2-furyl)-1-(2-pyridyl)pyrazole-4-carboxaldehydeoxime

Add 1.18 g of anhydrous sodium acetate and 1.0 g of hydroxylamine hydrochloride to 3.9 g of 3-(5-nitro-2-furyl)-1-(2-pyridyl)pyrazole-4-carboxaldehyde in 12 ml of dimethylformamide, whereupon the temperature of the formed mixture rises slightly. Stir the resulting mixture at room temperature for 4 hours before pouring onto ice and water to obtain a 99% yield of 3-(5-nitro-2-furyl)-1-(2-pyridyl)pyrazole-4-carboxaldehydeoxime [m.p. 234.5° to 235° C].

Replacing the carboxaldehyde with an equivalent of 3-(5-nitro-2furyl)-1-(3-pyridyl)pyrazole-4-carboxaldehyde results in the corresponding preparation of 3-(5-nitro-2-furyl)-1-(3-pyridyl)pyrazole-4-carboxal-

EXAMPLE 72

3-(5-nitro-2-furyl)-1-(2-pyridyl)pyrazole-4-carbonitrile

Add 1.02 ml of thionyl chloride dropwise to a suspension of 3.6 g of finely-ground 3-(5-nitro-2-furyl)-1-(2pyridyl)pyrazole-4-carboxaldehydeoxime in 36 ml of carbon tetrachloride at from 60° to 65° C.

Stir the resulting reaction mixture for 40 minutes at 65° C and for 3 hours at boiling temperature. Then cool down to room temperature and vacuum filter to obtain 3-(5-nitro-2-furyl)-1-(2-pyridyl)pyrazole-4-carbonitrile [m.p. 207° to 208° C (from dimethylformamide/methanol)] in a quantitative yield.

Replacing the carboxaldehydeoxime with an equivalent of 3-(5-nitro-2-furyl)-1-(3-pyridyl)pyrazole-4-carboxaldehydeoxime results in the corresponding preparation of 3-(5-nitro-2-furyl)-1-(3-pyridyl)pyrazole-4-carbonitrile [m.p. 206° to 207° C].

EXAMPLE 73

3-(5-nitro-2-furyl)-1-(2-pyridyl)pyrazole-4-carboxamide

Stir 2.3 g of 3-(5-nitro-2-furyl)-1-(2-pyridyl)pyrazole-4-carbonitrile with 4.4 ml of concentrated sulfuric acid for 15 hours at from 35° to 40° C. Pour the resulting solution onto 75 g of ice and water; separate the formed precipitate and wash it with water until it is no longer acid to obtain a 97% yield of 3-(5-nitro-2-furyl)-1-(2-pyridyl)pyrazole-4-carboxamide [m.p. 249.5° to 250.5° C (from dimethylformamide/methanol)].

Hydrolyzing 3-(5-nitro-2-furyl)-1-(3-pyridyl)-pyrazole-4-carbonitrile in a similar manner for 6 hours with concentrated sulfuric acid yields 3-(5-nitro-2-furyl)-1-(3-pyridyl)pyrazole-4-carboxamide ]m.p. 267° to 268° C (with decomposition)].

EXAMPLE 74

3-(5-nitro-2-furyl)-1-phenylpyrazole-4-carboxylic acid

Add 36 g of 98% nitrosylsulfuric acid (under cooling with ice) dropwise to a suspension of 50 g 3-(5-nitro-2-furyl)-1-phenylpyrazole-4-carboxamide in 830 ml of 89% orthophosphoric acid, whereupon the temperature rises from 0° C to 35° C. Stir the resulting reaction mixture for 18 hours at room temperature and pour the produced solution onto 5 kg of ice and water. Separate the formed precipitate and wash it with water until it is no longer acid to obtain a 98% yield of 3-(5-nitro-2-furyl)-1-phenylpyrazole-4-carboxylic acid [m.p. 264° to 265.5° C (with decomposition) from dioxane].

Replacing the carboxamide with an equivalent of each of 3-(5-nitro-2-furyl)-1-(p-fluorophenyl)pyrazole-4-carboxamide, 3-(5-nitro-2-furyl)-1-(p-chlorophenyl)pyrazole-4-carboxamide, 3-(5-nitro-2-furyl)-1-(2-pyridyl)pyrazole-4-carboxamide, and 1-methyl-3-(5-nitro-2-furyl)pyrazole-4-carboxamide results in the corresponding preparation of:

3-(5-nitro-2-furyl)-1-(p-fluorophenyl)pyrazole-4-carboxylic acid, 3-(5-nitro-2-furyl)-1-(p-chlorophenyl)pyrazole-4-carboxylic acid, 3-(5-nitro-2-furyl)-1-(2-pyridyl)pyrazole-4-carboxylic acid, and 1-methyl-3-(5-nitro-2-furyl)pyrazole-4-carboxylic acid, respectively.

EXAMPLE 75

3-(5-nitro-2-furyl)-1-phenylpyrazole-4-carboxylic acid chloride

Heat 40 g of 3-(5-nitro-2-furyl)-1-phenylpyrazole-4-carboxamide together with 290 ml of thionyl chloride and 1 ml of dimethylformamide for 16 hours at boiling point. Cool the resulting solution, draw off the formed precipitate and wash it with thionyl chloride and with carbon tetrachloride to obtain an 89% yield of 3-(5-nitro-2-furyl)-1-phenylpyrazole-4-carboxylic acid chloride [m.p. 208° to 210° C (from dioxane)].

EXAMPLE 76

3-(5-nitro-2-furyl)-1-phenylpyrazole-4-carboxylic acid azide

At from 23° to 30° C add a warm solution of 7.5 g of 3-(5-nitro-2-furyl)-1-phenylpyrazole-4-carboxylic acid chloride in 200 ml of acetone and 250 ml of dioxane dropwise to a solution of 1.84 g of sodium azide in 24 ml of water. Stir the resulting reaction mixture for a further 15 minutes and then dilute it with 600 ml of water cooling with ice to obtain a 98% yield of 3-(5-nitro-2-furyl)-1-phenylpyrazole-4-carboxylic acid azide [m.p. 134° C (with decomposition)].

EXAMPLE 77

3-(5-nitro-2-furyl)-1-phenylpyrazole-4-carboxylic acid anhydride

Add a solution of 0.64 g of 3-(5-nitro-2-furyl)-1-phenylpyrazole-4-carboxylic acid chloride dropwise to a warm solution of 0.60 g of 3-(5-nitro-2-furyl)-1-phenylpyrazole-4-carboxylic acid in 10 ml of dioxane and 0.48 ml of pyridine at 40° C. Stir the resulting reaction mixture at from 45° to 50° C for 6 hours. Draw off the formed precipitate and recrystallize it from dimethylformamide to obtain 3-(5-nitro-2-furyl)-1-phenylpyrazole-4-carboxylic acid anhydride [m.p. 262° to 264° C].

EXAMPLE 78

Methyl-[3-(5-nitro-2-furyl)-1-phenylpyrazole]-4-carboxylate

Heat a mixture of 0.6 g of 3-(5-nitro-2-furyl)-1-phenylpyrazole-4-carboxylic acid chloride with 15 ml of methanol and 2 ml of pyridine for 2.5 hours at boiling point. Pour the thus-formed mixture onto ice to obtain methyl-[3-(5-nitro-2-furyl)-1-phenylpyrazole-4-carboxylate [m.p. 193° to 194.5° C (from dimethylformamide)] in a quantitative yield.

In a similar manner from the acid chloride and ethanol or phenol ethyl-[3-(5-nitro-2-furyl)-1-phenylpyrazole]-4-carboxylate (m.p. 165.5° to 166.5° C) and phenyl-[3-(5-nitro-2-furyl)-1-phenylpyrazole]-4-carboxylate (m.p. 220.5° to 221.5° C) are obtained.

EXAMPLE 79

1-[3-(5-nitro-2-furyl)-1-phenyl-4-pyrazolylcarbonyl]-pyrrolidine

Add 1.06 ml. of pyrrolidine in 2 ml of dioxane dropwise to 1.0 g of 3-(5-nitro-2-furyl)-1-phenylpyrazole-4-carboxylic acid chloride in 43 ml of dioxane at 35° C under stirring. Stir the resulting solution for an hour at room temperature and then concentrate it. Wash the resulting precipitate with water to obtain a 99% yield of 1-[3-(5-nitro-2-furyl)-1-phenyl-4-pyrazolylcarbonyl]-pyrrolidine [m.p. 236.5° to 237.5° C].

Replacing the pyrrolidine with an equivalent of each of ammonia, methylamine, dimethylamine, n-butylamine, ethanolamine, diethanolamine, morpholine, piperidine and aniline results in the corresponding preparation of:

3-(5-nitro-2-furyl)-1-phenylpyrazole-4-carboxamide [m.p. 236° to 238° C],
N-methyl-3-(5-nitro-2-furyl)-1-phenylpyrazole-4-carboxamide ]m.p. 215° to 217° C],
N,N-dimethyl-3-(5-nitro-2-furyl)-1-phenylpyrazole-4-carboxamide [m.p. 204° to 205.5° C],
N-n-butyl-3-(5-nitro-2-furyl)-1-phenylpyrazole-4-carboxamide [m.p. 165.5° to 166.5° C],
N-(2-hydroxyethyl)-3-(5-nitro-2-furyl)-1-phenyl-pyrazole-4-carboxamide [m.p. 180° to 181° C],
N,N-bis-(2-hydroxyethyl)-3-(5-nitro-2-furyl)-1-phenyl-pyrazole-4-carboxamide [m.p. 170.5° to 173° C],
4-[3-(5-nitro-2-furyl)-1-phenyl-4-pyrazolylcarbonyl]-morpholine [m.p. 238° to 239° C],
1-[3-(5-nitro-2-furyl)-1-phenyl-4-pyrazolylcarbonyl]-piperidine [m.p. 187.5° to 189° C], and
3-(5-nitro-2-furyl)-1,N-diphenylpyrazole-4-carboxamide [m.p. 227° to 228° C], respectively.

EXAMPLE 80

N,N'-bis-[3-(5-nitro-2-furyl)-1-phenyl-4-pyrazolylcarbonyl]hydrazine

Add a solution of 476 mg of 3-(5-nitro-2-furyl)-1-phenylpyrazole-4-carboxylic acid chloride in 25 ml of dioxane dropwise to 210 mg of hydrazine dihydrochloride in 2 ml of water, whereupon N,N'-bis-[3-(5-nitro-2-furyl)-1-phenyl-4-pyrazolylcarbonyl]hydrazine [m.p. 313° to 314° C (with decomposition) from dimethylformamide] precipitates with a yield of 72%.

EXAMPLE 81

3-(5-nitro-2-furyl)-1-phenylpyrazole-4-carbohydrazide

Stir 0.40 g of phenyl-[3-(5-nitro-2-furyl)-1-phenylpyrazole]-4-carboxylate with 0.06 ml of hydrazine hydrate and 6 ml of dioxane at 50° C for 7 hours. Concentrate the thus-prepared solution, add water thereto to effect precipitation and chromatograph on silica gel with benzene/ethanol (9:1) to obtain [3-(5-nitro-2-furyl)-1-phenyl-4-pyrazolylcarbonyl]hydrazine [m.p. 285° to 286° C (with decomposition)].

EXAMPLE 82

3-(5-nitro-2-furyl)-1,N'-diphenylpyrazole-4-carbohydrazide

Add a solution of 1.0 g of 3-(5-nitro-2-furyl)-1-phenylpyrazole-4-carboxylic acid chloride in 50 ml of pyridine dropwise to a solution of 0.31 ml of phenyl hydrazine in 5 ml of pyridine and stir the resulting reaction mixture at room temperature for 4 hours. Pour the thus-produced solution onto ice and water and chromatograph on silica gel with benzene/ethanol (9:1) to obtain 3-(5-nitro-2-furyl)-1,N'-diphenylpyrazole-4-carbohydrazide.

EXAMPLE 83

3-(5-nitro-2-furyl)-1-phenylpyrazole-4-carboxaldehyde

Heat 0.42 g of 4-hydroxymethyl-3-(5-nitro-2-furyl)-1-phenylpyrazole with 1.3 g of activated manganese dioxide and 6 ml of chloroform for 4 hours at boiling with removal of water. Filter while warm and extract the filter residue three times by boiling with chloroform. Concentrate the produced organic solutions to obtain 3-(5-nitro-2-furyl)-1-phenylpyrazole-4-carboxaldehyde [m.p. 208° to 209° C].

To obtain the starting material, stir 1.2 ml of a 70% solution of sodium dihydro-bis-(2-methoxyethoxy)aluminate together with 0.6 g of 3-(5-nitro-2-furyl)-1-phenylpyrazole-4-carboxylic acid and 15 ml of dioxane at 70° C for 1.5 hours. Then add thereto 0.16 ml of 15% caustic soda and 0.5 ml of water at room temperature before filtering the thus-prepared product while warm. Extract the filtered precipitate with dioxane, concentrate the combined dioxane solutions and crystallize from ethanol to obtain 4-hydroxymethyl-3-(5-nitro-2-furyl)-1-phenylpyrazole [m.p. 148° to 149° C].

Following the same procedure 1-methyl-3-(5-nitro-2-furyl)pyrazole-4-carboxaldehyde [m.p. 183° to 184° C] is prepared from 4-hydroxymethyl-1-methyl-3-(5-nitro-2-furyl)pyrazole [m.p. 171.5° to 172.5° C].

EXAMPLE 84

3-(5-nitro-2-furyl)-1-phenylpyrazole-4-carbonitrile

Add a solution of 0.25 g of 4-amino-3-(5-nitro-2-furyl)-1-phenylpyrazole hydrochloride in 2 ml of pyridine dropwise over a period of from 1 to 2 hours to a solution of 0.22 g of sodium nitrite in 3 ml of concentrated sulfuric acid and 1.75 ml of water at 0° C. Stir the resulting reaction mixture for 0.5 hour, and then precipitate the diazonium salt by adding ice and water to the reaction mixture. Add the precipitate to a heated (90° C) solution of 300 mg of potassium cyanide and 200 ml of copper(I)cyanide in 20 ml of water. Stir the prepared admixture for 15 minutes at 90° C, cool down, draw off the formed precipitate and chromatograph with methylene chloride on silica gel to obtain 3-(5-nitro-2-furyl)-1-phenylpyrazole-4-carbonitrile [m.p. 190° to 192° C].

To prepare the starting material, heat 1 g of 4-(5-nitro-2-furyl)-1-phenylpyrazole-4-carboxylic acid azide in 15 ml of absolute dioxane for 1 hour at 90° C. After gas formation has finished, add the solution of the produced [3-(5-nitro-2-furyl)-1-phenyl-4-pyrazolyl]isocyanate dropwise to 4 ml of concentrated hydrochloric acid and then stir the resulting admixture overnight at from 40° to 45° C. Cool the thus-prepared material and draw off the formed precipitate to obtain 4-amino-3-(5-nitro-2-furyl)-1-phenylpyrazole hydrochloride [m.p. 211° to 213° C (with decomposition)] with the yield of 88%.

EXAMPLE 85

1-methyl-5-(5-nitro-2-furyl)pyrazole-4-carbonitrile

Add 1.0 g of 5-(2-furyl)-1-methylpyrazole-4-carbonitrile to 4.1 ml of concentrated sulfuric acid at from −10° C to −12° C and, at the same temperature, slowly add a nitrating mixture (0.91 ml of concentrated sulfuric acid and 0.45 ml of fuming nitric acid) dropwise to the resulting reaction mixture for 1 hour at this temperature, and then pour the prepared solution onto 20 g of ice and water. Crystallize the thus-prepared precipitate in an ice-bath to obtain an 80% yield of 1-methyl-5-(5-nitro-2-furyl)pyrazole-4-carbonitrile [m.p. 149.5° to 151.5° C].

Replacing the carbonitrile with an equivalent of 3-(2-furyl)-1-methylpyrazole-4-carbonitrile or 5-(2-furyl)-1-methylpyrazole-4-carboxamide results in the corresponding preparation of 1-methyl-3-(5-nitro-2-furyl)-pyrazole-4-carbonitrile [m.p. 251° to 252.5° C] or 1-methyl-5-(5-nitro-2-furyl)pyrazole-4-carboxamide [m.p. 174° to 175.5° C]., respectively.

To prepare starting materials, (a) Heat 10 g of 2-furoylacetonitrile together with 36 g of diethoxymethylacetate and 23 g of acetic acid anhydride for 4 hours at 100° C. Concentrate the resulting mixture and triturate it with ether to obtain a product [m.p. 55.5° to 56.5° C].

(b) Add 5.0 ml of methylhydrazine dropwise to 12 g of 3-ethoxy-2-(2-furoyl)acrylonitrile and 7.9 g of oxalic acid in 190 ml of ethanol at room temperature. Heat the resulting solution for 2 hours at boiling point. Then filter, reduce the filtered solution to dryness and chromatograph on a silica gel column with chloroform/ethyl acetate (9:1) to obtain 4.6 g of 5-(2-furyl)-1-methylpyrazole-4-carbonitrile (compare German Offenlegungsschrift No. 1,809,386) and 3.3 g of 3-(2-furyl)-1-methylpyrazole-4-carbonitrile [m.p. 104.5° to 106° C].

(c) Stir 1.1 g of 5-(2-furyl)-1-methylpyrazole-4-carbonitrile together with 7 ml of concentrated sulfuric acid for 24 hours at room temperature. Pour the resulting mixture onto ice and adjust its pH-value to 4 with caustic soda. Then extract it with methylene chloride and reduce the organic phase to dryness to obtain 5-(2-furyl)-1-methylpyrazole-4-carboxamide [m.p. 115.5° to 116° C (from ethanol)] with a yield of 91%.

EXAMPLE 86

Vaginal Tablets with 150 mg of Active Substance

| | | |
|---|---|---|
| (1) | 3-(5-nitro-2-furyl)-1-phenylpyrazole-4-carboxamide | 15 kg |
| (2) | lactose | 84 kg |
| (3) | carboxymethylcellulose | 17 kg |
| (4) | talcum | 4 kg |
| | | 120 kg |

Mix components 1, 2 and 3. Moisten the resulting mixture with 30 liters of water and then granulate through a sieve with a clearance mesh width of 1.5 mm. After drying the obtained granulate in a fluidized bed drier to a relative moisture of from 50 to 60% by weight, mix the thus-dried granulate with component 4; then sieve and press to tablets with a weight of 1200 mg each.

EXAMPLE 87

Tablets with 150 mg of Active Substance for Oral Application

| | | |
|---|---|---|
| (1) | 3-(5-nitro-2-furyl)-1-phenylpyrazole-4-carboxamide | 60 kg |
| (2) | lactose | 12 kg |
| (3) | maize starch | 8 kg |
| (4) | polyvinylpyrrolidone | 4 kg |
| (5) | sodium carboxymethyl starch | 10 kg |
| (6) | talcum | 4 kg |
| (7) | magnesium stearate | 2 kg |
| | | 100 kg |

Moisten an admixture of components 1, 2 and 3 with 4 in approximately 20 liters of water and granulate with a sieve having a clearance mesh width of 1.25 mm. Dry the granulate in a fluidized bed drier down to a relative moisture of from 50 to 60% by weight and then add components 5, 6 and 7. After sieving the mixture, press it to tablets having a diameter of 9 mm and a weight of 250 mg, each.

EXAMPLE 88

Vaginal Tablets with 50 mg of Active Substance

| | | |
|---|---|---|
| (1) | 1-methyl-(5-nitro-2-furyl)pyrazole-4-carboxaldehyde-ethoxycarbonylhydrazone | 5 kg |
| (2) | lactose | 94 kg |
| (3) | carboxymethylcellulose | 17 kg |
| (4) | talcum | 4 kg |
| | | 120 kg |

Moisten a mixture of components, 1, 2 and 3 with 30 liters of water and then granulate through a sieve with a clearance mesh width of 1.5 mm. Dry the resulting granulate down to a relative moisture of 50 to 60% by weight in a fluidized bed drier. Mix the dried granulates with component 4, sieve and press to tablets having a weight of 1200 mg, each.

EXAMPLE 89

Tablets with 50 mg of Active Substance for Oral Administration

| | | |
|---|---|---|
| (1) | 1-methyl-(5-nitro-2-furyl)pyrazole-4-carboxaldehyde-ethoxycarbonylhydrazone | 25 kg |
| (2) | lactose | 35 kg |
| (3) | maize starch | 26 kg |
| (4) | polyvinylpyrrolidone | 3 kg |
| (5) | sodium carboxymethyl starch | 8 kg |
| (6) | talcum | 2 kg |
| (7) | magnesium stearate | 1 kg |
| | | 100 kg |

Granulate a mixture of 1, 2, 3 and 4 (moistened in approximately 20 liters of water) through a sieve with a mesh width of 1.25 mm. Dry the resulting granulate in a fluidized bed drier to a relative moisture of from 50 to 60% by weight and then add thereto components 5, 6 and 7. Press the finished granulate to tablets with a diameter of 8 mm and a weight of 200 mg, each.

EXAMPLE 90

Tablets with 150 mg of Active Substance for Oral Application

| | | |
|---|---|---|
| (1) | 3-(5-nitro-2-furyl)-1-(2-pyridyl)pyrazole-4-carboxamide | 60 kg |
| (2) | lactose | 12 kg |
| (3) | maize starch | 8 kg |
| (4) | polyvinylpyrrolidone | 4 kg |
| (5) | sodium carboxymethyl starch | 10 kg |
| (6) | talcum | 4 kg |
| (7) | magnesium stearate | 2 kg |
| | | 100 kg |

Moisten an admixture of components 1, 2, 3 and 4 with approximately 20 liters of water and then granulate same with a sieve having a clearance mesh width of 1.25 mm. Dry the resulting granulate in a fluidized bed drier to a relative moisture of from 50 to 60% by weight and then add components 5, 6 and 7. After sieving the thus-prepared mixture, press it to 250 mg tablets having a diameter of 9 mm.

EXAMPLE 91

Vaginal Tablets with 100 mg of Active Substance

| (1) 3-(5-nitro-2-furyl)-1-(2-pyridyl)pyrazole-4-carboxamide | 10 kg |
|---|---|
| (2) lactose | 89 kg |
| (3) carboxymethylcellulose | 17 kg |
| (4) talcum | 4 kg |
| | 120 kg |

Moisten an admixture of components 1, 2 and 3 with 30 liters of water and granulate through a sieve with a clearance mesh width of 1.5 mm. Dry the obtained granulate to a relative moisture of from 50 to 60% by weight, mix it with compound 4 and, after sieving, press it to 1200 mg tablets.

Throughout the disclosure of compounds and structures thereof the nature of contemplated molecular substitution is virtually unlimited. Only illustrative substituents are indicated and exemplified. The sole limitation with regard to substituents is that they must not negate the usefulness of the compound for its intended purpose. For any compound which is to be used as a medicament, the molecular substitution thereon cannot be such as to render the compound unduly toxic or to negate the activity upon which the medicament utility is predicated. Those compounds which are internally, e.g. orally or parenterally administered to, e.g., mammals are therapeutically active and pharmacologically acceptable.

The invention encompasses all antimicrobially-active pyrazoles, the molecular structures of which have a pyrazole ring substituted by 5-nitro-2-furyl on a ring carbon atom ortho to one pyrazole-ring nitrogen atom and unsubstituted on the ring carbon atom ortho to the other pyrazole-ring nitrogen atom, the remaining carbon atom of that pyrazole ring bearing a carboxylic acid group or a derivative thereof. The derivative is, e.g., a salt (such as an alkali-metal salt, e.g. sodium salt) or an ester (such as a lower-alkyl ester, e.g. methyl ester) of the carboxylic acid or any of the other indicated meanings or variants thereof.

There is one term which is used in the working examples in a sense different from that in the descriptive portion of the specification. In the description of molecular structure "residue" has the meaning indicated on page 7 of the specification; in the working examples this word refers to separated precipitate or filter cake.

The preceding disclosure adequately apprises those of ordinary skill in the relevant art:

a. what the subject invention is, including its metes and bounds;

b. how to make and use the novel compounds from known chemicals or from chemicals which are synthesized by established and recognized procedures from available starting materials;

c. how to prepare the novel compositions; and d. how to use the compounds and the compositions, and makes it clear that changes in structure and composition components are readily made without departing from the spirit or scope of the instant teachings.

What is claimed is:

1. An antimicrobially-active pyrazole, the pyrazole ring of which is substituted by 5-nitro-2-furyl on a ring carbon atom ortho to one ring nitrogen atom and is unsubstituted on the ring carbon atom ortho to the other ring nitrogen atom, the pyrazole having the formula:

$$\begin{array}{c} B \quad\quad A \\ \diagdown \diagup \\ N \\ | \quad\quad \\ R^1 \quad N \end{array}$$

wherein $R^1$ is directly bound to one of the two nitrogen atoms of the pyrazole ring, is heterocycle-free, and is —H, substituted or unsubstituted hydrocarbyl, carboxylic acid acyl or carbonic acid acyl, the hydrocarbyl being saturated or unsaturated, acyclic, alicyclic or aromatic, or araliphatic;

A is —CN, —CH(=X), aminol, or —C(=U)—$R^{11}$;

U is =O, =S, =$NR^3$, =N—O—$R^4$ or =N—N($R^7$)$_2$;

X is =O, =S, =N—$R^3$, =N—O—$R^4$, =N—N($R^5$)$R^6$, {—O—(lower)-alkyl}$_2$, {—S—(lower)alkyl}$_2$, —O—Y—O— or —S—Y—S—;

Y is lower alkylene with from 2 to 5 carbon atoms and optionally substituted by alkyl with from one to 5 carbon atoms;

Z is =O, =S or =NH;

$R^3$ is one of the meanings of $R^1$;

$R^4$ is —H, alkanoyl with from 1 to 7 carbon atoms or aroyl;

$R^5$ is —H or optionally-substituted alkyl;

$R^6$ is one of the meanings of $R^7$ or —C(=Z)—N($R^7$)$R^8$;

each of $R^7$ and $R^8$ is, independently, —H, optionally-substituted alkyl, organic acyl or optionally-substituted aryl;

$R^{11}$ is —OH, alkoxy with from 1 to 11 carbon atoms, aryloxy with up to 12 carbon atoms, aralkoxy with up to 14 carbon atoms, halo, acyloxy, mercapto, azido, —N($R^{12}$)$R^{13}$, substituted or unsubstituted hydroxylamino or —NH—N($R^{14}$)$R^{15}$;

each of $R^{12}$ and $R^{13}$ is, independently, —H, alkyl having from one to 7 carbon atoms or hydroxyalkyl having from one to 7 carbon atoms;

each of $R^{14}$ and $R^{15}$, independently, has one of the meanings of $R^7$; and B is 5-nitro-2-furyl.

2. A pyrazole according to claim 1, wherein $R^1$ is —H, substituted or unsubstituted aliphatic hydrocarbyl, substituted or unsubstituted cycloaliphatic, substituted or unsubstituted aromatic, nuclearly-substituted or unsubstituted aralkyl, nuclearly-substituted or unsubstituted aralkenyl, or organic acyl of a carboxylic or carbonic acid.

3. A pyrazole according to claim 2 wherein $R^1$ is —H, lower aliphatic hydrocarbyl, alicyclic hydrocarbyl having from 3 to 7 ring carbon atoms, mono- to tricyclic aryl, monocyclic ar(lower)alkyl, carboxylic acid acyl or carbonic acid acyl.

4. A 4-pyrazolecarbaldehyde according to claim 3.

5. A pyrazole according to claim 3 wherein

A is —CH(=X); and

X is {—O—(lower)alkyl}$_2$ or {—S—(lower)alkyl}$_2$.

6. A pyrazole according to claim 3 wherein

A is —CH(=X);
X is =S, =N—R³, =N—O—R⁴ or =N—N(R⁵)R⁶; and
each of
R³, R⁴, R⁵ and R⁶ has its previously-ascribed meaning.

7. A 4-pyrazolecarbonitrile according to claim 3.

8. A 4-pyrazolecarboxylic acid according to claim 3.

9. A pyrazole according to claim 3 wherein
A is —CO—R¹¹ and
R¹¹ is alkoxy with from one to 11 carbon atoms, aryloxy with up to 12 carbon atoms or aralkoxy with up to 14 carbon atoms.

10. A pyrazole according to claim 3 wherein
A is —C(=U)—R¹¹ and other than —COOH; and
each of
U and R¹¹ has its previously-ascribed meaning.

11. A pyrazole according to claim 3 wherein R¹ is —H.

12. A pyrazole according to claim 3 wherein R¹ is lower aliphatic hydrocarbyl.

13. A pyrazole according to claim 3 wherein R¹ is alicyclic hydrocarbyl having from 3 to 7 carbon atoms.

14. A pyrazole according to claim 3 wherein R¹ is aryl.

15. A pyrazole according to claim 3 wherein R¹ is aralkyl.

16. A pyrazole according to claim 3 wherein R¹ is acyl.

17. A 1-R¹-3-(5-nitro-2-furyl)-4-pyrazole according to claim 3.

18. A 1-R¹-5-(5-nitro-2-furyl)-4-pyrazole according to claim 3.

19. A pyrazole according to claim 1 wherein A is —CHO, —CHS, acetal, mercaptal, aminal imino, oximino or hydrazono.

20. A pyrazole according to claim 19 wherein A is —CHO.

21. A pyrazole according to claim 1 wherein
A is —CH=X;
X is (—O—alkyl)₂, (—S—alkyl)₂, —O—Y—O— or —S—Y—S—;
Y is an alkylene bridge of from 2 to 5 carbon atoms optionally lower alkyl substituted; and alkyl is saturated aliphatic hydrocarbyl having from 1 to 5 carbon atoms.

22. A pyrazole according to claim 1 wherein
A is —CH=X;
X is =N-R³, =N—O—R⁴ or =N—N(R⁵)R⁶;
R³ is one of the meanings of R¹;
R⁴ is —H or acyl;
R⁵ is —H or optionally-substituted lower alkyl;
R⁶ is —H, optionally-substituted lower alkyl, optionally substituted aryl, organic acid acyl or —C³-Z—N⁴R⁷R⁸;
each of
R⁷ and R⁸ is, independently, acyl, optionally-substituted aryl, —H or optionally-substituted lower alkyl; and
Z is =O, =S or =NH.

23. A pyrazole according to claim 22 wherein
X is =N—O—R⁴ or =N—N(R⁵)R⁶;
R⁴ is —H or alkanoyl with from 1 to 4 carbon atoms;
R⁵ is —H₂ or alkyl with from 1 to 3 carbon atoms;
R⁶ is alkyl with from 1 to 3 carbon atoms, optionally (mono- or di-)substituted phenyl, —CZ—NR⁷R⁸, R⁹—CO— or R¹⁰—O—CO—;
each of
R⁷ and R⁸ is, independently, —H or methyl;
R⁹ is alkyl with from 1 to 4 carbon atoms and optionally-substituted by a substituent selected from the group consisting of methoxy, ethoxy and dimethylamino; phenyl; or mono- or disubstituted phenyl, any substituent of which is a member selected from the group consisting of methyl, methoxy, ethoxy, nitro, chloro, and bromo;
R¹⁰ is optionally-substituted alkyl with from 1 to 4 carbon atoms and
Z is =O or =S.

24. A pyrazole according to claim 23 wherein R⁴ is —H; R⁵ is —H, or methyl; R⁶ is methyl, phenyl, —C³-Z—N⁴(R⁷)R⁸, R⁹—CO— or R¹⁰—O—CO—; each of R⁷ and R⁸ is, independently, —H or methyl; R⁹ is alkyl having 1 to 2 carbon atoms; phenyl; or mono- or disubstituted phenyl, any substituent of which is a member selected from the group consisting of methyl, methoxy, ethoxy, nitro, chloro or bromo; R¹⁰ is C₁₋₄-alkyl; and Z is =O or =S.

25. A pyrazole according to claim 1 in which A is —CH(=X); X is =O, hydroxylimino or =N—N-H—C(=O)OR¹⁰; and R¹⁰ is alkyl with from 1 to 4 carbon atoms.

26. A pyrazole according to claim 25 in which R¹⁰ is ethyl.

27. A pyrazole according to claim 1 wherein A is —CN.

28. A pyrazole according to claim 1 in which A is —C(=U)R¹¹; R¹¹ is hydroxy, alkoxy with from 1 to 11 carbon atoms, aryloxy with up to 12 carbon atoms, aralkoxy with up to 14 carbon atoms, acyloxy, mercapto, azido, —N(R¹²)R¹³, hydroxylamino or —N-H—HR¹⁴R¹⁵; R¹² is —H or C₁₋₇-alkyl; R¹³ is —H or C₁₋₇-alkyl; each of R¹⁴ and R¹⁵ is, independently, acyl, optionally-substituted aryl, —H or optionally-substituted lower alkyl, U is =O, =S, =NH, =N—R³, =N—O—R⁴ or =N—N(R⁷)₂; R³ is one of the meanings of R¹; R⁴ is —H or acyl; R⁷ is one of the meanings of R¹⁴.

29. A pyrazole according to claim 28 wherein U is =O, R¹¹ is —OH or

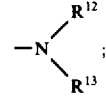

and each of R¹² and R¹³ is, independently, —H or straight-chained alkyl with from 1 to 4 carbon atoms and optionally substituted by —OH.

30. A pyrazole according to claim 29 wherein U is =O and R¹¹ is —NH₂.

31. A pyrazole according to claim 1 wherein R¹ is —H, alkyl with from 1 to 4 carbon atoms and optionally substituted by hydroxy, methoxy, ethoxy or acetoxy, unsubstituted or monosubstituted benzyl, allyl, phenyl or mono- or disubstituted phenyl, any substituent of substituted benzyl or of substituted phenyl being a nuclear substituent selected from the group consisting of halo, methyl, methoxy, trifluoromethyl and nitro, and alkoxycarbonyl.

32. A pyrazole according to claim 31 wherein R¹ is —H, methyl, ethyl optionally substituted by hydroxy, methoxy, ethoxy or acetoxy in the 2-position, benzyl, p-halophenyl, p-tolyl, p-methoxyphenyl, phenyl, p-nitrophenyl, lower alkoxy-carbonyl, or allyl.

33. A pyrazole according to claim 32 wherein $R^1$ is —H, methyl, p-fluorophenyl, p-chlorophenyl, phenyl, methoxycarbonyl or ethoxycarbonyl.

34. A pyrazole according to claim 1 wherein $R^1$ is —H, optionally-substituted $C_{1-4}$-alkyl, benzyl, monosubstituted benzyl, allyl, phenyl, mono- or disubstituted phenyl, or lower alkoxycarbonyl; any substituent of substituted alkyl being hydroxy, methoxy, ethoxy or acetoxy; and any substituent of substituted benzyl or of substituted phenyl being a nuclear substituent selected from the group consisting of halo, methyl, methoxy, trifluoromethyl and nitro.

35. A pyrazole according to claim 34, wherein A is —CH=X; X is (—O—alkyl)$_2$, (—S—alkyl)$_2$, —O—Y—O—, —S—Y—S, =O, =S, =N—$R^3$, =N—O—$R^4$ or =N—$^2R^5R^6$; alkyl is saturated aliphatic hydrocarbyl having from 1 to 5 carbon atoms; Y is an alkylene bridge of from 2 to 5 carbon atoms optionally lower alkyl substituted; $R^3$ is —H; $R^4$ is —H; $R^5$ is —H, or methyl; $R^6$ is methyl, phenyl, —$C^3Z$—$N^4(R^7)R^8$, $R^9$—CO— or $R^{10}$—O—CO—; each of $R^7$ and $R^8$ is, independently, —H or methyl; $R^9$ is alkyl having 1 or 2 carbon atoms; phenyl; mono- or disubstituted phenyl, any substituent of which is a member selected from the group consisting of methyl, methoxy, ethoxy, nitro, chloro or bromo; $R^{10}$ is $C_{1-4}$-alkyl; and Z is =O or =S.

36. A pyrazole according to claim 35 wherein $R^1$ is —H, methyl, ethyl, $\beta$-substituted ethyl, benzyl, ph-chloro-benzyl, allyl, phenyl, p-substituted phenyl or lower alkoxy carbonyl; any substituent of $\beta$-substituted ethyl being a member selected from the group consisting of hydroxy, methoxy, ethoxy and acetoxy; and any substituent of p-substituted phenyl being a member selected from the group consisting of halo, methyl, methoxy and nitro.

37. A pyrazole according to claim 36 wherein $R^1$ is —H, methyl, phenyl, p-fluorophenyl, p-chlorophenyl, methoxycarbonyl or ethoxycarbonyl.

38. A pyrazole according to claim 27 wherein $R^1$ is —H, optionally-substituted $C_{1-4}$-alkyl, optionally monosubstituted benzyl, allyl, phenyl, mono- or disubstituted phenyl or alkoxycarbonyl; any substituent of substituted alkyl being a member selected from the group consisting of hydroxy, methoxy, ethoxy and acetoxy; and any substituent of benzyl or of phenyl being a nuclear substituent selected from the group consisting of halo, methyl, methoxy, trifluoromethyl and nitro.

39. A pyrazole according to claim 38 wherein $R^1$ is —H, methyl, ethyl, $\beta$-substituted ethyl, benzyl, p-chloro-benzyl, allyl, phenyl, p-[halo, methyl, methoxy or nitro]substituted phenyl or lower alkoxycarbonyl.

40. A pyrazole according to claim 39 wherein $R^1$ is —H, methyl, phenyl, p-fluorophenyl, p-chlorophenyl, methoxy-carbonyl or ethoxycarbonyl.

41. A pyrazole according to claim 34 wherein A is —CU—$R^{11}$; U is =O, =S, =N—$R^3$, =N—O—$R^4$ or =N—N($R^7$)$_2$; $R^3$ is one of the meanings of $R^1$; $R^4$ is —H or (organic acid)acyl; $R^7$ is —H, (organic acid)acyl, optionally-substituted aryl or optionally-substituted lower alkyl; $R^{11}$ is hydroxy, alkoxy with from 1 to 11 carbon atoms, aryloxy with up to 12 carbon atoms, aralkoxy with up to 14 carbon atoms, halo, (organic acid) acyloxy, mercapto, azido, —N($R^{12}$)$R^{13}$, hydroxylamino or —NH—N($R^{14}$)$R^{15}$; $R^{12}$ is —H or $C_{1-7}$-alkyl; $R^{13}$ is —H or $C_{1-7}$-alkyl; each of $R^{14}$ and $R^{15}$ is, independently, (organic acid)acyl, optionally-substituted aryl, —H or optionally-substituted lower alkyl.

42. A pyrazole according to claim 41 wherein $R^1$ is —H, methyl, ethyl, $\beta$-substituted ethyl, benzyl, p-chloro-benzyl, allyl, phenyl, p-[halo, methyl, methoxy or nitro]substituted phenyl or lower alkoxycarbonyl.

43. A pyrazole according to claim 42 wherein $R^1$ is —H, methyl, phenyl, p-fluorophenyl, p-chlorophenyl, methoxycarbonyl, or ethoxycarbonyl.

44. A pyrazole according to claim 1 wherein $R^1$ is —H, methyl, ethyl, methoxycarbonyl or ethoxycarbonyl.

45. A pyrazole according to claim 1 wherein $R^1$ is aryl.

46. A pyrazole according to claim 45 wherein $R^1$ is phenyl, mono-substituted phenyl or disubstituted phenyl; any substituent of a substituted phenyl being halo, methyl or methoxy.

47. A pyrazole according to claim 46 wherein $R^1$ is phenyl, p-fluorophenyl or p-chlorophenyl.

48. A pyrazole according to claim 27 wherein $R^1$ is —H, methyl, ethyl, methoxycarbonyl or ethoxycarbonyl.

49. A pyrazole according to claim 27 wherein $R^1$ is aryl.

50. A pyrazole according to claim 49 wherein $R^1$ is phenyl, monosubstituted phenyl or disubstituted phenyl; any substituent of a substituted phenyl being halo, methyl or methoxy.

51. A pyrazole according to claim 50 wherein $R^1$ is phenyl, p-fluorophenyl or p-chlorophenyl.

52. A pyrazole according to claim 41 wherein $R^1$ is —H, methyl, ethyl, methoxycarbonyl or ethoxycarbonyl.

53. A pyrazole according to claim 41 wherein $R^1$ is aryl.

54. A pyrazole according to claim 53 wherein $R^1$ is phenyl, monosubstituted phenyl or disubstituted phenyl, any substituent of a substituted phenyl being a member selected from the group consisting of halo, methyl and methoxy.

55. A pyrazole according to claim 54 wherein $R^1$ is phenyl, p-fluorophenyl or p-chlorophenyl.

56. The pyrazole according to claim 1 which is 1-methyl-3-(5-nitro-2-furyl)pyrazole-4-carboxaldehyde-ethoxycarbonylhydrazone.

57. The pyrazole according to claim 1 which is 3-(5-nitro-2-furyl)-1-phenylpyrazole-4-carboxaldehyde-ethoxycarbonylhydrazone.

58. The pyrazole according to claim 1 which is 1-methyl-3-(5-nitro-2-furyl)pyrazole-4-carbonitrile.

59. The pyrazole according to claim 1 which is 1-methyl-5-(5-nitro-2-furyl)pyrazole-4-carboxamide.

60. The pyrazole according to claim 1 which is 3-(5-nitro-2-furyl)-1-phenylpyrazole-4-carboxamide.

61. The pyrazole according to claim 1 which is 1-(p-chlorophenyl)-3-(5-nitro-2-furyl))pyrazole-4-carboxamide.

62. The pyrazole according to claim 1 which is 1-(p-fluorophenyl)-3-(5-nitro-2-furyl)pyrazole-4-carboxamide.

63. A pyrazole according to claim 41 wherein U is =O and $R^{11}$ is —OH or —N($R^{12}$)$R^{13}$, wherein each of $R^{12}$ and $R^{13}$ independently, is —H or alkyl with from 1 to 4 carbon atoms and optionally substituted by —OH.

64. A pyrazole according to claim 63, wherein $R^1$ is —H, methyl, ethyl, $\beta$-substituted ethyl, benzyl, p-

65. A pyrazole according to claim 64 wherein $R^1$ is —H, methyl, phenyl, p-fluorophenyl, p-chlorophenyl, methoxycarbonyl or ethoxycarbonyl.

66. A pyrazole according to claim 41 wherein U is $=\!\!O$ and $R^{11}$ is $-\!NH_2$.

67. A pyrazole according to claim 66 wherein $R^1$ is —H, methyl, ethyl, β-substituted ethyl, benzyl, p-chlorobenzyl, allyl, phenyl, p-[halo, methyl, methoxy or nitro]-substituted phenyl or lower alkoxycarbonyl.

68. A pyrazole according to claim 67 wherein $R^1$ is —H, methyl, phenyl, p-fluorophenyl, p-chlorophenyl, methoxycarbonyl or ethoxycarbonyl.

69. A pyrazole according to claim 20 wherein $R^1$ is —H, methyl, ethyl, methoxycarbonyl or ethoxycarbonyl.

70. A pyrazole according to claim 20 wherein $R^1$ is aryl.

71. A pyrazole according to claim 70 wherein $R^1$ is phenyl, mono-substituted phenyl or disubstituted phenyl; any substituent of a substituted phenyl being halo, methyl or methoxy.

72. A pyrazole according to claim 71 wherein $R^1$ is phenyl, p-fluorophenyl or p-chlorophenyl.

73. A pyrazole according to claim 24 wherein $R^1$ is —H, methyl, ethyl, methoxycarbonyl or ethoxycarbonyl.

74. A pyrazole according to claim 24 wherein $R^1$ is aryl.

75. A pyrazole according to claim 74 wherein $R^1$ is phenyl, mono-substituted phenyl or disubstituted phenyl; any substituent of a substituted phenyl being halo, methyl or methoxy.

76. A pyrazole according to claim 75 wherein $R^1$ is phenyl, p-fluorophenyl or p-chlorophenyl.

77. A pyrazole according to claim 25 wherein $R^1$ is —H, methyl, ethyl, methoxycarbonyl or ethoxycarbonyl.

78. A pyrazole according to claim 25 wherein $R^1$ is aryl.

79. A pyrazole according to claim 78 wherein $R^1$ is phenyl, mono-substituted phenyl or disubstituted phenyl; any substituent of a substituted phenyl being halo, methyl or methoxy.

80. A pyrazole according to claim 79 wherein $R^1$ is phenyl, p-fluorophenyl or p-chlorophenyl.

81. An antimicrobially-active pyrazole, the pyrazole ring of which is substituted by 5-nitro-2-furyl on a ring carbon atom ortho to one ring nitrogen atom and is unsubstituted on the ring carbon atom ortho to the other ring nitrogen atom;

the remaining ring carbon atom bearing a non-heterocyclic substituent selected from the group consisting of —CN,

wherein
D is $=\!\!O$, $=\!\!S$, $=\!\!NR^3$, $=\!\!NOR^4$ or $=\!\!N\!-\!N(R^5)R^6$;
$R^3$ is —H, substituted or unsubstituted hydrocarbyl, carboxylic acid acyl or carbonic acid acyl; any substituent of substituted aliphatic hydrocarbyl being halo, hydroxyl, lower alkoxy, acyloxy or aryloxy; any substituent of substituted aromatic hydrocarbyl being halo, lower alkyl, lower alkoxy, lower alkymercapto, trifluoromethyl, nitro, cyclohexyl or phenyl; any nuclear substituent of aralkyl or aralkenyl hydrocarbyl being halo, lower alkyl, lower alkoxy, lower alkylmercapto, trifluoromethyl, nitro, cyclohexyl or phenyl; any non-nuclear substituent of aralkyl or aralkenyl hydro being halo, hydroxyl, lower alkoxy, acyloxy or aryloxy; any substituent of substituted alkanoic carboxylic acid acyl or of substituted alkanoic carbonic acid acyl being hydroxyl, lower alkoxy, mono(lower)alkylamino, dialkylamino or aryl; any nuclear substituent of substituted aromatic carboxylic acid acyl or of substituted aromatic carbonic acid acyl being halo, hydroxyl, lower alkyl, lower alkoxy or nitro; and any substituent of substituted cycloaliphatic hydrocarbyl being alkyl having from 1 to 4 carbon atoms, any substituted cycloaliphatic bearing at most two substituents;
$R^4$ is —H, alkanoyl with from 1 to 7 carbon atoms or aroyl;
$R^5$ is —H or optionally-substituted alkyl; any substituent of substituted alkyl being halo, hydroxyl, lower alkoxy, acyloxy or aryloxy;
$R^6$ is one of the meanings of $R^7$ or $C(=\!\!Z)\!-\!N(R^7)R^8$;
each of $R^7$ and $R^8$ is, independently, -H, optionally-substituted alkyl, organic acid acyl or optionally-substituted aryl; any substituent of optionally-substituted alkyl being halo, hydroxyl, lower alkoxy, acyloxy or aryloxy; and any substituent of optionally-substituted aryl being halo, lower alkyl, lower alkoxy, lower alkylmercapto, trifluoromethyl, nitro, cyclohexyl or phenyl;
Z is $=\!\!O$, $=\!\!S$ or $=\!\!NH$;
E is $=\!\!S$, $=\!\!O$, $=\!\!NR^3$, $=\!\!N\!-\!O\!-\!R^4$ or $=\!\!N\!-\!N(R^7)_2$;
G is —OH, halo, acyloxy, mercapto, azido, $-N(R^{12})R^{13}$ or $-NH\!-\!N(R^{14})R^{15}$; each of $R^{12}$ and $R^{13}$ is, independently, -H or alkyl having from 1 to 7 carbon atoms and optionally-substituted by —OH;
each of $R^{14}$ and $R^{15}$ is, independently, one of the meanings of $R^7$;
M is di(lower)alkoxy or di(lower)alkylmercapto;
Q is alkoxy with from 1 to 11 carbon atoms, aryloxy with up to 12 carbon atoms or aralkoxy with up to 14 carbon atoms; and
one of the ring nitrogen atoms being additionally bound to a nonheterocyclic member which, independently, has one of the meanings of $R^3$.

82. An antimicrobially-active pyrazole according to claim 81 wherein D is $=\!\!N\!-\!N(R^5)R^6$.

83. An antimicrobially-active pyrazole according to claim 82 wherein $R^6$ is one of the meanings of $R^7$.

84. An antimicrobially-active pyrazole according to claim 81 wherein the pyrazole ring is substituted in the 4-position by

85. A pyrazole according to claim 1 wherein X is $=\!\!O$, $=\!\!S$, $=\!\!N\!-\!R^3$, $=\!\!N\!-\!O\!-\!R^4$, $=\!\!N\!-\!N(R^5)R^6$, di(lower)alkoxy or di(lower)alkylmercapto.

* * * * *